(12) United States Patent
Rogers et al.

(10) Patent No.: US 11,439,356 B2
(45) Date of Patent: Sep. 13, 2022

(54) WIRELESS AND NONINVASIVE EPIDERMAL ELECTRONICS

(71) Applicant: NORTHWESTERN UNIVERSITY, Evanston, IL (US)

(72) Inventors: John A. Rogers, Wilmette, IL (US); Siddharth Krishnan, Evanston, IL (US); Tyler R. Ray, Evanston, IL (US); Amit B. Ayer, Evanston, IL (US); Philipp Gutruf, Evanston, IL (US); Jonathan T. Reeder, Evanston, IL (US); Kun Hyuck Lee, Morton Grove, IL (US); Chun-Ju Su, Evanston, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 0 days.

(21) Appl. No.: 17/568,771

(22) Filed: Jan. 5, 2022

(65) Prior Publication Data
US 2022/0125389 A1  Apr. 28, 2022

Related U.S. Application Data

(62) Division of application No. 17/043,111, filed as application No. PCT/US2019/025009 on Mar. 29, 2019, now Pat. No. 11,259,754.

(60) Provisional application No. 62/791,390, filed on Jan. 11, 2019, provisional application No. 62/650,826, filed on Mar. 30, 2018.

(51) Int. Cl.
A61B 5/00 (2006.01)
A61B 5/01 (2006.01)

(52) U.S. Cl.
CPC .............. *A61B 5/7278* (2013.01); *A61B 5/01* (2013.01); *A61B 2562/0271* (2013.01); *A61B 2562/164* (2013.01); *A61B 2562/18* (2013.01)

(58) Field of Classification Search
CPC ......... A61B 5/01; A61B 5/145; A61B 5/7278; A61B 5/150053; A61B 5/150076; A61B 2562/164; A61B 2562/0271
See application file for complete search history.

(56) References Cited

U.S. PATENT DOCUMENTS

| | | | |
|---|---|---|---|
| 2009/0164163 A1* | 6/2009 | Wang | G01F 1/698 73/204.25 |
| 2012/0238901 A1* | 9/2012 | Augustine | A61B 5/01 600/549 |
| 2016/0113518 A1* | 4/2016 | Narayan | A61B 5/01 600/504 |

FOREIGN PATENT DOCUMENTS

| | | | | |
|---|---|---|---|---|
| WO | WO-03037178 A2 * | 5/2003 | ......... | A61B 5/14532 |
| WO | WO-2012112222 A1 * | 8/2012 | ............... | A61B 5/01 |

* cited by examiner

*Primary Examiner* — Daniel L Cerioni
*Assistant Examiner* — Raymond P Dulman
(74) *Attorney, Agent, or Firm* — Locke Lord LLP; Tim Tingkang Xia, Esq.

(57) ABSTRACT

Provided are conformable devices to measure subdermal fluid flow and related methods. A soft, stretchable and flexible substrate supports a thermal actuator and various specially positioned temperature sensors. A microprocessor in electronic communication with sensors calculates subdermal fluid flow from the measured upstream and downstream temperatures, as well as various application-dependent parameters. Devices and methods provided herein are particularly useful for measuring cerebral spinal fluid in a ventricular shunt placed for treatment of hydrocephalus.

3 Claims, 84 Drawing Sheets

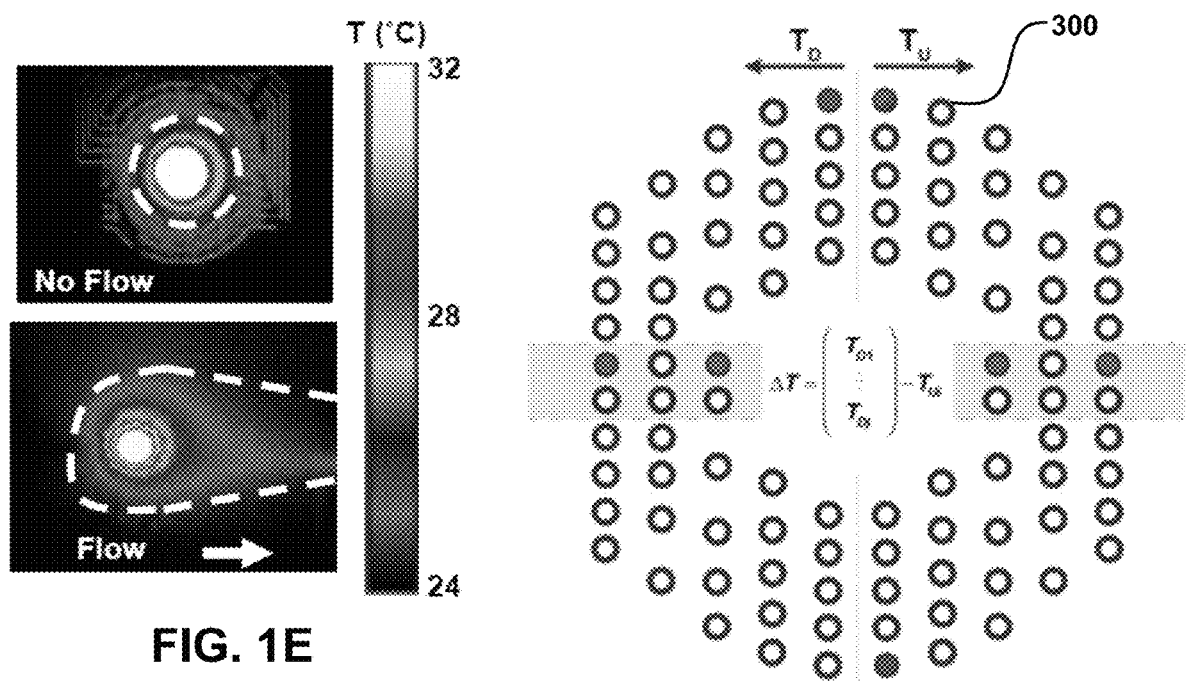
FIG. 1E
FIG. 2A
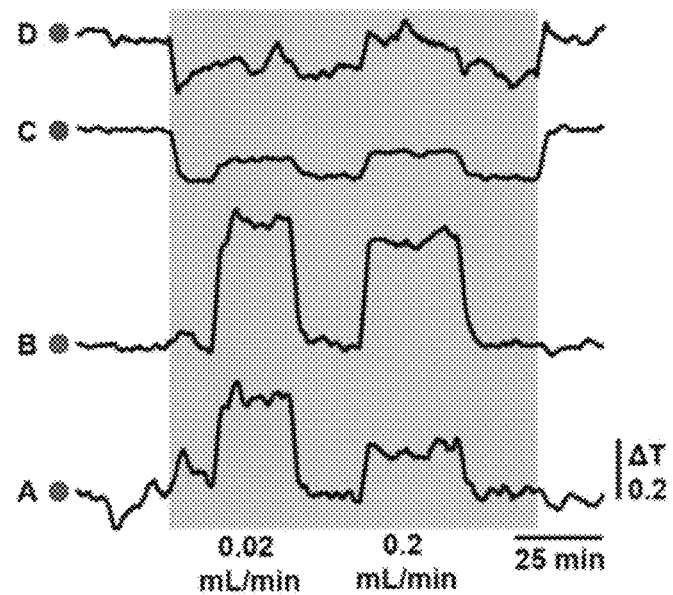
FIG. 2B

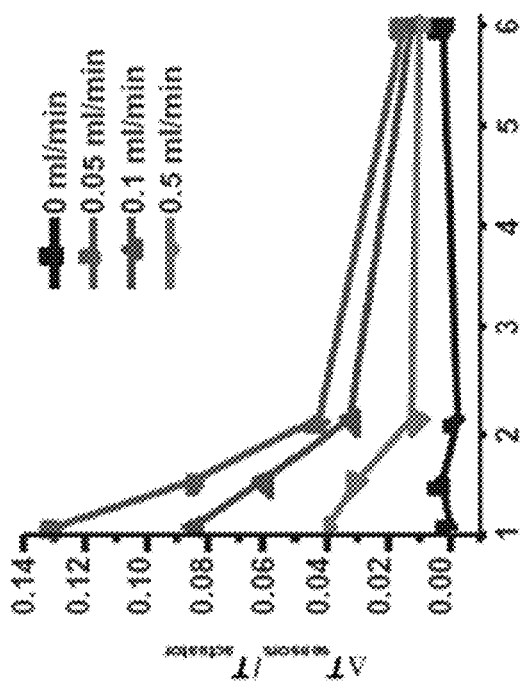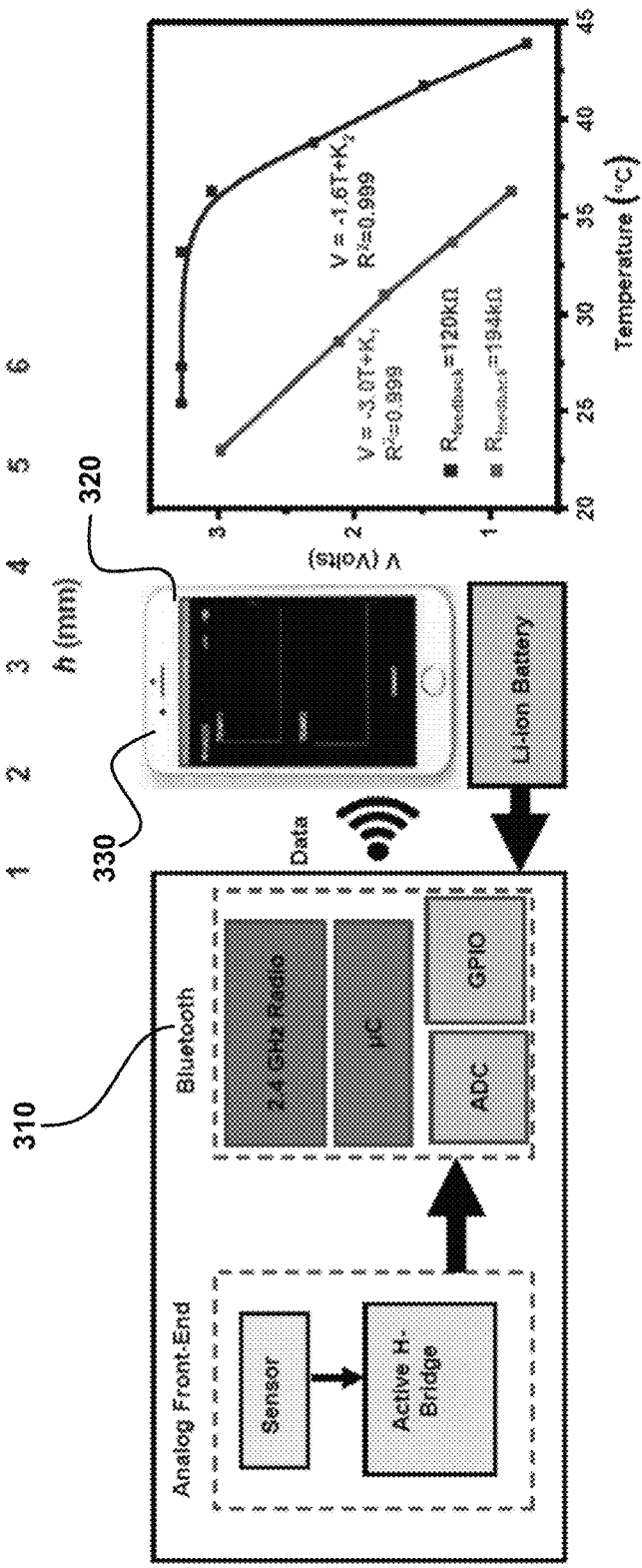
FIG. 3L
FIG. 4A

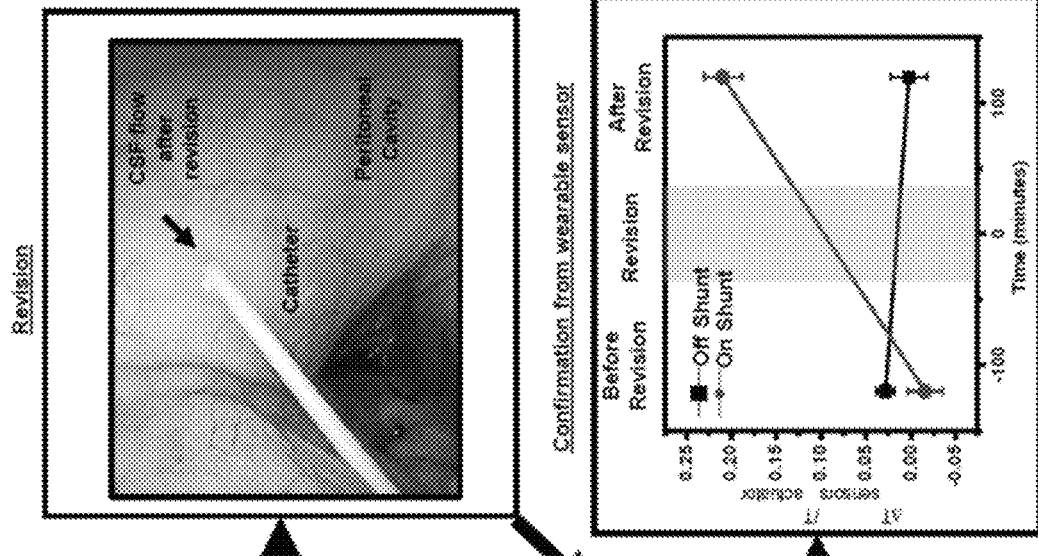
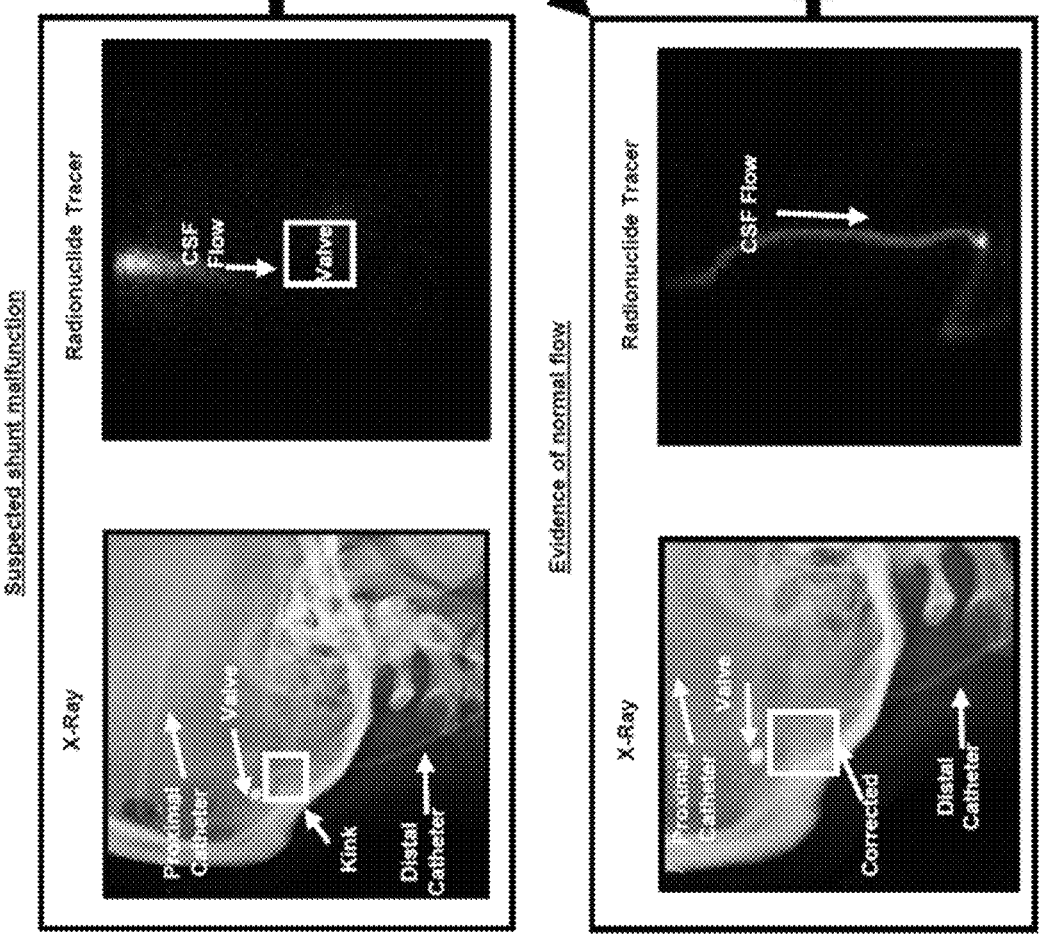
FIG. 6A  FIG. 6B  FIG. 6C  FIG. 6D

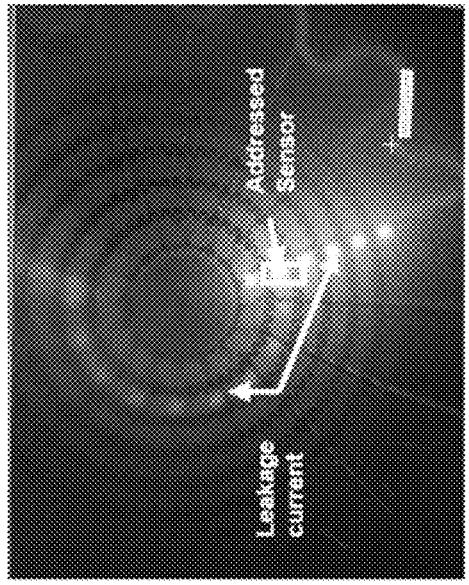
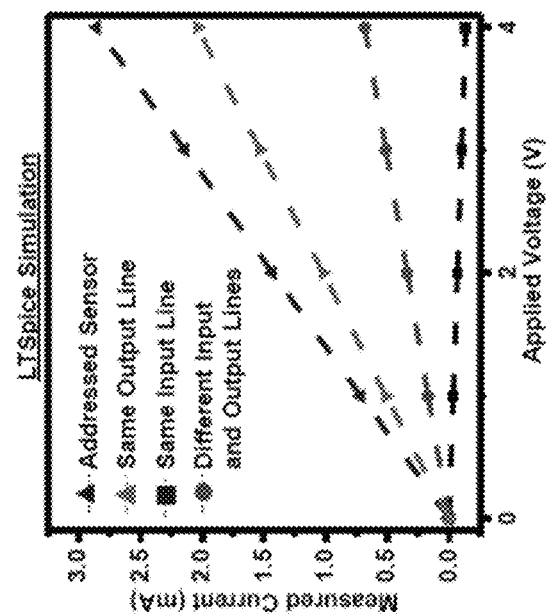
FIG. 8B
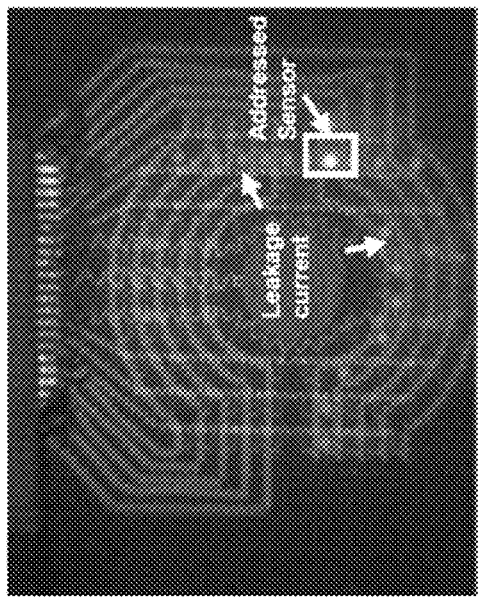
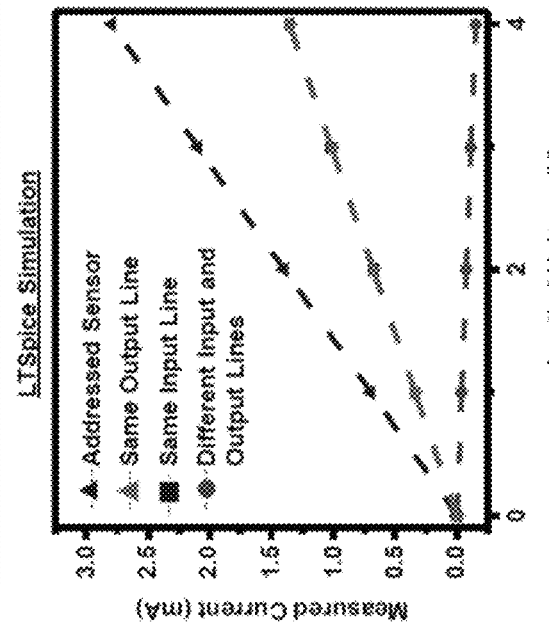
FIG. 8A

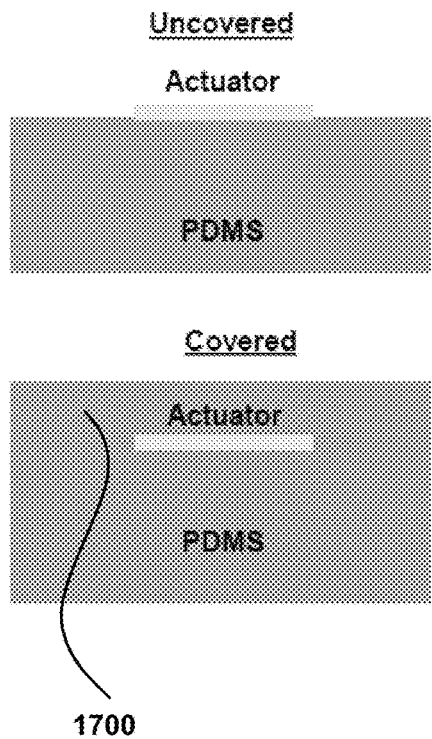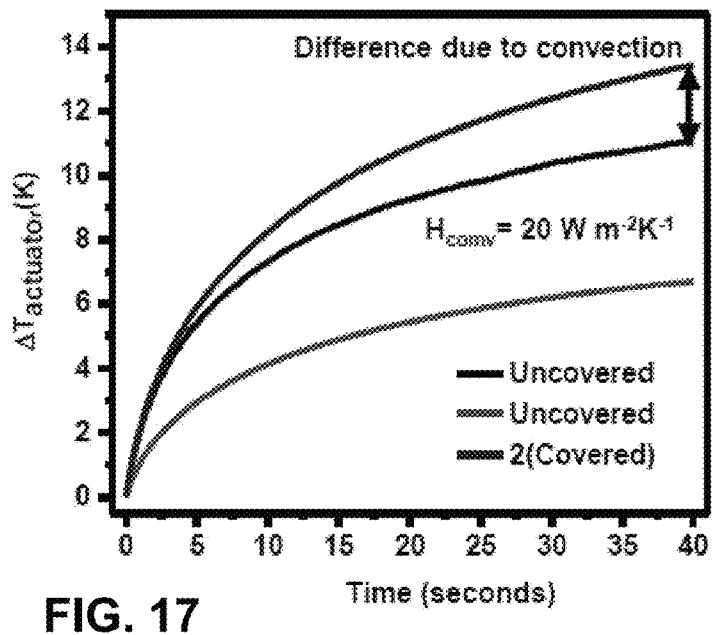
FIG. 17
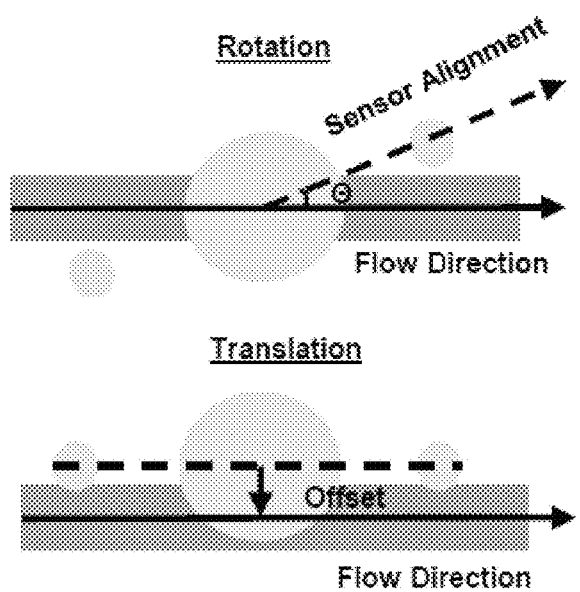
FIG. 18A

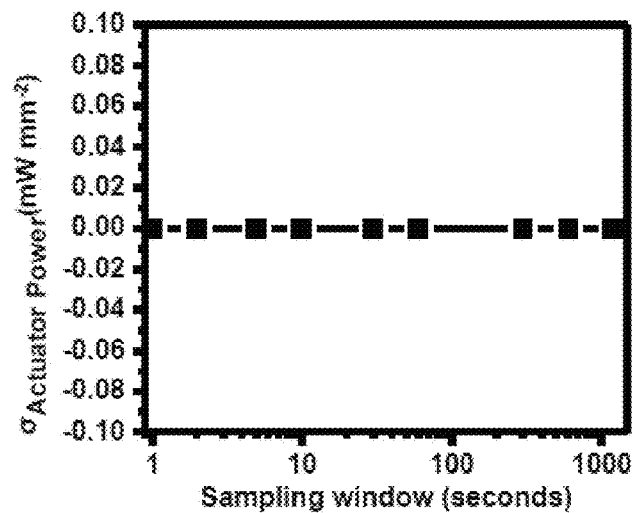
FIG. 19C
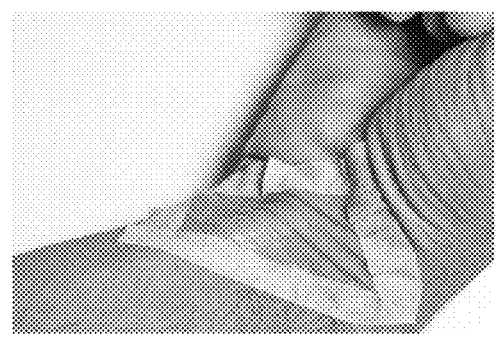
FIG. 20
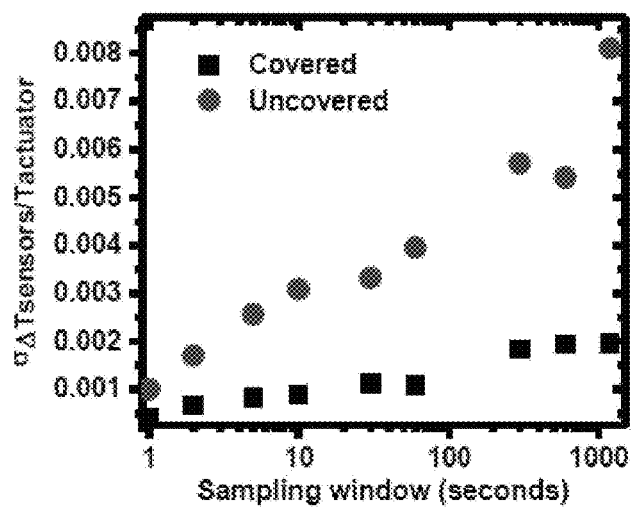
FIG. 19D

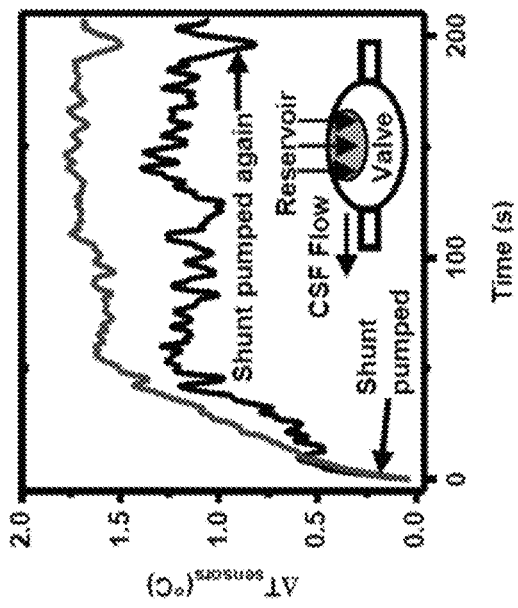
FIG. 21B
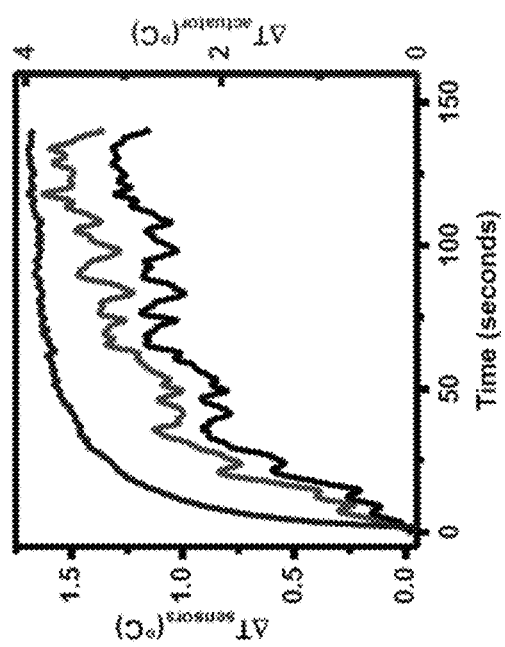
FIG. 21A
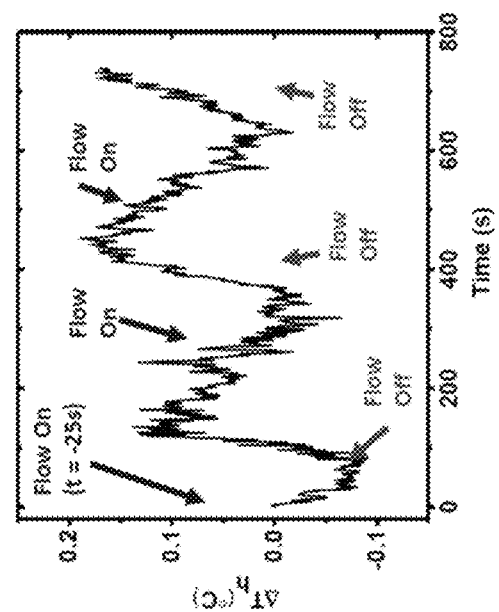
FIG. 22

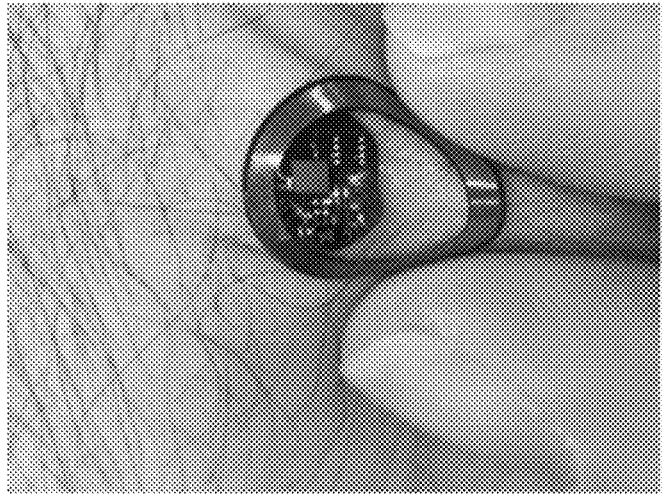
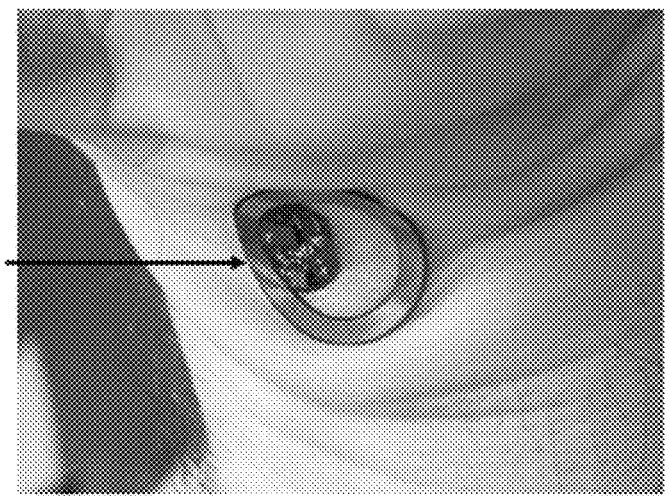
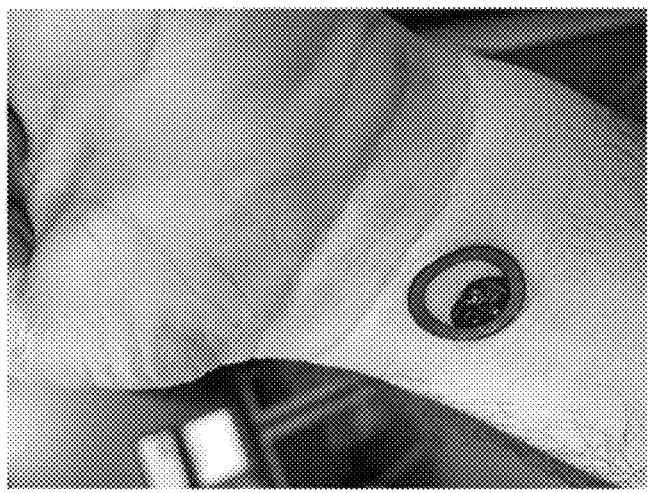
Delamination at edges, but crack doesn't propagate and center is conformal with skin
Work of Adhesion
MG 7-9850 → 1.25 N/m
MG 7-9850 → 4.4 N/m
MG 7-9090 → 76 N/m
MG 7-1010 → 160 N/m → Our choice
Dow Corning
FIG. 27

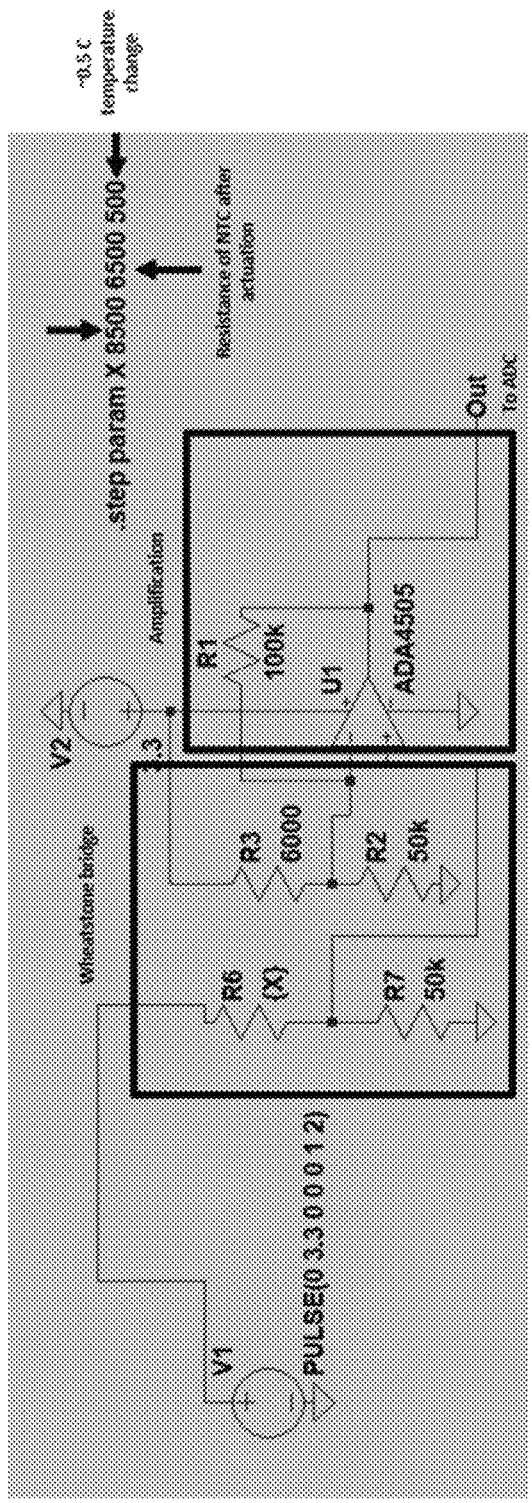 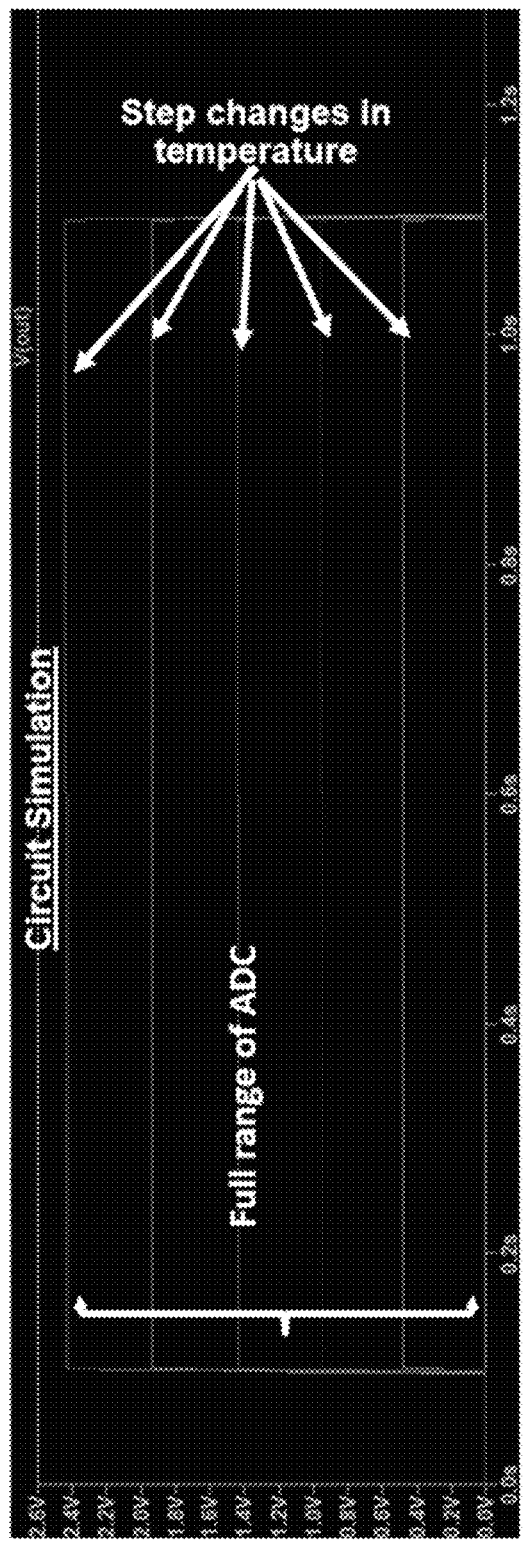
FIG. 32

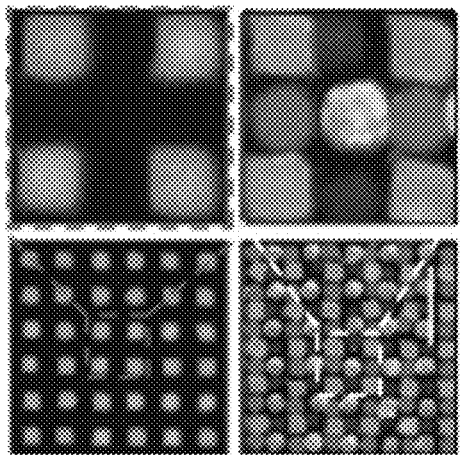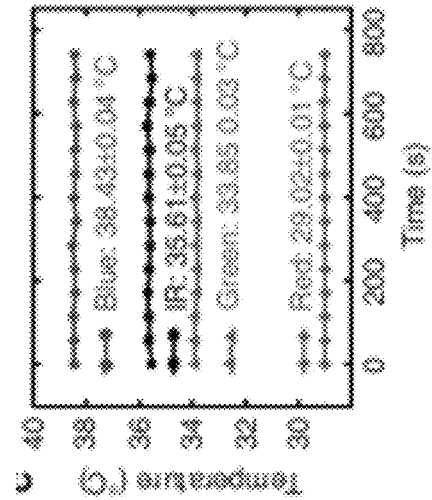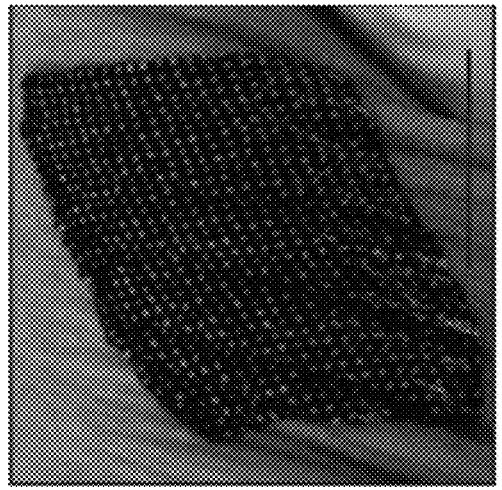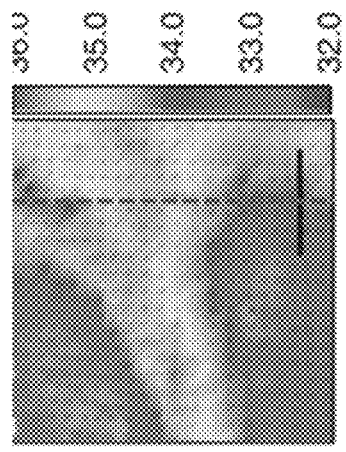
FIG. 33

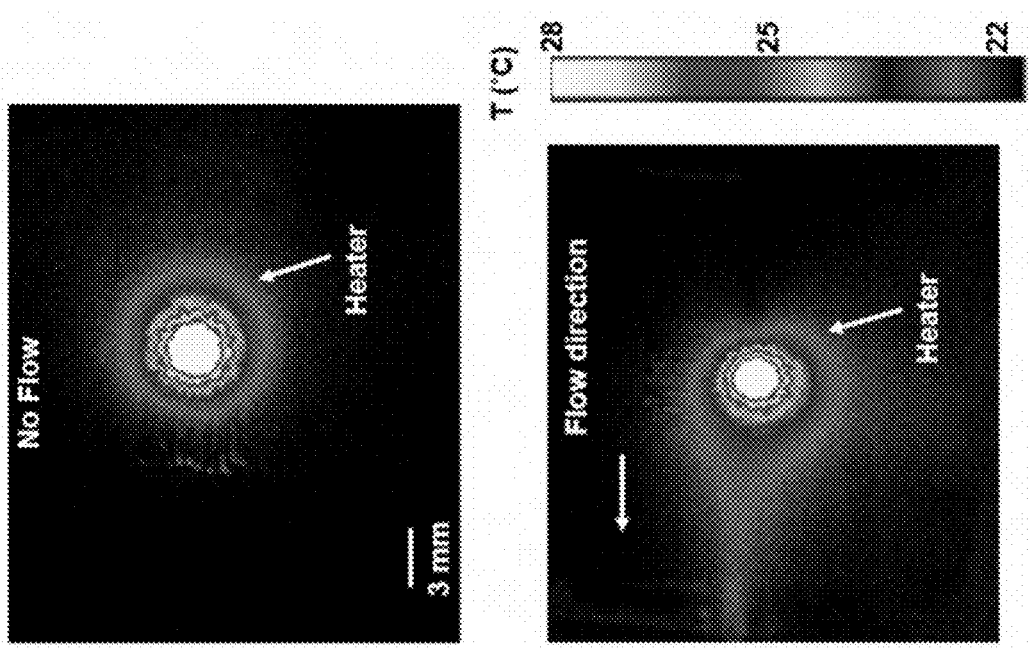
FIG. 34

- 4 patients so far- 3 were with appropriate alignment, no obvious errors with the protocol- data shown here
- Patient 4 had a number of complications with positioning, shunt placement and mistake with clinical protocol, and data is correspondingly useless Checklist:

———— On Shunt ————

1) Mount adhesive- paper side goes to device (acrylate), waxy side on patient (silicone). Both sides have backing.
2) Carefully mount over shunt, press sides down for 5 s, then press center with foam for 10s with firm but gentle pressure.
2) Make sure app is off before starting
3) Open app- 'BLE HRS' on shunt phone, blue thumbnail
4) Turn on switch, pair with device, start reading
5) Measurement lasts 5 minutes.
6) When measurement done, hit disconnect, quit app.
7) Wait 4 minutes.
8) Repeat steps 3-6 again.

———— Off shunt ————

9) Gently peel device off, make sure adhesive is still flat against device.
10) Place on adjacent location free of near-surface *macrovessels*. Microvessels (e.g. capillaries with no directionality) are fine.
11) Repeat steps 1-8 again.

Things to watch for:
- Take pictures of every device placement
- Make detailed notes in case of any aberrant patient or sensor behavior
- Make sure device is well aligned to shunt
- for 'on shunt', avoid wrinkling induced delamination by making patient face away and keeping their skin taut.
- Off shunt can be on a flatter location, but monitor location and note when patient speaks or moves suddenly.

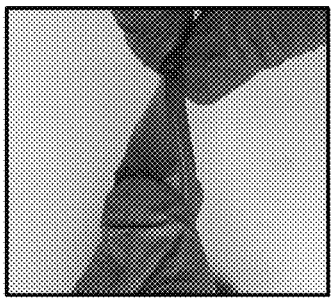
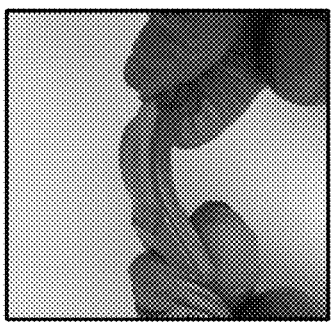
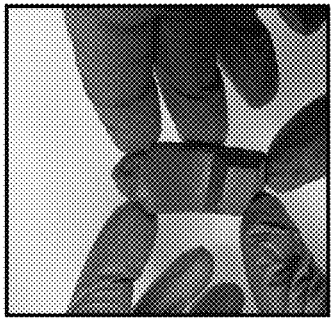
FIG. 53B
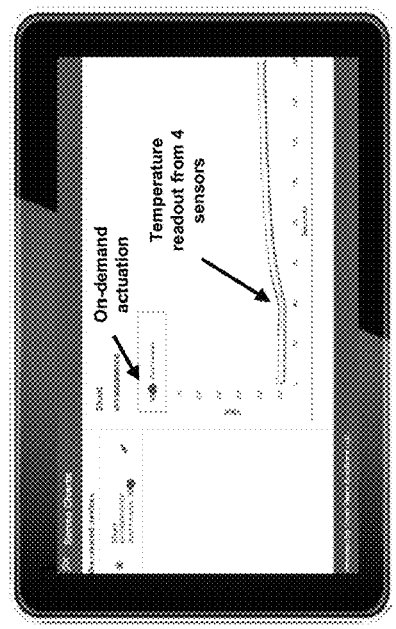
FIG. 53D
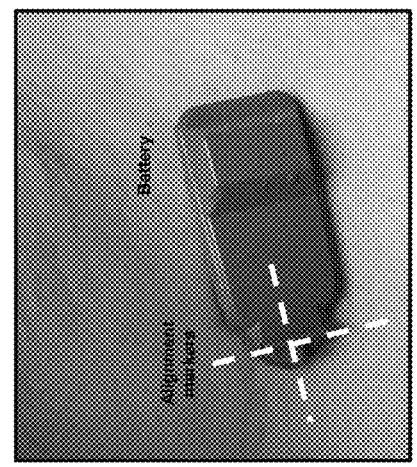
FIG. 53C
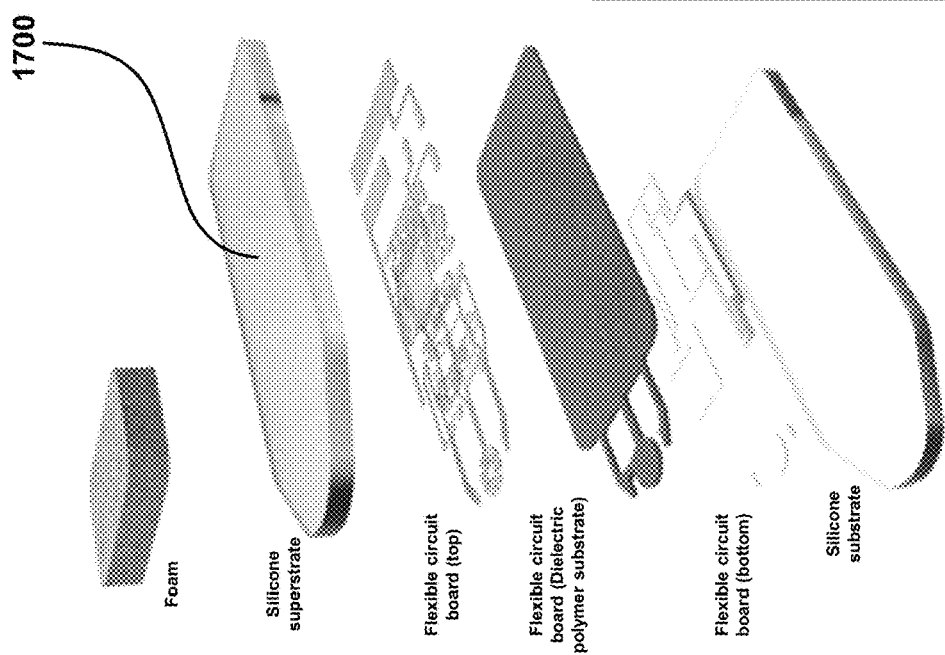
FIG. 53A

On Shunt
Off Shunt
On Shunt
Off Shunt
On Shunt
Off Shunt
FIG. 66

WIRELESS AND NONINVASIVE EPIDERMAL ELECTRONICS

CROSS-REFERENCE TO RELATED APPLICATIONS

This application is a divisional application of U.S. patent application Ser. No. 17/043,111, filed Sep. 29, 2020, now allowed, which is a national stage entry of PCT Patent Application Serial No. PCT/US2019/025009, filed Mar. 29, 2019, which itself claims the benefit of and priority to U.S. Provisional Patent Application No. 62/650,826 filed Mar. 30, 2018, and U.S. Provisional Patent Application No. 62/791,390, filed Jan. 11, 2019, each of which is specifically incorporated by reference in its entirety to the extent not inconsistent herewith.

STATEMENT REGARDING FEDERALLY SPONSORED RESEARCH OR DEVELOPMENT

Not applicable.

BACKGROUND OF INVENTION

Hydrocephalus and shunt-related expenditures cost the US system over $2 billion dollars in annual expenses, with 125,000 shunt surgeries per year and an untreated mortality rate estimated at 50-60%. Existing diagnostics are expensive, inaccurate, and often harmful or invasive, and can lead to unnecessary admissions, further testing, or needless surgery. To address these issues, provided herein is a noninvasive, thermal biosensor capable of diagnosing ventricular shunt malfunction.

Hydrocephalus is a common and costly condition caused by the accumulation of cerebrospinal fluid in the brain. It occurs in 1-5 of every 1000 live births, and over 70,000 patients are admitted and diagnosed yearly in the United States. Cerebrospinal fluid (CSF) is produced within the ventricles of the brain and is responsible for its nourishment and protection, but dysfunction in its drainage or reabsorption can lead to devastating neurological complications. Symptoms may include headache, lethargy, seizures, coma, or death, and untreated hydrocephalus has a mortality rate estimated at 50-60%. Pediatric hydrocephalus accounts for 38% of patients, and related surgeries are the most common neurosurgical procedures performed in children. Adult hydrocephalus can be seen as the sequelae to many conditions (such as tumors, trauma and infection) or in normal pressure hydrocephalus (NPH), an increasingly diagnosed condition which currently affects 375,000 patients in the United States. Often underdiagnosed or misdiagnosed for dementia and with 25% of those diagnosed shunted, this represents a growing segment of hydrocephalus related care. The mainstay of treatment for hydrocephalus involves the use of CSF diversion accomplished through devices known as ventricular shunts. These surgically implanted devices consist of a catheter draining from the ventricle to a distal site (such as the peritoneum, pleural cavity, or right atrium of the heart) and regulated by a valve. Unfortunately, shunts have extremely high failure rates; most children undergo 2-3 surgical revisions before adulthood and 30% are expected to have at least 1 revision operation in the first year, with rates approaching 98% by 10 years in some studies.

ShuntCheck® utilizes an ice-pack based thermal cooling system connected to a Windows PC DAQ to address a need for shunt monitoring. That technology, however, is cumbersome and time-consuming. The device's cumbersome, multi-step protocol; equivocal or negative past clinical studies; and need for ice-pack cooling have limited its acceptance. Additionally, patient discomfort due to prolonged skin cooling (detrimental for pediatric diagnostics) and absence of chronic monitoring further limits its diagnostic relevance. Accordingly, there is a need for a wireless noninvasive shunt diagnostic, that is conformable to skin and has epidermal-like mechanical properties.

SUMMARY OF THE INVENTION

The devices presented herein provide a platform for measuring flow in subdermal conduits and are advantageously non-invasive and rapid, while preserving a high level of accuracy. The devices may be conformal to skin and wireless without a need for hard-wire connection to bulky external components, such as controllers, digital monitors and power supplies. In this manner, the device is painless and non-obtrusive to a patient, akin to wearing an adhesive bandage.

One particular application for any of the devices and methods described herein is detection of shunt malfunction, specifically ventricular shunts. Extended use can capture occult malfunction, akin to a holter monitor for cerebrospinal fluid.

Provided herein is a soft, wireless, noninvasive, non-surgical, skin-mounted device for the continuous measurement of fluid flow in a subdermal conduit, such as shunt-based CSF flow. The epidermal device exploits the precise measurement of thermal transport to characterize CSF flow in underlaid shunts. The device platform is ultrathin (<100 µm), soft (70 kPa), flexible resulting in a continuously wearable device mechanically invisible to the wearer. Similar in size to a Band-Aid® adhesive bandage, the device is composed primarily of soft, silicone rubber (no hard edges) and transmits recorded data wirelessly via Bluetooth to a companion mobile app. Patient data and in vitro tests confirm device efficacy in producing clinical-quality data suitable for shunt malfunction diagnostics. To assist in handling durability and device placement, a carrier substrate having an open passage through a central portion of the carrier substrate, may be provided around the active sensors region, where intimate conformal contact is desired. The carrier substrate may have a relatively larger mechanical parameter compared to the substrate that supports the sensors, such as being less flexible, elastic and/or soft, so that the device can be handled in a manner similar to an adhesive bandage (e.g., does not tear during application and use) but without sacrificing conformability and patient comfort.

The devices and methods described herein provide a fundamental platform for measuring flow in a wide range of artificial and natural flow conduits. Examples include, but are not limited to, catheters, stents and blood vessels.

The claims appended herein are specifically incorporated by reference herein and form part of the application.

Provided herein are various conformable devices capable of reliably, accurately, and continuously measuring subdermal fluid flow, including in a conduit. Various active components are supported by a substrate, such as a substrate that is characterized as soft, stretchable and flexible. A thermal actuator, an upstream temperature sensor and a downstream temperature sensor is supported by the substrate. A microprocessor is in electronic communication with the temperature sensors and other relevant components, such as the actuator, to calculate subdermal fluid flow from the measured upstream and downstream temperatures. Such a configuration maximizes patient comfort during use, facilitating long-term monitoring of fluid flow. Any of the devices may be wireless, further facilitating low patient impact monitoring, including without a need for hard-wire connections. In this manner, the patient may even return to home, without adversely impacting monitoring.

To further increase the accuracy and reliability of fluid flow measurement, any of the devices described herein may have additional temperature sensors. The position of those sensors may be described relative to a notional line (e.g., imaginary) line that is formed by drawing a line over spatially aligned upstream sensor, actuator, and downstream sensor. The additional sensors function as reference sensors and assist with determining various skin properties and related convection-type properties, for example, useful in determining fluid flow rate and the effect of the actuator independent of flow. Preferably, at least one sensor is positioned so that a temperature reading is obtained that is independent of whether or not the thermal actuator is actuated.

Also provided is a method of determining fluid flow in a sub-dermal conduit by any of the devices described herein. For example, a device is conformally mounted to skin that overlays the sub-dermal conduit. The thermal actuator is actuated to heat the underlying skin and sub-dermal conduit. Temperature upstream and downstream of the thermal actuator is measured wherein the sensors measuring the temperature are spatially aligned with the conduit. The microprocessor processes the measured temperatures to determine a flow-rate in the sub-dermal conduit. The determined flow-rate is transmitted to a display on a handheld device or computer. Preferably the method is wireless and data generated from the conformal device is wirelessly provided to the handheld device or computer for real-time monitoring.

Further, described herein are resistive heating thermal actuators utilizing an array of resistor components that provide heating upon application of an electrical current or potential. These thermal actuators may utilize various resistors known in the art, in some cases arranged in an array (e.g. circular, square, linear) to precisely provide thermal energy to allow for various measurements provided herein.

Additionally, various methods for increasing the signal to noise ratio of thermal measurements are also provided. For example, additional layers that partially or fully encapsulate and insulate various components may enhance the ability to isolate thermal energy provided by the various actuation means and increase the accuracy and reliability of sensing. Conductive layers may also be provided to increase the efficacy of thermal actuation and thermal sensing by providing a conduit for thermal energy to be directed to or received from the skin. Various discontinuous thermal conductive layers may further increase the signal to noise ratio for a variety of measurements, including thermal sensing.

Also described herein are non-electronic methods for thermal sensing. For example, optical measurements via a thermal imaging system or thermochromatic dyes may be utilized in place of electronic thermal sensors to determine tissue characteristic or parameters, including subdermal fluid flow.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE DRAWINGS

FIGS. 1A-1E. Soft, skin-mounted wearable device for noninvasive, continuous, or intermittent measurement of flow through cerebrospinal shunts for evaluation of shunt functioning. FIG. 1A. Exploded view illustration of 100-sensor device that incorporates a central thermal actuator, placed over skin with an underlying shunt catheter ("conduit"). PI=polyimide FIG. 1B. Optical micrograph of device, illustrating sensors, including a plurality a plurality of individual resistive sensors arranged in an array, and central thermal actuator. The close up panels illustrate the stretchable, serpentine interconnects to facilitate conformability and individual resistive temperature sensors. FIG. 1C. Infrared (IR) thermographs illustrating addressing of an individual sensor (left), and thermal actuation from central heater with 1.8 mW/mm$^2$ actuation power. FIG. 1D. Optical images of device on neck, over location of shunt, under different deformation modes. FIG. 1E. IR thermographs with color and contrast enhancement showing thermal isotropy in the absence of flow (top) and anisotropy in the presence of flow (bottom), with flow going towards the right of the page.

FIGS. 2A-2E. Flow visualization and measurement from ESA (epidermal square array). FIG. 2A. Spatially precise schematic map of 100 sensor device with tube position overlay and upstream ($T_u$) and downstream ($T_d$) temperatures shown. FIG. 2B. Baseline-subtracted temperature differentials of 4 sensor pairs as shown by the color coding in FIG. 2A. FIG. 2C. Principal components analysis (PCA) biplot (principle component 1 and 2) of baseline-subtracted differentials between a selected $T_u$ sensor (two sensors, each indicated in subfigure) and each $T_d$ sensor. Clustering occurs for the following cases: no flow and no actuation; no flow with actuation at 1.8 mW/mm$^{-2}$; Actuation at 1.8 mW mm$^{-2}$ and flow at 0.02 mL min$^{-1}$; Actuation at 1.8 mW/mm$^2$ and flow at 2 mL min$^{-1}$. Vectors correspond to selected $T_d$ sensors correlated positively (red) and negatively (blue) with flow. FIG. 2D. Flow chart detailing the process of transforming raw ESA sensor data to spatially precise temperature maps. FIG. 2E. Thermographs from IR imaging (top) and ESA-generated temperature maps (bottom), in the absence (left) and presence (right) of 0.02 mL min$^{-1}$ flow (flow from right to left) with actuation at 1.8 mW/mm$^{-2}$.

FIGS. 3A-3L. Systemic characterization of effects of geometry, thermal properties, flow rates. FIG. 3A. Optical image of epidermal linear array (ELA) overlaid with illustration of catheter and blood vessel (top) and schematic illustration of benchtop system illustrating key features, including thermal properties of skin phantom, blood flow ($Q_{blood}$), CSF flow ($Q_{flow}$) and skin thickness ($h_{skin}$). FIG. 3B. Raw transient temperature data after the onset of heating for actuator (blue curve), downstream sensor (black curve) and upstream sensor (red curve) under 4 values of $Q_{flow}$–0 mL min$^{-1}$ (unshaded region), 0.05 ml min$^{-1}$ (blue shaded region), 0.1 mL min$^{-1}$ (gray shaded region) and 0.5 ml min$^{-1}$ (red shaded region). FIG. 3C. $T_{sensors}/T_{actuator}$ for upstream (red) and downstream (black) sensors across a range of flow rates from 0.01 ml min$^{-1}$ to 0.1 mL min$^{-1}$. FIG. 3D. $\Delta T_{sensors}/T_{actuator}=(T_{downstream}-T_{upstream})/T_{actuator}$ for a range of $Q_{flow}$ from 0.01 ml min to 0.1 ml min for three anatomically relevant values of $h_{skin}$, 1.1 mm (black curve), 1.7 mm (red curve) and 2.1 mm (blue curve). FIG. 3E. $\overline{T}_{sensors}=(T_{downstream}+T_{upstream})/2T_{actuator}$ for the same $Q_{flow}$ and $h_{skin}$ values as FIG. 3D. FIG. 3F. Ratio between signal ($\Delta T_{sensors}/T_{actuator}$) and noise (standard deviation, $\sigma$) measured for $Q_{flow}$=0.1 mL min over a 60 s sampling window, at a sampling frequency of 5 Hz, as a function of normalized actuator power for three different values of $h_{skin}$, 1.1 mm (black curve), 1.7 mm (red curve) and 2.1 mm (blue curve). FIGS. 3G and 3E. ($\Delta T_{sensors}/T_{actuator}$) (FIG. 3G) and ($T_{downstream}$+$T_{upstream}$)/2$T_{actuator}$ (FIG. 3E) measured in the presence of phantom blood flowing through adjacent tubes in co-flow (+x) and counter-flow (−x) configurations, for two values of $h_{skin}$, 1.1 mm (black curve) and 2.1 mm (blue curve). FIG. 3H is a plot of the ratio of sensor to actuator temperature as a function of blood flow. FIG. 3I. Experimental data (solid lines) and analytical fits (dashed lines) for $T_{actuator}$ as a function of time for $Q_{flow}$=0 for two different skin phantoms, Sylgard 184 (black curve) and Syl 170 (gray curve) to simulate and measure skin thermal properties. FIGS. 3J-3K. $\Delta T_{sensors}/T_{actuator}$) (FIG. 3J) and ($T_{downstream}$+$T_{upstream}$)/2$T_{actuator}$ (FIG. 3K) measured for the two skin phantom materials. FIG. 3L In vitro experimental measurements of $\Delta T_{sensors}/T_{actuator}$ for $h_{skin}$ (1.1, 1.7, 2.1, and 6.0 mm for four flowrates) and for $Q_{flow}$ (0 ml/min (black curve), 0.05 ml/min (red curve), 0.1 ml/min (blue curve), and 0.5 ml/min (purple curve)).

FIG. 4A-4H. Wireless device, including Bluetooth communication with a portable device. FIG. 4B is an image of a fully assembled, integrated wireless ELA showing soft, conformal sensing/actuating components, flex-PCB (Cu/PI/Cu), and surface-mounted electronic components, including battery and wireless communication components. PDMS, polydimethylsiloxane. FIG. 4C is an image of device bending, showing flexibility. FIG. 4D is an image of a device mounted on the skin using medical-grade, acrylate-based pressure-sensitive adhesive. FIG. 4E. Raw sensor readout in measured bits from an 8-bit ADC during actuation and flow. FIG. 4F. IR-measured temperature rise due to 3.6-mW actuation on the phantom shunt assembly. FIG. 4G Calibration curve to measure raw 8-bit, 3-V ADC values (left) and associated voltages (right) to temperatures via calibration. FIG. 4H. Difference in $T_{upstream}$ and $T_{downstream}$ acquired wirelessly as a function of time for two different flows, Q=0.05 mL/min and Q=0.13 mL/min. All data are collected on a skin phantom.

FIG. 5A. Exploded view illustration of ELA used in hospital setting, with elastomeric handling frame and adhesive. FIG. 5B. Illustration (left) and image (right) of on-shunt and off shunt ELA positioning on patient, with representative Doppler ultrasound image (inset) of catheter under skin at on-shunt location. FIG. 5C. IR images at on-shunt (top) and off shunt (bottom) indicating total local temperature rise due to actuator, and characteristic tear-drop shaped heat distribution caused by presence of flow. FIG. 5D. Representative transient $T_{actuator}$ measurement on off-shunt location, and transient plane source (TPS) curve fit to yield skin thermal properties. FIGS. 5E-5F. Computed values of $k_{skin}$ (FIG. 5E) and $\alpha_{skin}$ (FIG. 5F) for each patient. FIGS. 5G-5H. Representative $T_{actuator}$ (blue curve), $T_{upstream}$ (black curve) and $T_{downstream}$ (red curve) for off-shunt location with no anisotropy (FIG. 5G) and on-shunt location with significant anisotropy (FIG. 5H). FIG. 5I. $\Delta T_{sensors}/T_{actuator}$ measured for each patient, at off-shunt and on-shunt locations, with error bars representing SDs across a 100-sample window. FIG. 5J is a plot of the computed mean of $\Delta T_{sensors}/\Delta T_{actuator}$ on n=5 patients with clinically or surgically confirmed flow on off-shunt and on-shunt locations, with error bars representing SD. Statistical analysis was performed using a paired t test (n=5) for cases with confirmed flow over on-shunt and off-shunt locations. Individual patient-level data are summarized as Patient # ($\Delta T_{sensors}/T_{acuator}$ On Shunt and $\Delta T_{sensors}/T_{acuator}$ Off Shunt): Patient 1 (0.209339 and 0.00205); Patient 2 (0.0518 and 0.0084); Patient 3 (0.09503 and −0.00597); Patient 4 (0.100991 and 0.0061); Patient 5 (0.1392 and 0.000963).

FIGS. 6A-6D. Case study of patient with shunt malfunction. FIG. 6A. X-Ray and radionuclide tracer showing kinking and occlusion of catheter. FIG. 6B. Optical image of patient's peritoneal cavity immediately after surgery showing flow in repaired shunt. FIG. 6C. X-ray and radionuclide tracer confirming working of repaired shunt. FIG. 6D. $\Delta T_{sensors}/T_{actuator}$ measured by ELA before and after revision, at locations over (on) and adjacent to (off) shunt, before and after revision, confirming results from X-Ray and Radionuclide tracer.

FIG. 7A. FEA-computed family of curves for different skin thicknesses of $\Delta T_{sensors}/T_{actuator}$ with data measured in-vivo from each patient overlaid. FIG. 7B. Computed curves for $\overline{T}_{sensors}/T_{actuator}$ for different skin thicknesses. FIG. 7C. Computed flow rates from iteratively solving for both $\Delta T_{sensors}/\Delta T_{actuator}$ and $\overline{T}_{sensors}/T_{actuator}$ with error bars representing average differences in the individual values yielded by the two curves. FIG. 7D. FEA-computed values of $\Delta T_{sensors}/\Delta T_{actuator}$ and $\overline{T}_{sensors}/T_{actuator}$ using values of $h_{skin}$=1.5 mm (acquired from CT imaging) and $k_{skin}$=0.29 W m$^{-1}$ K$^{-1}$ and $\alpha$skin=0.091 mm$^2$ s$^{-1}$ acquired in vivo from a patient as shown previously, overlaid with experimentally measured points from the same patient, yielding a flow rate of 0.1 mL/min.

FIGS. 8A-8B. Current pathways through resistive arrays. FIG. 8A. IR image (top) and simulations of ESA with single sensor addressed, showing currents through same input line (row) and output line (column). FIG. 8B. Same as FIG. 8A, but for a non-square array (16×6), showing large power dissipation through non-addressed sensors in same output line (spoke).

FIG. 12A: Spatially precise schematic map of 100 sensor device with tube position overlay and upstream (U) and downstream (D) temperatures shown. FIG. 12B: Principal components analysis (PCA) biplot (principle component 1 and 2) of baseline-subtracted differentials between a selected U sensor (two sensors, each indicated in subfigure) and each D sensor. Clustering occurs for the following cases: no flow and no actuation; no flow with actuation at 1.8 mW/mm$^{-2}$; Actuation at 1.8 mWmm$^{-2}$ and flow at 0.02 mL min$^{-1}$. FIG. 12C. PCA biplots for five (1-5) sensors (identified in FIG. 12A) illustrating the identification of the sensors aligned with the flow direction regardless of selected sensor (red vector). When a PCA model is applied to the aligned data (used to generate temperature maps), PC1 correlates to presence/absence of flow and PC2 corresponds to thermal actuation state (on/off).

FIG. 13A. Optical image of benchtop flow phantom with embedded shunt. FIG. 13B. Optical micrograph of cross section and isometric views showing catheter geometry and $h_{skin}$. FIG. 13C. Sensor laminated onto the free surface of the assembly.

FIG. 17. Illustration of covered and uncovered (encapsulated) actuator measurements (left) to yield transient rise curves for fitting the value of $H_{conv}$ (right).

FIGS. 18A-18C. FIG. 18A. Illustration and experimental data showing the effect of (FIG. 18B) rotational and (FIG. 18C) translational mispositioning on measured values of $\Delta T_{sensors}/T_{actuator}$ (black curve) and $T_{sensors}/T_{actuator}$ (red curve).

FIGS. 19A-19F. DC Noise sources. FIG. 19A. Simplified schematic of data acquisition system for ELA. FIG. 19B. Standard deviations as a function of sampling window for resistances measured by ELA (black), a commercial sensor connected via ACF cable (blue) and a commercial resistor connected via soldered lead wires (red). FIG. 19C. Standard deviation as a function of sampling window for actuator output power. FIG. 19D. Standard deviation for measured $\Delta T_{sensors}/T_{actuator}$ as a function of sampling window for $Q_{flow}=0.13$ mL min$^{-1}$ on benchtop system, when covered by an enclosure (black) and uncovered (red). FIG. 19E. High Frequency Noise. Panel A. Schematic illustration of experimental system. Panel B. Fourier transform of resistance measured at 20 kHz. Panel C. S/N, computed as the average of 5 successive resistance measurements divided by their standard deviation as a function of number of samples (N) and sampling window (time, ns). Panel D. Experimental data and linear fit for S/N as a function of N. FIG. 19F. S15. In-vivo noise A. Optical images illustrating no deformation (left) and extreme deformation (right) of sensor on skin. B-D. Temperature fluctuations measured as a function of time (B), frequency (C) and as a normalized power spectral density (D) on a stationary subject. E-G Same as B-D on a vigorously moving subject.

FIG. 20. Optical images of elastomeric adhesive with tape frame on wrist illustrating conformal contact during extreme deformation.

FIGS. 21A-21B. In-vivo $T_{actuator}$ (blue curve), $T_{upstream}$ (black curve) and $T_{downstream}$ (red curve) measurements as a function of time over on-shunt locations with low anisotropy (FIG. 21A) and after stimulating flow by pressing the regulating valve (FIG. 21B).

FIG. 22. $T_{actuator}$ measurements on external ventricular drain as flow is varied by raising height of reservoir bag (not shown), thereby changing differential pressure.

FIG. 27. Skin-safe, silicone adhesive, with active sensing portion of device able to maintain conformal contact with skin, with delamination confined to edge handling substrate that surrounds the active sensing portion.

FIG. 32. provides an analog design of circuits described herein.

FIG. 33. illustrates the use of thermochromatic dyes arranged in an array to determine subdermal fluid flow.

FIG. 34. provides an example of a thermal imaging approach and currently available inexpensive thermal imaging devices.

FIG. 48. provides an example of a clinical protocol that may be useful to ensure accurate application of the devices described herein.

Figure 49:
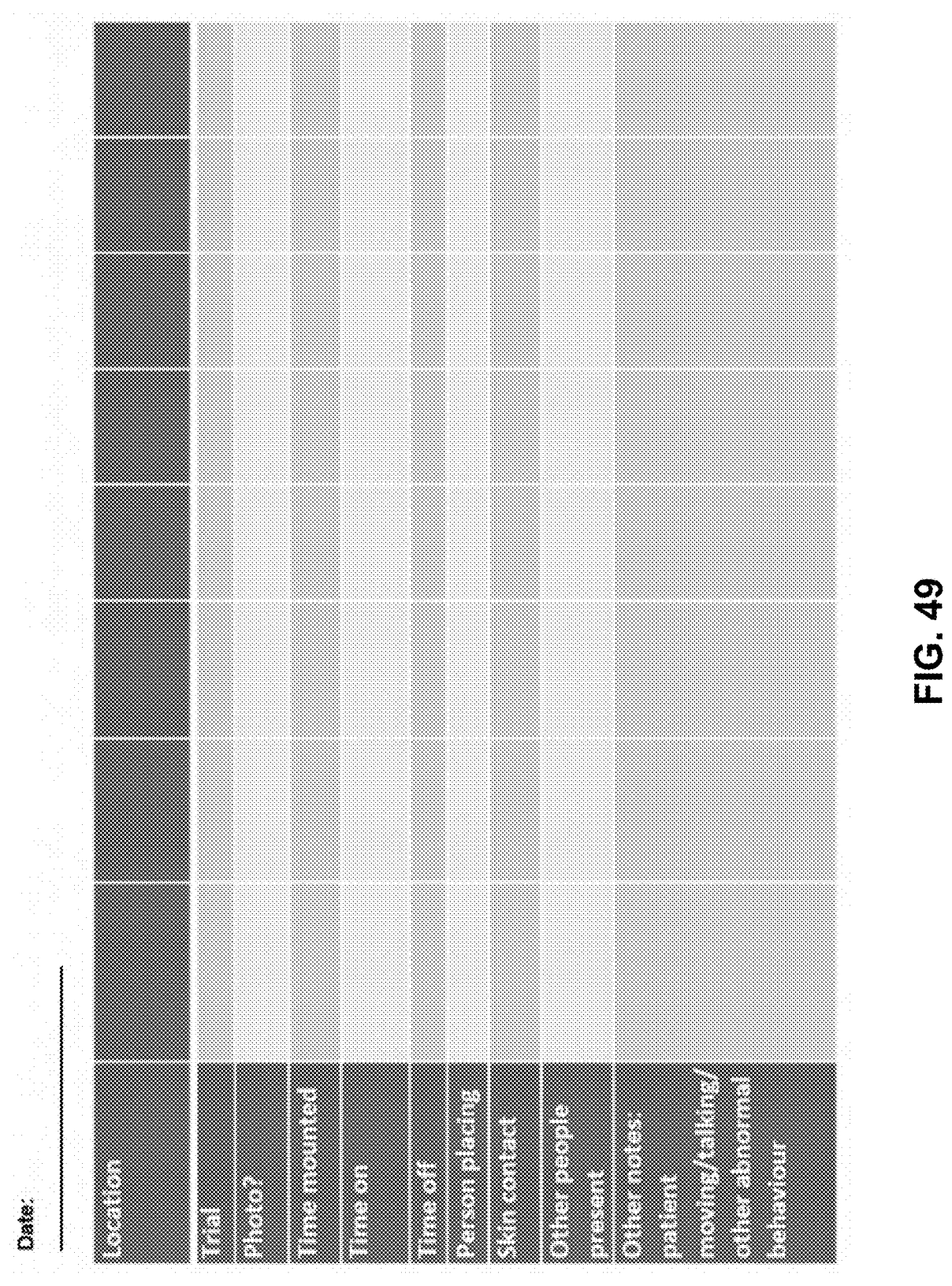

FIG. 49. provides an example of a clinical checklist that may be useful to ensure accurate application of the devices described herein.

FIG. 52A is a schematic illustration showing positions of actuator and upstream and downstream temperature sensors relative to underlying catheter. FIG. 52B FEA simulation of $\Delta T_{sensors}/T_{actuator}$ as a function of L, for $h_{skin}$=0.5 mm, 1.0 mm, 1.5 mm, 2.0 mm, with the effect of 15% strain resulting in an altered inter-sensor positional uncertainty of ±0.375 mm, as shown by the rectangular bar. FIG. 52C FEA simulation of $T_{sensors}/T_{actuator}$ as a function of L, for $h_{skin}$=0.5 mm, 1.0 mm, 1.5 mm, 2.0 mm, with the effect of 15% strain resulting in an altered inter-sensor positional uncertainty of ±0.375 mm, as shown by the rectangular bar.

FIGS. 53A-53D. Miniaturized, soft wireless flow sensor based on commercial components. FIG. 53A. Exploded view schematic of key device layers. FIG. 53B. Optical images of packaged, encapsulated device twisting and bending. FIG. 53C. Optical image of device mounted on neck of patient. FIG. 53D. Screenshot of software application on tablet computer showing data readout, pairing and options for on-demand thermal actuation.

FIG. 54A. Exploded view schematic of sensors and actuators with overlaid foam layer over shunt embedded in silicone skin phantom. FIG. 54B. Infrared (IR) thermograph of actuator dissipating thermal power at 1.2 mW/mm². FIG. 54C. Upstream (gray) and downstream (red) temperature readout after actuation, and after during flow respectively, showing the bifurcation of the traces ($\Delta T$) and the reduced overall average temperature ($T_{avg}$), respectively, after the onset of flow. FIG. 54D. $\Delta T$ as a function of time before and after the onset of flow. FIG. 54E. $\Delta T$ as a function of flow rate for a range of physiologically relevant skin thicknesses, from 0.7 mm to 4 mm. FIG. 54F. $T_{avg}$ as a function of flow rate for a range of physiologically relevant skin thicknesses.

FIG. 55A. Optical image of wireless sensor over shunt on representative patient, without smartphone readout. FIG. 55B. AT for cases with confirmed flow, no flow/irregular flow and off shunt locations, with error bars representing S.D.

FIG. 66. Representative clinical images of a device positioned on and off shunt.

DETAILED DESCRIPTION OF THE INVENTION

Figures 1A, 1B:
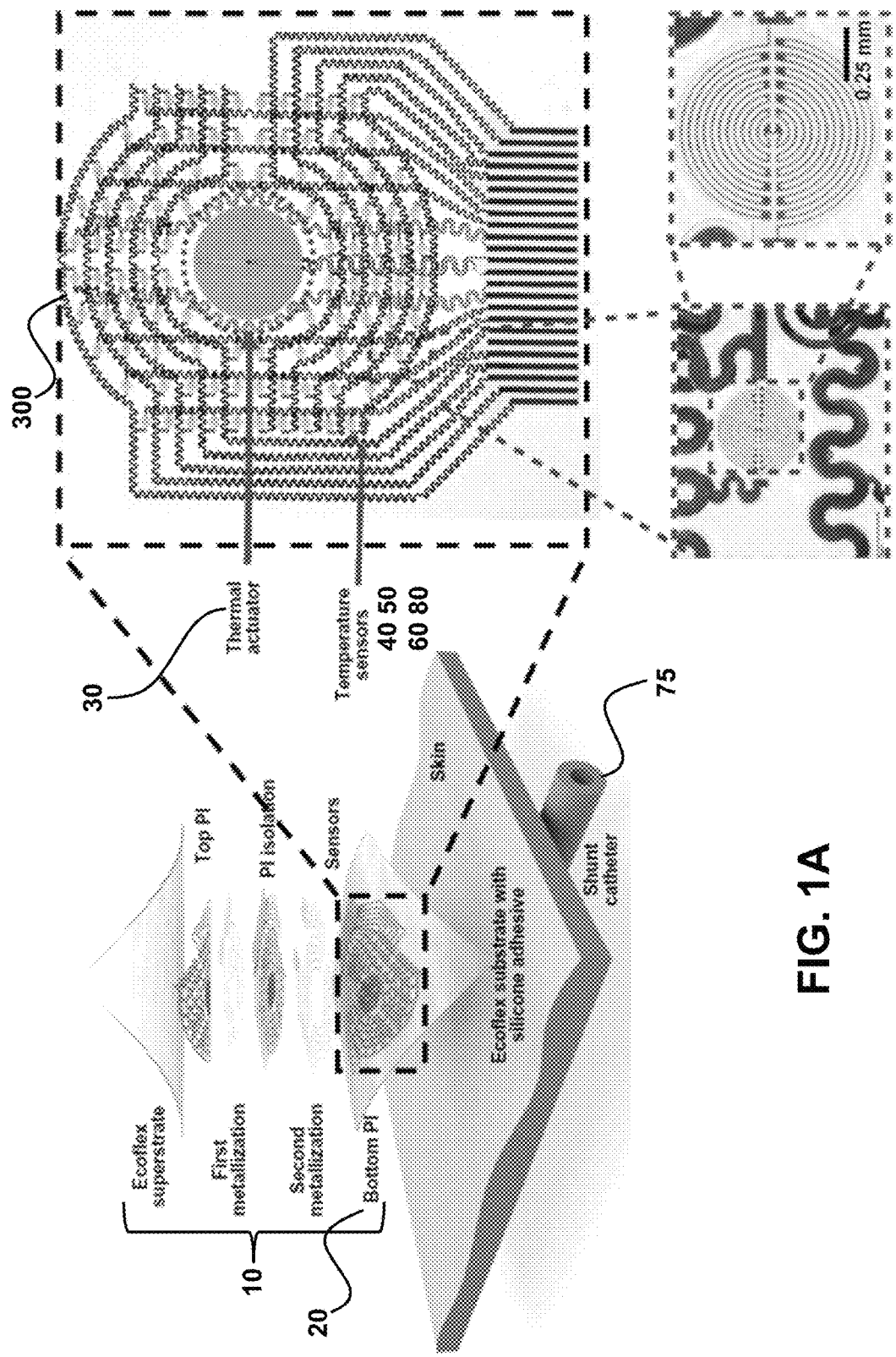

In general, the terms and phrases used herein have their art-recognized meaning, which can be found by reference to standard texts, journal references and contexts known to those skilled in the art. The following definitions are provided to clarify their specific use in the context of the invention.

"Soft" refers to a material that may be comfortably positioned against the skin without discomfort or irritation to the underlying skin by the material itself deforming to conform to the skin without unduly exerting force on the underlying skin with corresponding device-generated skin deformation. Softness/hardness may be optionally quantified, such as in terms of durometer, or a material's resistance to deformation. For example, the substrate may be characterized in terms of a Shore 00 hardness scale, such as a Shore 00 that is less than 80. Soft may also be characterized in terms of a modulus, such as a Young's modulus that is less than or equal to 100 kPa.

"Stretchable" refers to a material's ability to undergo reversible deformation under an applied strain. This may be characterized by a Young's modulus (stress/strain). A bulk or effective Young's modulus refers to a composite material formed from materials having different Young's modulus, so that the bulk or effective Young's modulus is influenced by each of the different materials and provides an overall device-level modulus.

"Flexible" refers to a material's ability to undergo a bending with fracture or permanent deformation, and may be described in terms of a bending modulus.

Any of the devices may be described herein as being "mechanically matched" to skin, specifically the skin over which the device will rest. This matching of device to skin refers to a conformable interface, for example, useful for establishing conformal contact with the surface of the tissue. Devices and methods may incorporate mechanically functional substrates comprising soft materials, for example exhibiting flexibility and/or stretchability, such as polymeric and/or elastomeric materials. A mechanically matched substrate may have a modulus less than or equal to 100 MPa, less than or equal to 10 MPa, less than or equal to 1 MPa. A mechanically matched substrate may have a thickness less than or equal to 0.5 mm, and optionally for some embodiments, less than or equal to 1 cm, and optionally for some embodiments, less than or equal to 3 mm. A mechanically matched substrate may have a bending stiffness less than or equal to 1 nN m, optionally less than or equal to 0.5 nN m.

A mechanically matched device, and more particularly a substrate is characterized by one or more mechanical properties and/or physical properties that are within a specified factor of the same parameter for an epidermal layer of the skin, such as a factor of 10 or a factor of 2. For example, a substrate may have a Young's Modulus or thickness that is within a factor of 20, or optionally for some applications within a factor of 10, or optionally for some applications within a factor of 2, of a tissue, such as an epidermal layer of the skin, at the interface with a device of the present invention. A mechanically matched substrate may have a mass or modulus that is equal to or lower than that of skin.

"Encapsulate" refers to the orientation of one structure such that it is at least partially, and in some cases completely, surrounded by one or more other structures, such as a substrate, adhesive layer or encapsulating layer. "Partially encapsulated" refers to the orientation of one structure such that it is partially surrounded by one or more other structures, for example, wherein 30%, or optionally 50%, or optionally 90% of the external surface of the structure is surrounded by one or more structures. "Completely encapsulated" refers to the orientation of one structure such that it is completely surrounded by one or more other structures.

"Polymer" refers to a macromolecule composed of repeating structural units connected by covalent chemical bonds or the polymerization product of one or more monomers, often characterized by a high molecular weight. The term polymer includes homopolymers, or polymers consisting essentially of a single repeating monomer subunit. The term polymer also includes copolymers, or polymers consisting essentially of two or more monomer subunits, such as random, block, alternating, segmented, grafted, tapered and other copolymers. Useful polymers include organic polymers or inorganic polymers that may be in amorphous, semi-amorphous, crystalline or partially crystalline states. Crosslinked polymers having linked monomer chains are particularly useful for some applications. Polymers useable in the methods, devices and components disclosed include, but are not limited to, plastics, elastomers, thermoplastic elastomers, elastoplastics, thermoplastics and acrylates. Exemplary polymers include, but are not limited to, acetal polymers, biodegradable polymers, cellulosic polymers, fluoropolymers, nylons, polyacrylonitrile polymers, polyamide-imide polymers, polyimides, polyarylates, polybenzimidazole, polybutylene, polycarbonate, polyesters, polyetherimide, polyethylene, polyethylene copolymers and modified polyethylenes, polyketones, poly(methyl methacrylate), polymethylpentene, polyphenylene oxides and polyphenylene sulfides, polyphthalamide, polypropylene, polyurethanes, styrenic resins, sulfone-based resins, vinyl-based resins, rubber (including natural rubber, styrene-butadiene, polybutadiene, neoprene, ethylene-propylene, butyl, nitrile, silicones), acrylic, nylon, polycarbonate, polyester, polyethylene, polypropylene, polystyrene, polyvinyl chloride, polyolefin or any combinations of these.

"Elastomer" refers to a polymeric material which can be stretched or deformed and returned to its original shape without substantial permanent deformation. Elastomers commonly undergo substantially elastic deformations. Useful elastomers include those comprising polymers, copolymers, composite materials or mixtures of polymers and copolymers. Elastomeric layer refers to a layer comprising at least one elastomer. Elastomeric layers may also include dopants and other non-elastomeric materials. Useful elastomers include, but are not limited to, thermoplastic elastomers, styrenic materials, olefinic materials, polyolefin, polyurethane thermoplastic elastomers, polyamides, synthetic rubbers, PDMS, polybutadiene, polyisobutylene, poly(styrene-butadiene-styrene), polyurethanes, polychloroprene and silicones. Exemplary elastomers include, but are not limited to silicon containing polymers such as polysiloxanes including poly(dimethyl siloxane) (i.e. PDMS and h-PDMS), poly(methyl siloxane), partially alkylated poly(methyl siloxane), poly(alkyl methyl siloxane) and poly(phenyl methyl siloxane), silicon modified elastomers, thermoplastic elastomers, styrenic materials, olefinic materials, polyolefin, polyurethane thermoplastic elastomers, polyamides, synthetic rubbers, polyisobutylene, poly(styrene-butadiene-styrene), polyurethanes, polychloroprene and silicones. In an embodiment, a polymer is an elastomer.

"Conformable" refers to a device, material or substrate which has a bending stiffness that is sufficiently low to allow the device, material or substrate to adopt any desired contour profile, for example a contour profile allowing for conformal contact with a surface having a pattern of relief features. In certain embodiments, a desired contour profile is that of skin.

"Conformal contact" refers to contact established between a device and a receiving surface, specifically skin. In one aspect, conformal contact involves a macroscopic adaptation of one or more surfaces (e.g., contact surfaces) of a device to the overall shape of a surface. In another aspect, conformal contact involves a microscopic adaptation of one or more surfaces (e.g., contact surfaces) of a device to a surface resulting in an intimate contact substantially free of voids. In an embodiment, conformal contact involves adaptation of a contact surface(s) of the device to a receiving surface(s) such that intimate contact is achieved, for example, wherein less than 20% of the surface area of a contact surface of the device does not physically contact the receiving surface, or optionally less than 10% of a contact surface of the device does not physically contact the receiving surface, or optionally less than 5% of a contact surface of the device does not physically contact the receiving surface. Devices of certain aspects are capable of establishing conformal contact with internal and external tissue. Devices of certain aspects are capable of establishing conformal contact with tissue surfaces characterized by a range of surface morphologies including planar, curved, contoured, macro-featured and micro-featured surfaces and any combination of these. Devices of certain aspects are capable of establishing conformal contact with tissue surfaces corresponding to tissue undergoing movement.

"Young's modulus" is a mechanical property of a material, device or layer which refers to the ratio of stress to strain for a given substance. Young's modulus may be provided by the expression:

$$E = \frac{(\text{stress})}{(\text{strain})} = \left(\frac{L_0}{\Delta L}\right)\left(\frac{F}{A}\right), \quad (I)$$

where E is Young's modulus, $L_0$ is the equilibrium length, $\Delta L$ is the length change under the applied stress, F is the force applied, and A is the area over which the force is applied. Young's modulus may also be expressed in terms of Lame constants via the equation:

$$E = \frac{\mu(3\lambda + 2\mu)}{\lambda + \mu}, \quad (II)$$

where $\lambda$ and $\mu$ are Lame constants.

"Low modulus" refers to materials having a Young's modulus less than or equal to 10 MPa, less than or equal to 5 MPa or less than or equal to 1 MPa.

"Bending stiffness" is a mechanical property of a material, device or layer describing the resistance of the material, device or layer to an applied bending moment. Generally, bending stiffness is defined as the product of the modulus and area moment of inertia of the material, device or layer. A material having an inhomogeneous bending stiffness may optionally be described in terms of a "bulk" or "average" bending stiffness for the entire layer of material.

"Thermal actuation state" refers to the thermal actuator that is on an off-state or an on-state. In this context, "substantially independent" refers to a position of the reference sensor that is sufficiently separated from the actuator that the reference sensor output is independent of whether the thermal actuator is on or off. Of course, the systems and methods presented herein are compatible with relatively minor effects of the actuator on the reference sensor, such as within 5%, within 1% or within 0.1% of a reference temperature when the actuator is in the on state compared to when the actuator is in the off state. Depending on specific device and tissue characteristics, this distance may be between about 10 mm and 20 mm, such as about 15 mm.

Figure 67:
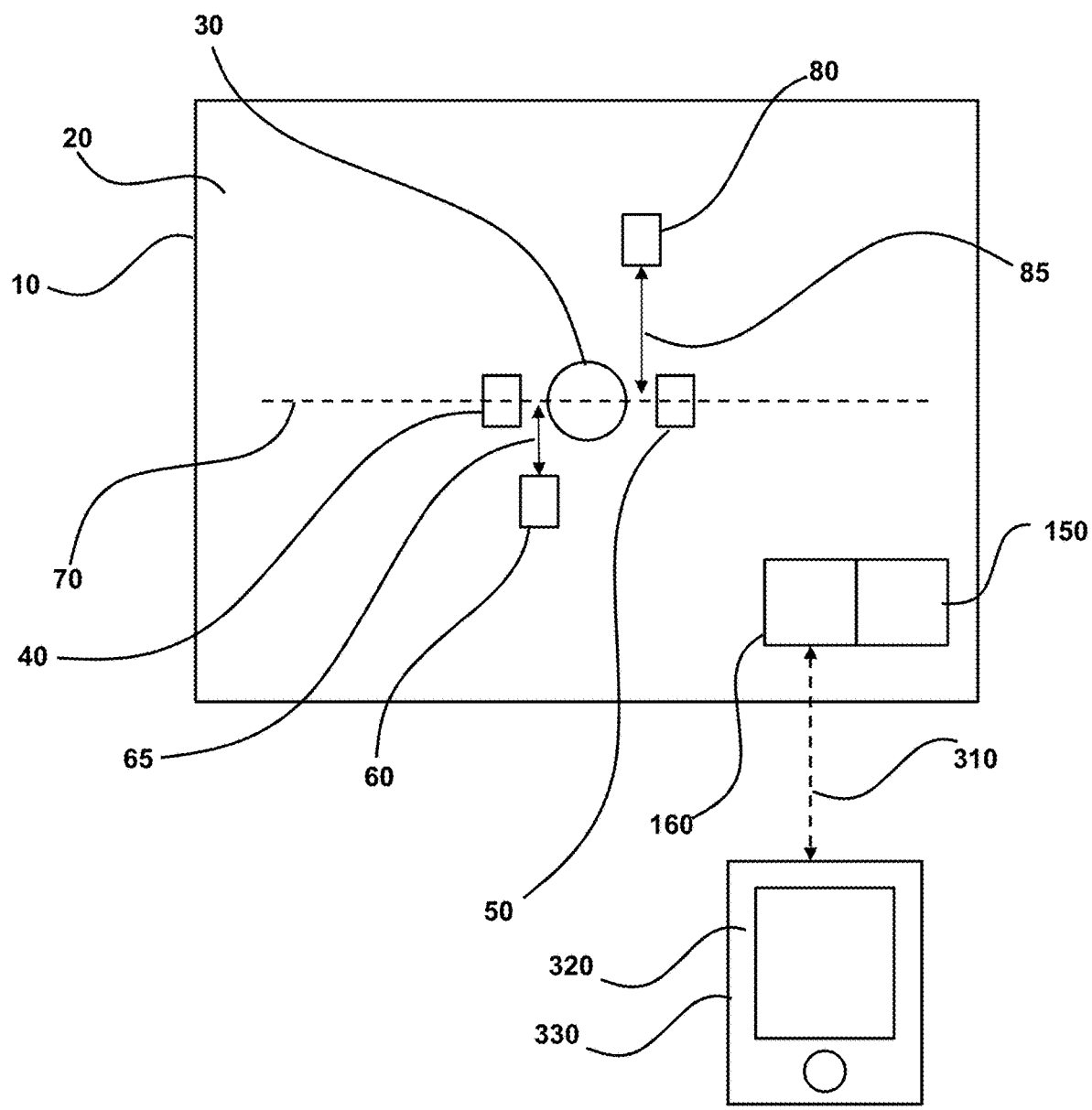
FIG. 67. Schematic illustration of a device.

Referring to the figures provided herein, a conformable device 10 to measure subdermal fluid flow, including in a conduit 75 such as a shunt or a blood vessel, may comprise a substrate 20 that supports upstream 30 and downstream 40 temperature sensors. Upstream and downstream are described relative to flow direction in the fluid conduit. The temperature sensors may be part of an array of temperature sensors, including a high density array 300 as shown in FIG. 1A-1B. Within that array, are any number of reference sensors used to assess one or more baseline skin properties, including an actuator reference sensor 60 and/or ambient reference sensor 80. As explained herein, the reference sensor locations may be determined to be those that are independent of thermal actuation status (e.g., ambient reference sensor) or of flow status in the conduit (e.g., actuator reference sensor). The reference sensor locations may be characterized in terms of a separation distance (65 85) from notional line 70 that is a straight line connection between the upstream and downstream temperature sensors and the thermal actuator to the reference sensors (60 80) (FIG. 67).

Figure 4B:
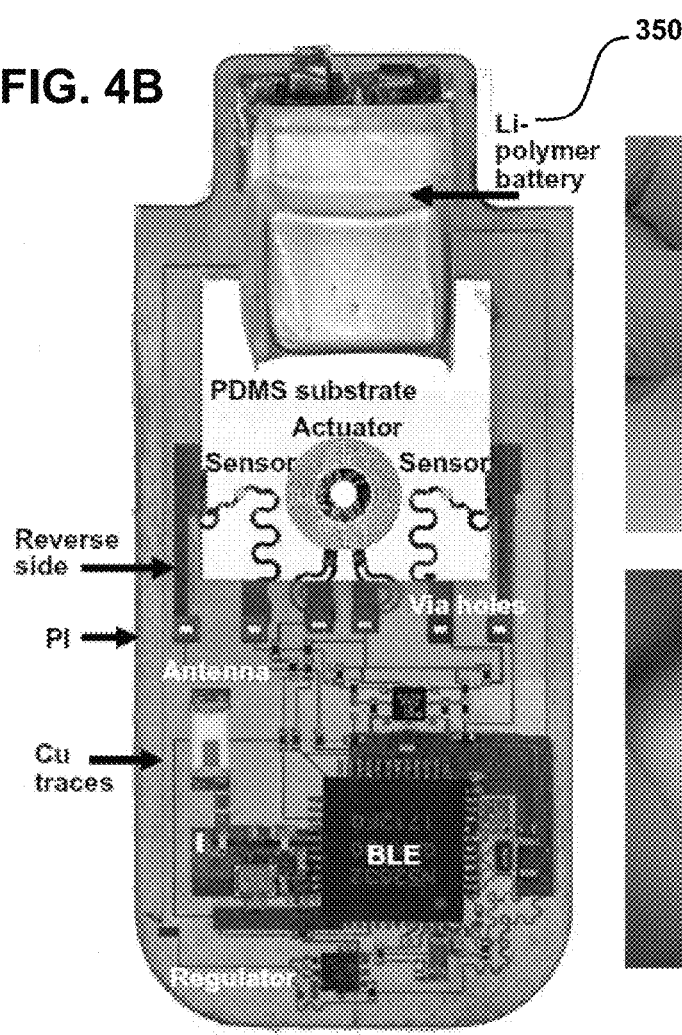
Figure 4C:
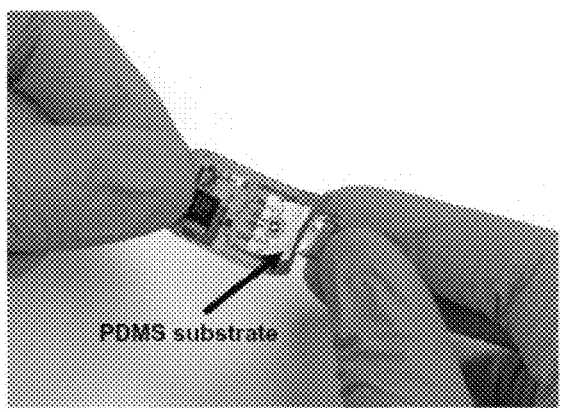
Figure 4D:
Figure 4E:
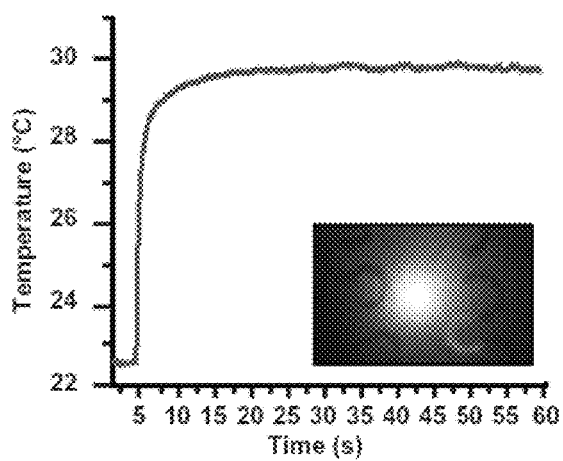
Figure 4F:
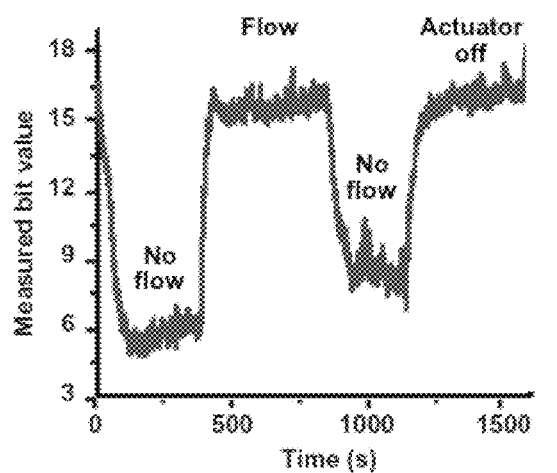
Figure 4G:
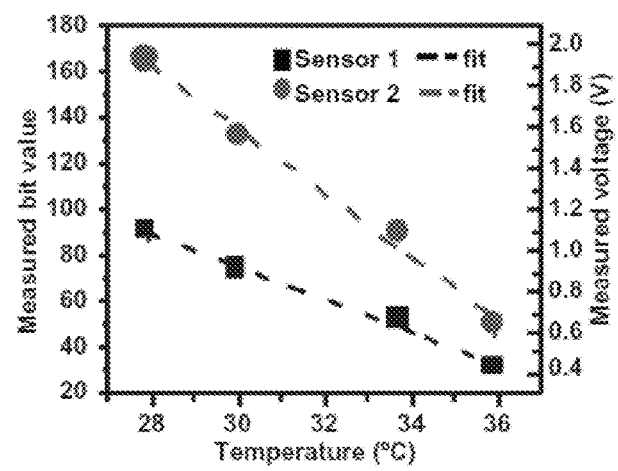
Figure 4H:
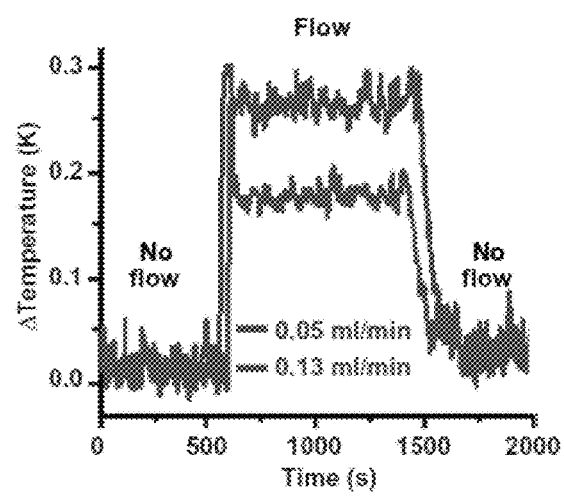
Figure 58:
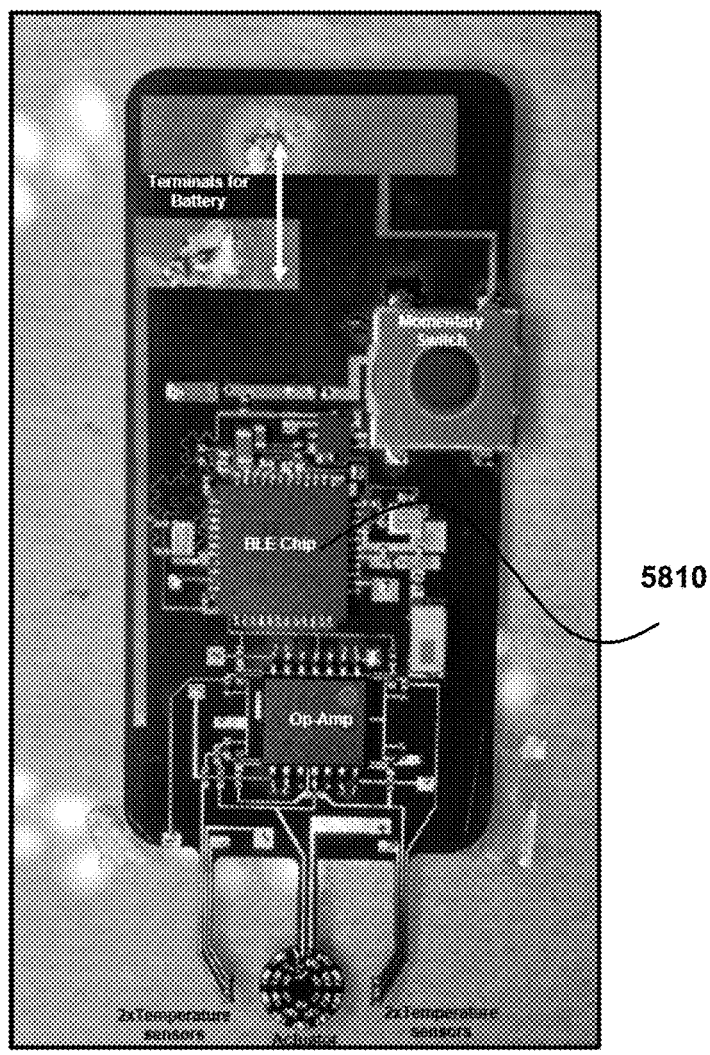
FIG. 58. Unpackaged circuit layout providing various electronic components on-board the device, including for power, wireless communication and circuitry to control and measure.

A microprocessor 160 (illustrated as on-board device 10 in FIG. 67, but may be positioned remotely), may be wirelessly connected via one or more wireless communication components 310 to the temperature sensors and/or to connect the device 10 to a microcontroller 320 illustrated as within a hand-held or computer 330 remote device. As desired, a power source 150 (also illustrated as 350 in FIG. 4B) may be connected on-board device 10. Optionally, the power source may correspond to wirelessly charging components. Wireless communication components 5810 are also illustrated in FIG. 58 (see also antenna of FIG. 4B).

As desired, the device may be covered with an encapsulation layer 1700 (FIG. 17), including a foam layer or an additional partial layer formed of foam on top of the encapsulating layer (also referred herein as a superstrate—see, e.g., FIG. 53A) positioned to vertically cover the temperature actuator and sensors. As the foam layer is demonstrated to improve device performance, any of the devices provided herein may comprise a foam layer positioned over an encapsulation layer, wherein the foam layer may cover the entire encapsulation layer or a portion thereof that corresponds, in a vertical geometrical configuration, to the temperature sensors and actuator to minimize thermal noise and improve device performance and sensitivity.

Figure 46:
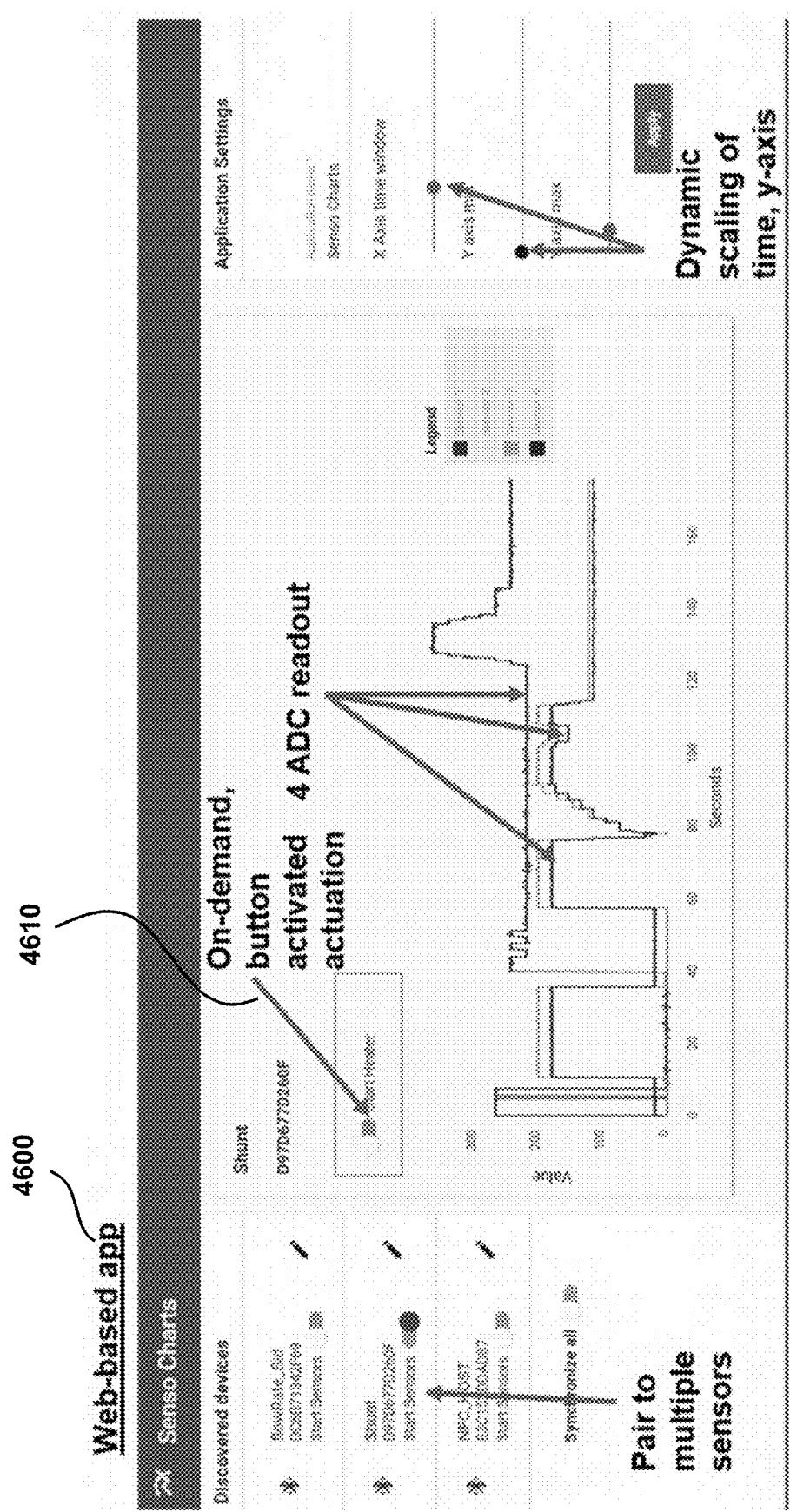
FIG. 46. provides an example software interface.

The devices and methods provided herein are conveniently implementable and manageable, including to a health care provider. For example, FIG. 46 illustrates a device operably integrated or connected to a computer-implemented program or application 4600 having an on-demand actuation 4610 on a handheld. In this manner, individual sensor control, device actuation, and date monitoring is readily, conveniently and reliably available to a medical professional who may be remotely located from a patient who is wearing the device.

Example 1: Epidermal Electronics for the Noninvasive, Wireless, Quantitative Assessment of Ventricular Shunt Function Ventricular shunts represent an essential component of clinical treatment for hydrocephalus, a common and debilitating neurological disorder that results from the overproduction and/or impaired reabsorption of cerebrospinal fluid (CSF) produced in the ventricular system of the brain [Rachel]. Hydrocephalus arises from a number of causes, including but not limited to cancer, hemorrhage, trauma, and congenital malformations. This condition affects an estimated 750,000 patients in the United States alone, and it is responsible for ~3.1% of all pediatric acute care costs [Lam, Patwardhan, Shannon, Stone]. 125,000 pediatric hydrocephalus patients in the US account for 400,000 days spent in the hospital each year [Simon]. Shunts assemblies typically involve two silicone catheters, connected upstream and downstream of a regulating valve, to drain excess CSF from the ventricle to a distal absorptive site, usually the peritoneum, pleura, or right atrium of the heart. While effective in CSF diversion and prevention of the sequelae of hydrocephalus, including seizures, coma, neurological injury and death, shunts are highly prone to failure [Tervonen] due to fibrinous catheter ingrowth, kinking, discontinuity, overdrainage, distal malabsorption and infection [Garton, Yuh]. An estimated 84.5% shunt recipients require revision operations [Cochrane, Shah, Stone, Piatt]. Clinical symptoms of shunt malfunction tend to be non-specific, such as headache, nausea and somnolence, thereby creating challenges in clinical diagnosis [Kirkpatrick, Piatt, Garton]. Because ramifications of misdiagnosis can include severe morbidity and mortality, isolating the location and cause of failure is critical in the appropriate care of hydrocephalic patients.

Diagnostic tests to assess shunt function include computerized tomography (CT), plain films (X-Ray), magnetic resonance imaging (MRI), radionuclide shunt patency studies (RSPS, or 'shunt-o-gram'), shunt aspiration, and flow monitoring systems (ShuntCheck) [Boyle, Wallace, Madsen]. Each method, however, suffers from some combination of disadvantages, including excessive cost, poor reliability, low speeds, susceptibility to interference and patient discomfort, including potential for harm. CT scans and X-rays expose a vulnerable pediatric population to harmful radiation (1.57±0.6 mSv & 1.87±0.45 mSv, respectively). Shunted patients undergo an average of two CT scans annually that, over the course of the patient's lifetime, result in dangerous levels of radiation exposure that have been linked to the onset of neurological and hematological malignancies [Korai, Krishnamurthy]. The MRI approach costs $3000 per study, the measurement can interfere with magnetic shunt valves, the availability is limited, and the wait-times are typically long. Invasive testing, in form of RSPS or simple aspiration, is painful, time-consuming and often inaccurate [Brendel, Ouellette, Uliel, Vernet]. Recent diagnostic entrants attempt to address these drawbacks, but are limited by cumbersome, multi-step protocols, in some cases including ice mediated cooling, with equivocal or negative past clinical data [Madsen, Recinos, Boyle, Frim]. Observation alone can cost over $10,000 per admission, with prolonged hospital stays that compound the frustrations of patients, caregivers, and families alike [Boyle, Yue]. Ultimately, surgical intervention is required to assess and revise shunts in many patients. With risk of intraoperative complications, anesthetic exposure, gross procedural expenditures approach $67,000 per patient [Aqueduct neurosciences. Hydro association]. Because a significant proportion of such surgeries reveal shunt apparatuses with proper flow profiles, these unnecessary procedures represent a tremendous burden to the health care system.

This example presents a simple, non-invasive sensor platform that provides a low-cost, comfortable means for quantitatively assessing flow through cerebrospinal shunts. The platform exploits advances in materials, mechanics and fabrication schemes that serve as the foundations for a class of electronics that is ultrathin (<100 μm), soft (Young's modulus, E ~70 kPa), lightweight (area mass density, <10 mg/cm$^2$) and skin-like it is physical properties, with resulting flexural rigidities that are nine orders of magnitude lower than those of traditional, rigid sensors. Such 'epidermal' electronic systems support broad classes of measurement capabilities that offer clinical grade accuracy in capturing body kinematics[1] electrophysiological signals [2,3], soft tissue mechanical properties [4] chemical markers in sweat [5,6] and many others. Multimodal thermal characterization is also possible, owing to the exceptionally low thermal masses (<10 mJ cm$^{-2}$K$^{-1}$), fast response times (~10 ms), and exceptional precision in temperature measurements (~20 mK) of these platforms and to their ability for controlled delivery of thermal power to underlying tissue [7-11]. Specific embodiments allow for high resolution skin thermography and for precise measurements of the thermal conductivity and the thermal diffusivity of the skin. Recent work [12] also illustrates the possibility of quantifying macrovascular blood flow based on measurements of spatial anisotropies in thermal transport. Here, we extend these concepts to realize a soft, skin-interfaced sensor that can accurately measure flow through cerebrospinal shuts in real-time, in a noninvasive, quantitative and wireless manner. The results represent a breakthrough in hydrocephalus diagnostics, with ability to visualize flow in a simple, user-friendly mode, accessible to the physician and patient alike. Systematic benchtop evaluations, thermographic imaging and finite element analysis (FEA) of the physics of heat transport reveal the effects of skin thermal properties and thickness, as well as device and catheter geometries. The results establish considerations in design for a range of practical operating conditions. An integrated wireless system allows for recording and transmission of data to standard consumer devices such as smartphones and tablet computers. Trials on five adult shunt recipients with a diverse range of etiologies, and comparisons with CT, MRI and radionuclide tracing validate device function in-vivo, and advanced processing algorithms for quantitative determination of flow rates.

Figure 9:
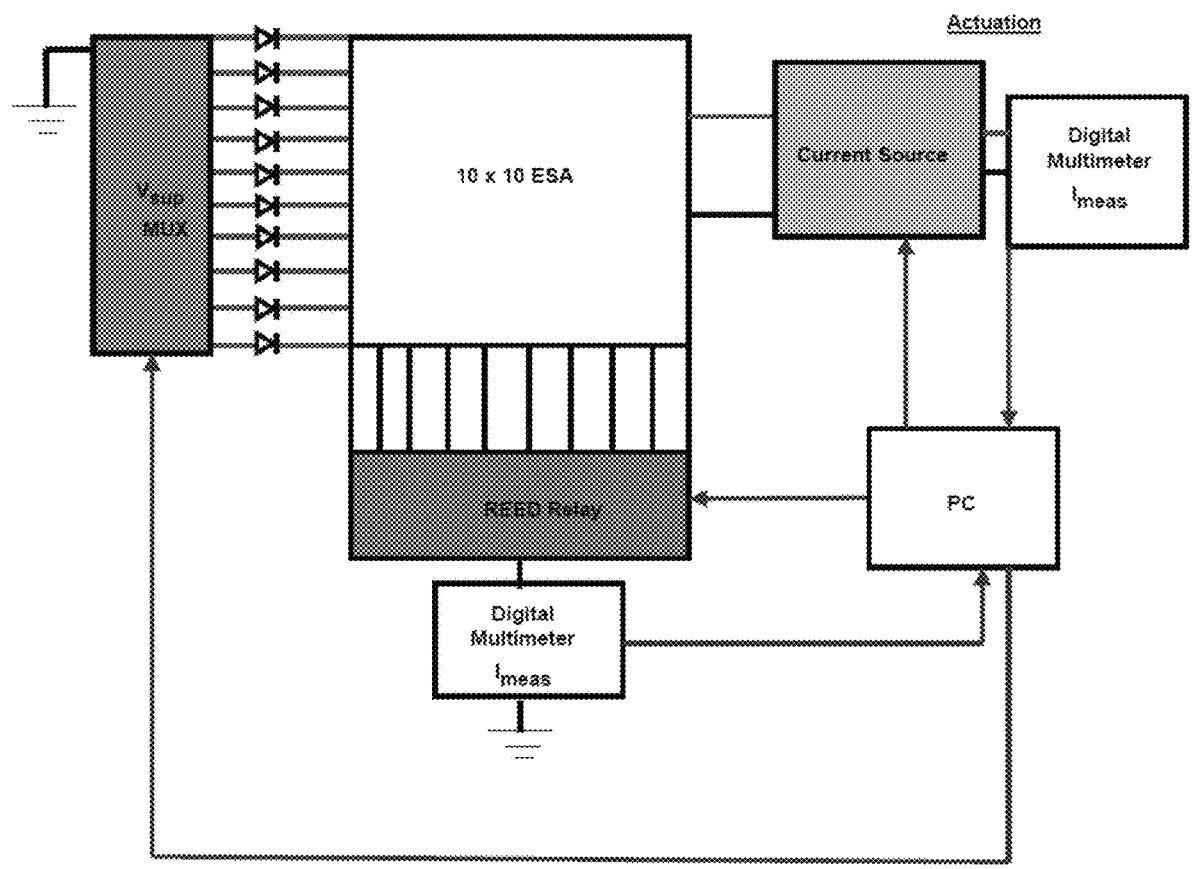
FIG. 9. Schematic illustration of data acquisition and control system for 100 sensor array.

Dense arrays for flow visualization: The feasibility of using arrays of epidermal temperature sensors and thermal actuators to quantify anisotropies in thermal transport through the skin induced by macrovascular blood flow has been demonstrated [10,12]. The device architectures and fabrication schemes shown here increase the number of sensors by nearly a factor of ten relative to this past work, and the density of these elements by a factor of four, using clusters distributed around a central thermal actuator, to provide levels of precision and spatial resolution necessary for characterizing flow through shunts. A schematic illustration of this platform (epidermal sensing array, ESA) appears in FIG. 1A. Optical micrographs of the key features are in FIG. 1B. The device illustrated here comprises a circular (R=2.5 mm) thin-film metallic (Cr/Au 10/50 nm) actuating element surrounded by 100 circular (R=0.25 mm) thin-film metallic (Cr/Au 10/50 nm) temperature sensors. Two layers of metallic traces (Ti/Cu/Ti/Au 20/600/20/25 nm) patterned in serpentine geometries define interconnects between the sensing and actuating elements, with polyimide (PI) as an interlayer dielectric. A film of PI (9 μm total thickness) patterned and aligned to the metal features serves as an encapsulation layer. A soft (70 kPa) substrate, such as an elastomeric substrate (Ecoflex, 100 μm) serves as a support. Connecting unique combinations of rows (to supply a sensing voltage, $V_{sup}$) and columns (to measure a resulting current, $I_{meas}$) enables individual addressing of each element in the array, as in FIG. 2C. Operation of the thermal actuator, as seen in the IR thermograph in FIG. 2C, results in a spatio-temporal pattern of temperatures that can be captured by high-speed, automated interrogation of the sensors in the array. An illustration of the data acquisition system appears in FIG. 9. Arrays in square geometries, with an equal number of input and output lines (10×10 for the case illustrated here) mitigate effects of parasitic current pathways. (Theoretical and experimental comparisons of current distributions in square and non-square arrays appear in FIGS. 8A-8B.) The ease of fabrication and robustness of operation of metallic resistive sensor elements make them attractive options compared to semiconductor devices, composite organic thermistors and others. The series of images in FIG. 2E illustrates the mechanical compliance and physical robustness of these systems.

Figure 10:
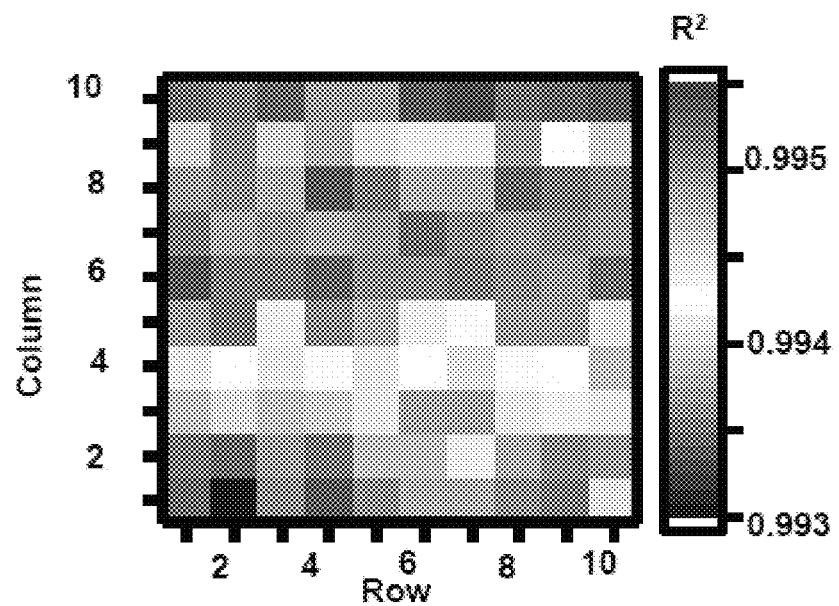
FIG. 10. Heat map with each pixel corresponding to a residual (R$^2$) value computed for each element in 10×10 array from linearly fitting $I_{meas}$ to temperature for calibration.
Figure 11:
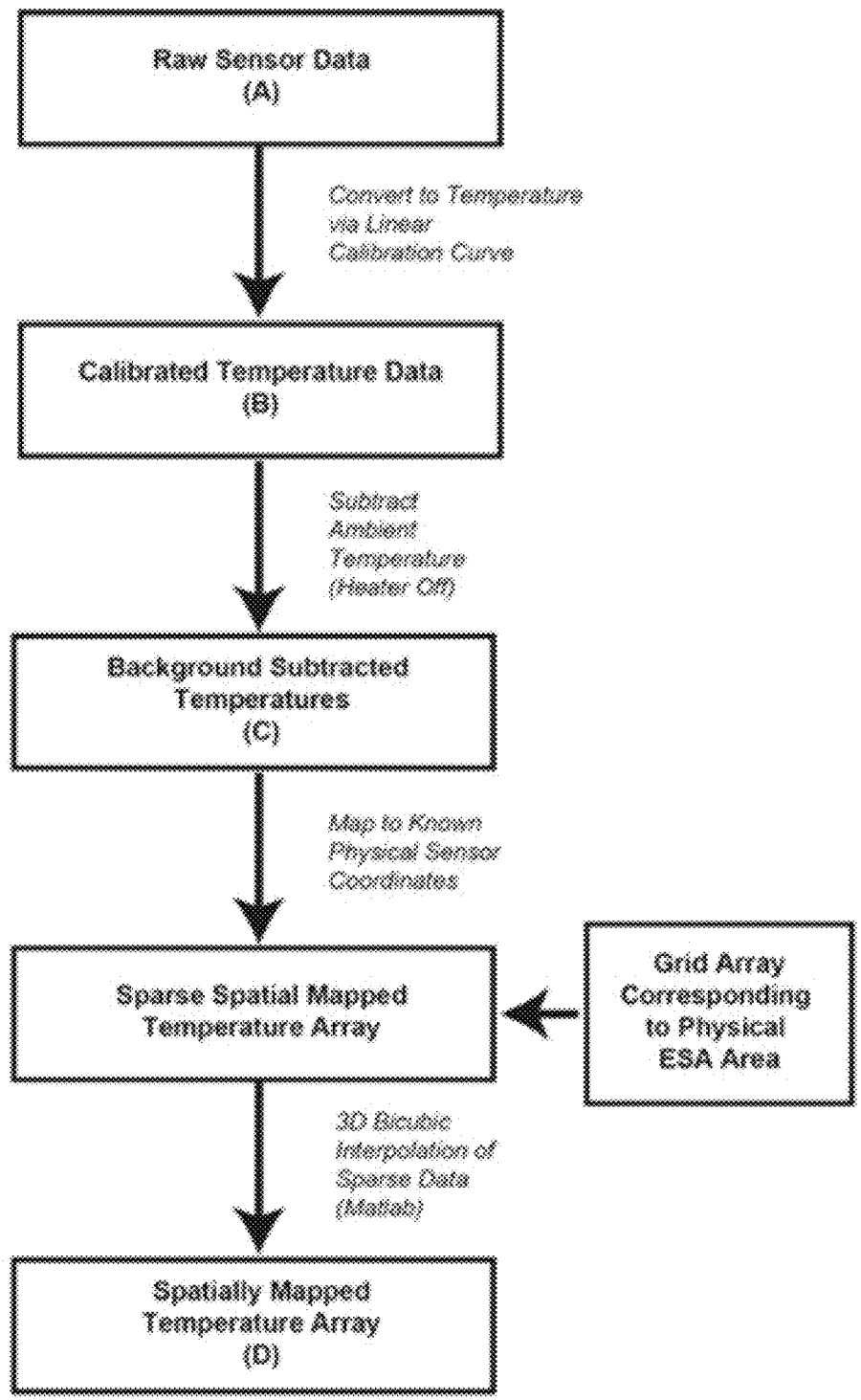
FIG. 11. Illustration of steps to convert measured current values to heat map, with steps corresponding to the images of FIG. 2D. Flow visualization and measurement from ESA. Top panel: Example of raw (resistance) ESA data. Second panel: Transformation of raw ESA data to calibrated temperatures via a calibration matrix specific to each ESA. Third panel: temperature differentials resulting from the removal of isotropic heat transfer effects from the thermal actuator via baseline subtraction. Bottom panel: ESA temperature map obtained from temperature differential map of preceding panel by meshed bicubic interpolation.

During operation, the current $I_{meas}$ that passes through a sensor fora given applied potential defines a resistance that can be converted to temperature via a linear calibration factor, whose goodness of fit is illustrated in FIG. 10. The effects of directional flow through a small diameter tube underlying the device can be seen in the IR thermographs of FIG. 2F. Here, thermal transport occurs most effectively along the direction of flow, thereby creating a pronounced anisotropy in the temperature distribution, with a magnitude that can be quantitatively related to the volumetric flow rate, as discussed subsequently. The layout of the sensing elements allows accurate measurements of this anisotropy for cases relevant to flow through subcutaneous shunts with typical dimensions. By comparison to previously reported platforms for sensing of blood flow, the high-density platforms introduced here (1) obviate the need for perfect alignment with the underlying ventricular shunt, (2) facilitate the use of image processing techniques to visualize flow fields, and (3) allow for statistical approaches to interpreting flow due to the density of information.

The schematic illustration in FIG. 2A identifies a set of 50 sensors upstream ($T_{upstream}$) and downstream ($T_{downstream}$) of the thermal actuator. Subtracting $T_{upstream}$ from $T_{downstream}$ for each physically-matched piecewise sensor pair (indicated by the paired colors in FIG. 2A) yields temperature differentials ($\Delta T_{sensor}$) that measure the degree of thermal anisotropy that results from fluid flow. As shown in FIG. 2B, $\Delta T_{sensors}$ for sensor pairs A and B that directly overlay a catheter exhibit strong thermal anisotropy under two different flow conditions (0.02 mL min$^{-1}$, 0.2 mL min$^{-1}$) within an established range for CSF flow[13]. Sensor location B displays a higher sensitivity to flow than location A due to the reduced effect of direct thermal conduction from the actuator, relative to anisotropic thermal transport due to fluid flow. Measurements of ΔT for distal sensor pairs orthogonal to the flow direction show weak anisotropy (C) while distal pairs parallel to flow direction (D) show an absence of flow-induced thermal anisotropy. This orientation dependence obviates the requirement for precise sensor alignment to tube direction due to the ESA sensor density and cardinal symmetry.

Figure 2C:
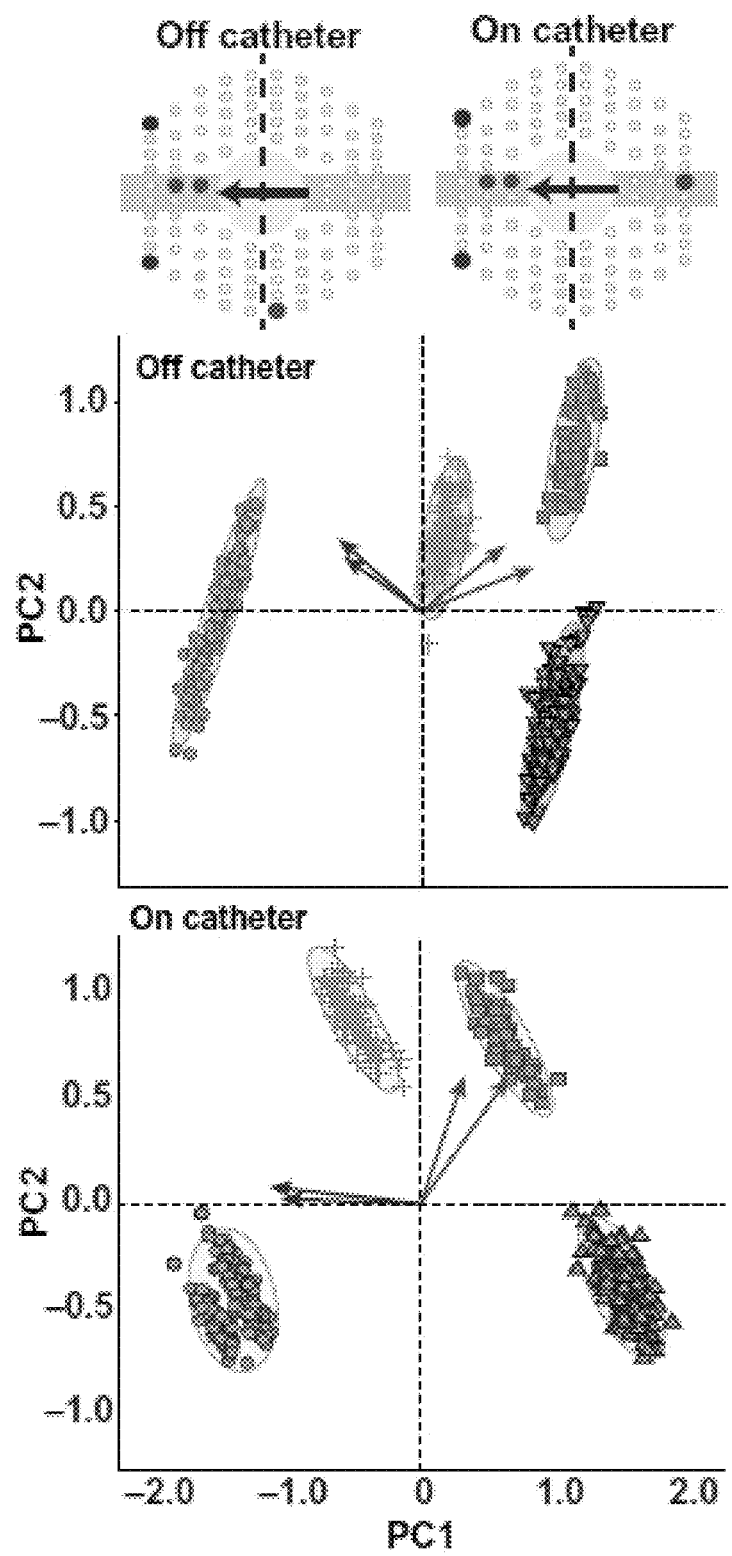
Figure 12A:
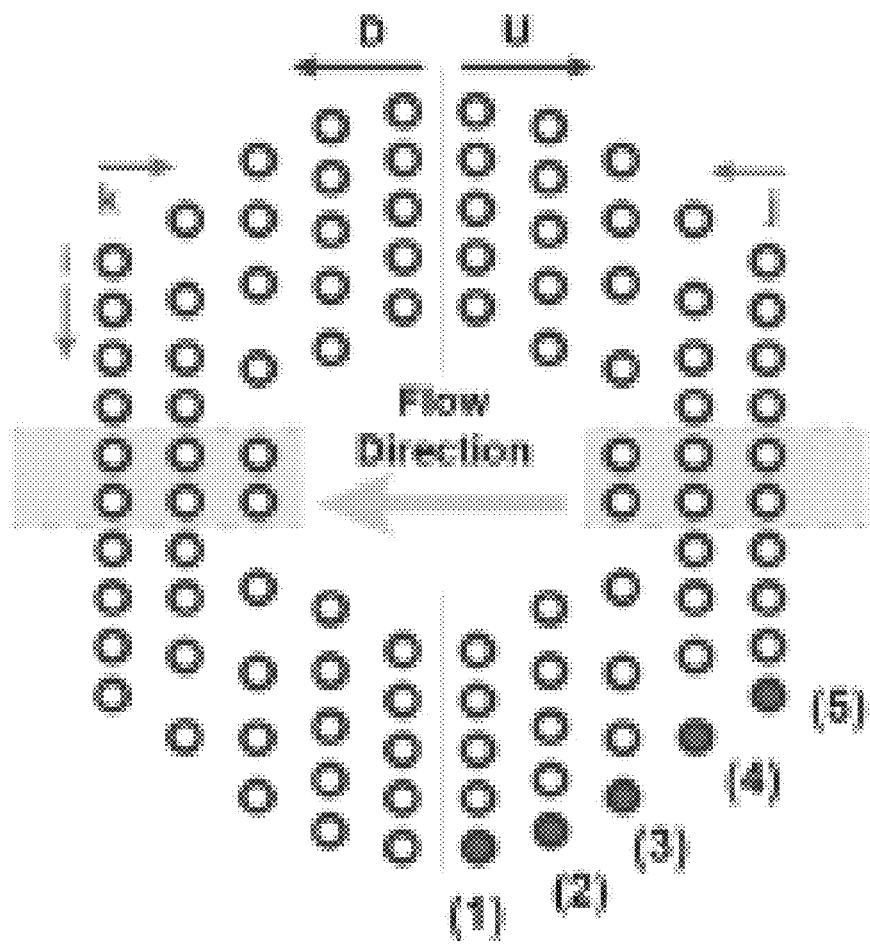
FIGS. 12A-12C. Flow visualization and measurement from ESA.
Figure 12B:
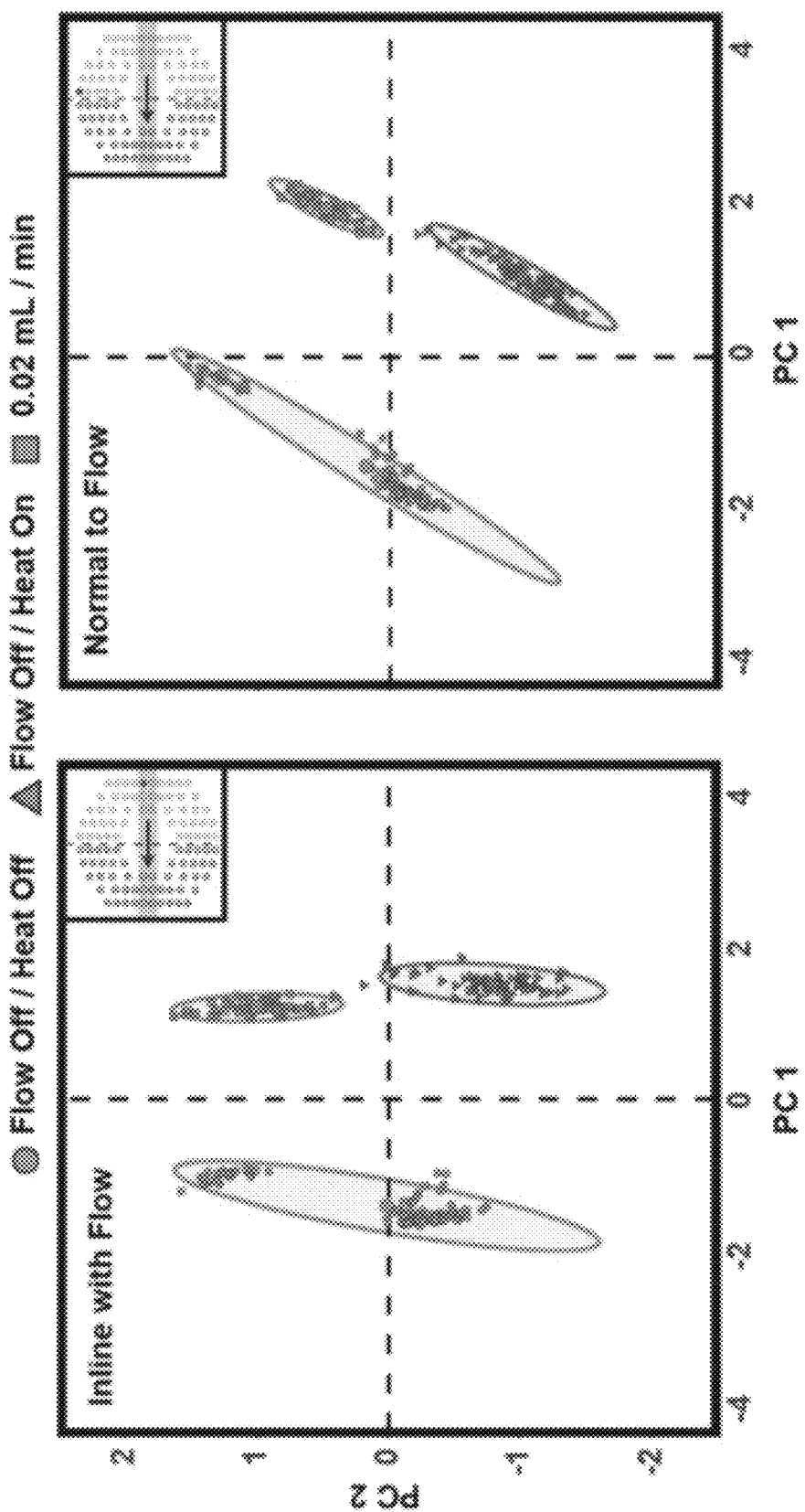
Figure 12C:
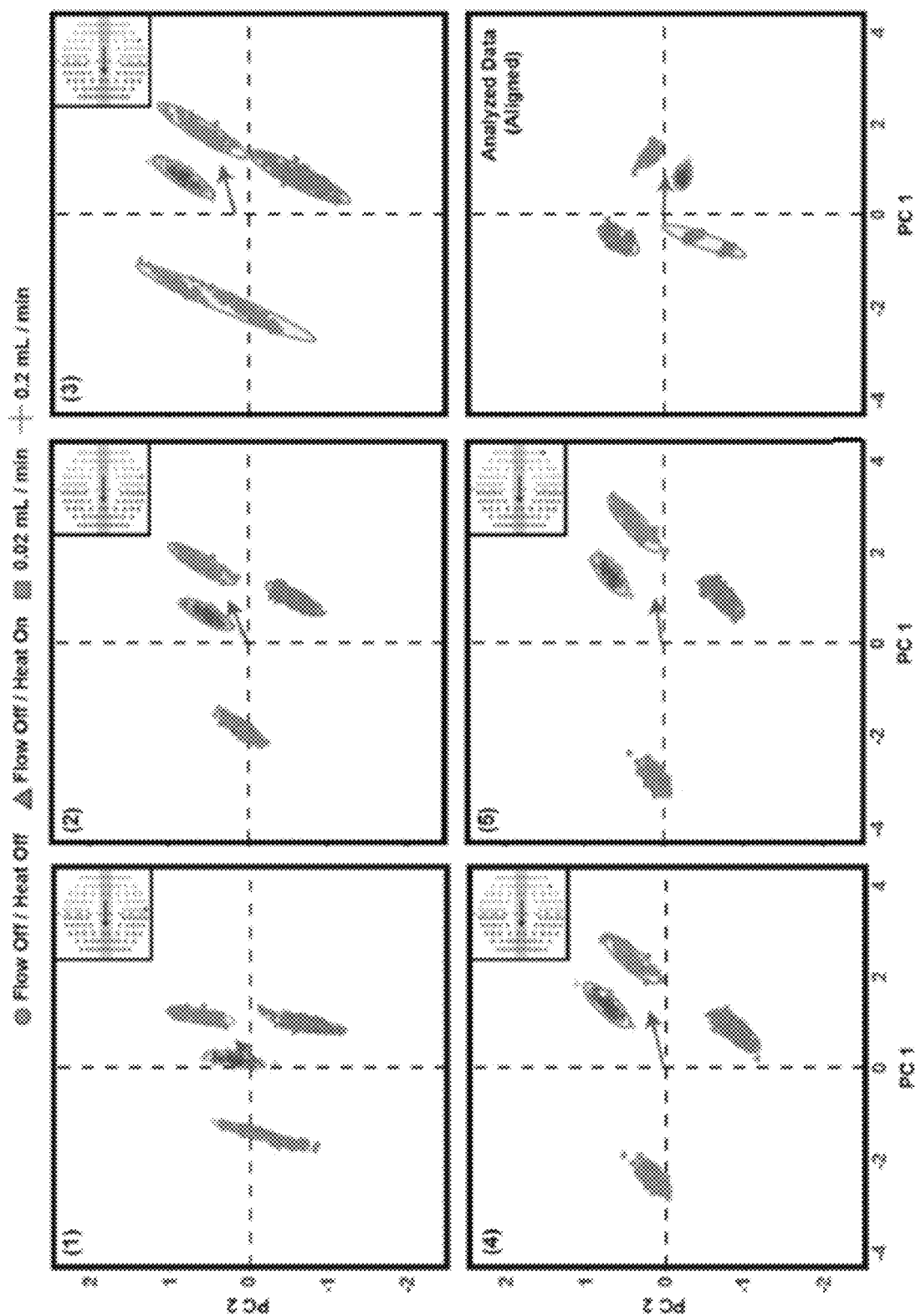

A Principle Component Analysis (PCA) model (generated via R) provides a facile method for assessing both catheter position with respect to the ESA ordinate system and for confirming the presence or absence of flow (shown in FIG. 2C). The PCA model, constructed from a time-series ESA measurement, uses $\Delta T_{PCA}$ values to calculate the principle components (PC). $\Delta T_{PCA}=T_{downstream}-T_{upstream,i}$, where $T_{downstream}$ is the temperature matrix of all downstream sensors (1-50) and $T_{upstream,i}$ is the temperature for a single (i) upstream sensor. The first two components (PC1, PC2) describe approximately 92% of the overall variability of the data (70.5% PC1, 22.1% PC2) with the remainder (8% across PC3:PC50) associated with noise. PCA biplots (FIG. 2C) show projections of each $\Delta T_{PCA}$ for two selected $T_{upstream,i}$ sensors (Top—orthogonal, distal sensor in red; Bottom—inline, distal sensor in red) at each measurement in an ESA time-series (same as FIG. 2B) in two dimensions using the first two principle components. FIG. 2C reveals data clustering (95% confidence ellipses) corresponding to three experimental conditions: absence of fluid flow without thermal actuation (flow off/heat off), absence of flow with thermal actuation (flow off/heat on), and fluid flow with thermal actuation with separate clusters for different flow regimes (0.02 mL min$^{-1}$, 0.2 mL min$^{-1}$). As shown, these clusters are independent of the selected $T_{U,i}$ sensor (additional biplots shown in FIGS. 12A-12B). A comparison of the data clusters and principal components shows that PC1 primarily relates to the degree of thermal actuation while PC2 relates to the presence or absence of flow. Mapping the variables to the PCA biplot indicates sensor correlation to fluid flow. In FIG. 2C, an overlay of four variable factors corresponding to $T_D$ sensors known to be proximal (red) and distal (blue) to fluid flow shows the positive correlation for the proximal sensors and negative correlation for the distal sensors to fluid flow for both orthogonal and inline $T_{upstream,i}$ sensors. PCA offers a strategy to mitigate effects of ESA misalignment by determining the $T_{upstream,i}$ sensor that yields the maximal separation between no flow/flow data clusters (along the PC2 axis). As observed in FIG. 2C, the inline $T_{upstream,i}$ sensor strongly separates these cluster groups as compared to the orthogonal $T_{upstream,i}$ sensor. In this manner, for scenarios without a priori orientation, PCA offers a straightforward means for evaluating correlations between $T_{upstream,i}$ and flow state and, therefore, orientation of the catheter relative to the ESA.

Figure 2D:
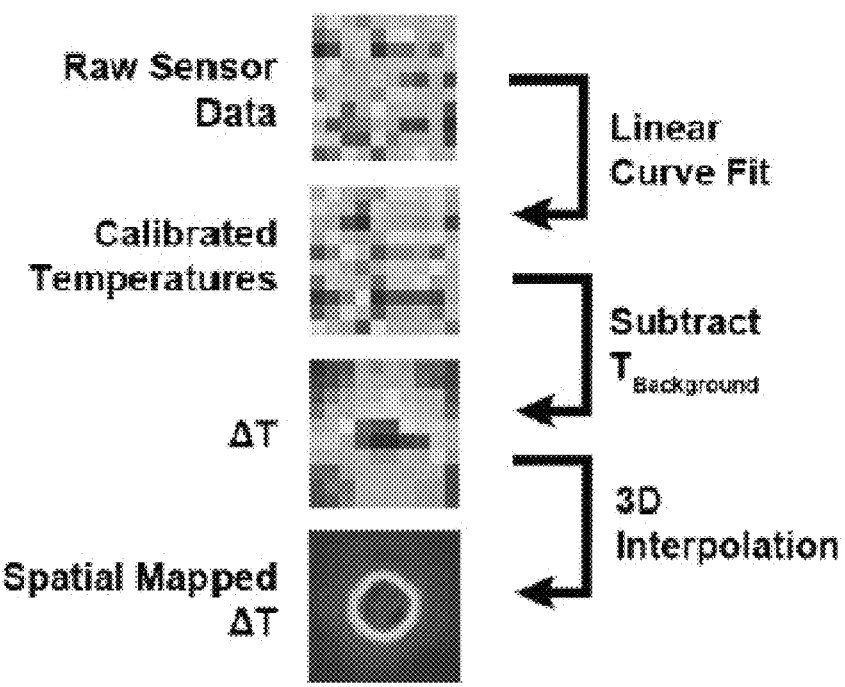
Figure 2E:
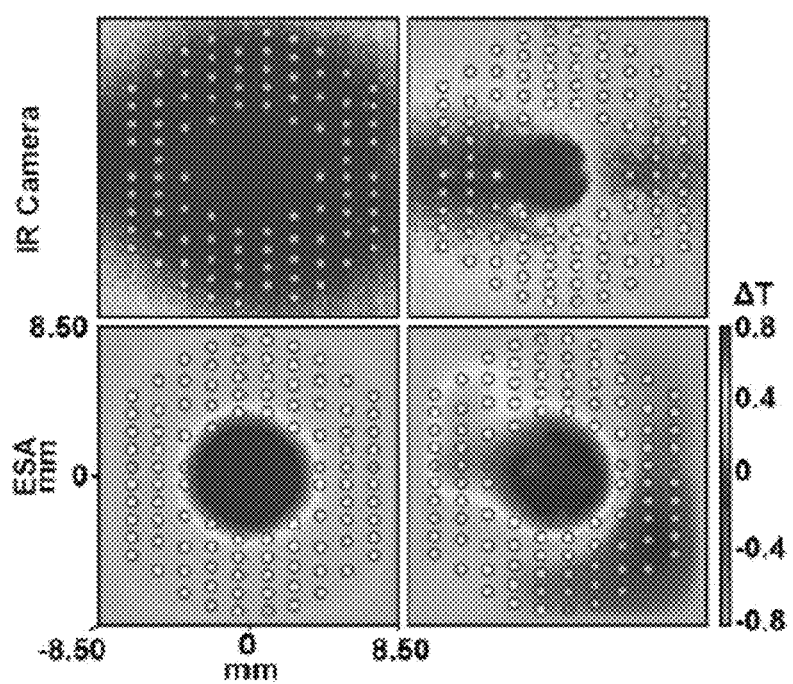

The density of the ESA enables spatial mapping of the temperature anisotropy that results from fluid flow. These maps result from the processing of raw measurements from the ESA as outlined in FIG. 2D. First, by converting the raw ESA measurements ($I_{meas}$)resistance and then temperatures by linear calibration (curve a priori established for each sensor of the ESA, process described in detail in FIG. 9), the temperature values can be mapped to the physical spatial coordinates of each sensor on a simulated square "pixel" array larger than the ESA (grid:17 mm×17 mm, 10 p×mm$^{-1}$) resulting in a 170×170×N matrix for a time-series measurement of N frames. Conversion to $T_{normalized}$ results from the subtraction of the background temperature $T_{background}$ from each frame. The temperature map results from fitting a surface to the measured $T_{normalized}$ values for each frame via meshed bicubic interpolation (boundary conditions $T_{normalized}=0$ from IR thermograph). Subtracting the actuator temperature and resulting isotropic heat transfer temperatures ($T_{actuator}$) from $T_{normalized}$ for every frame enhances visualization of flow-induced anisotropic thermal transport. FIG. 2D compares the ESA temperature maps with IR thermographs (same scale) in the absence (left) and presence (right) of flow (0.02 mL min$^{-1}$). As seen via the sensor overlay in each image, the high density of the ESA enables good fidelity in visualizing the thermal anisotropy over the embedded catheter. Although experiments with patients do not typically allow for direct measurements of the flow and no-flow cases, theoretically derived or a priori measured "calibration" $T_{actuator}$ facilitates the type of analysis described here.

Figure 3A:
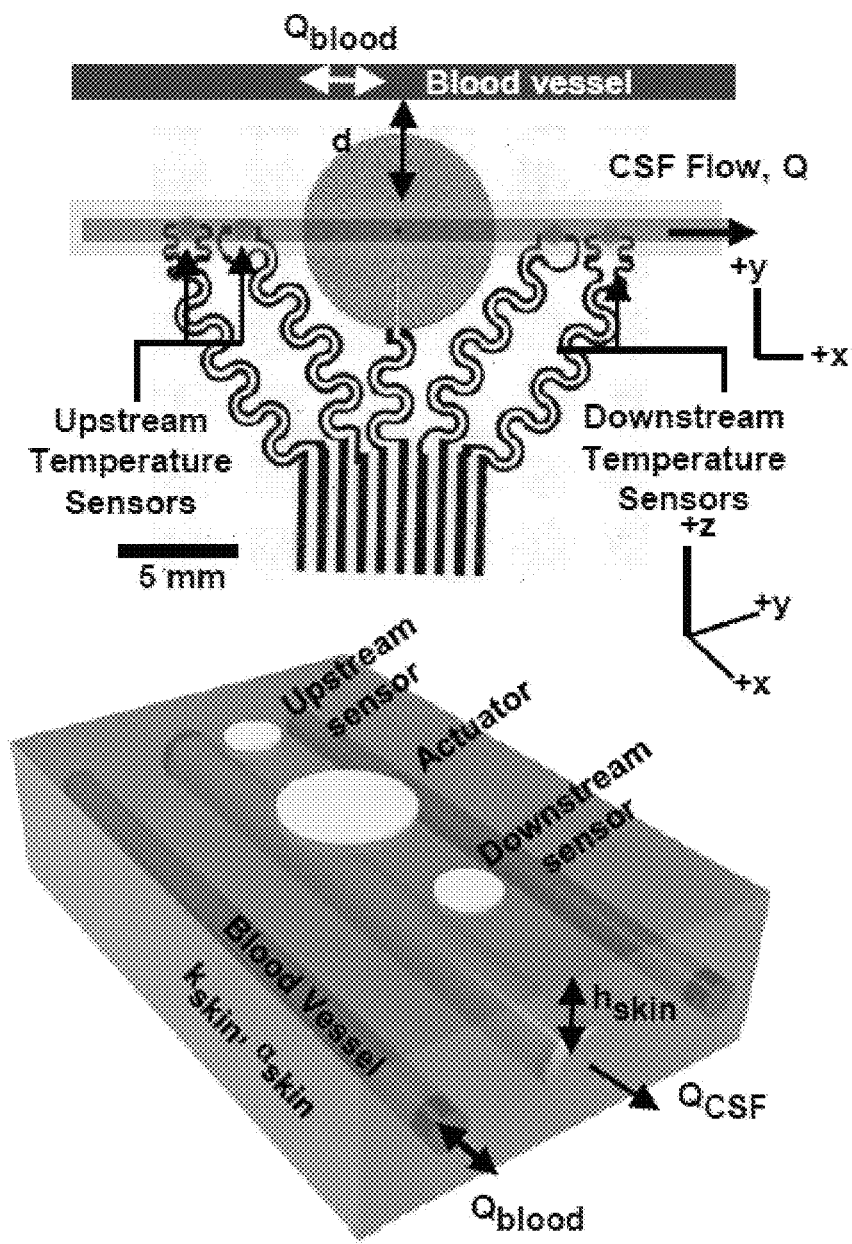
Figure 3B:
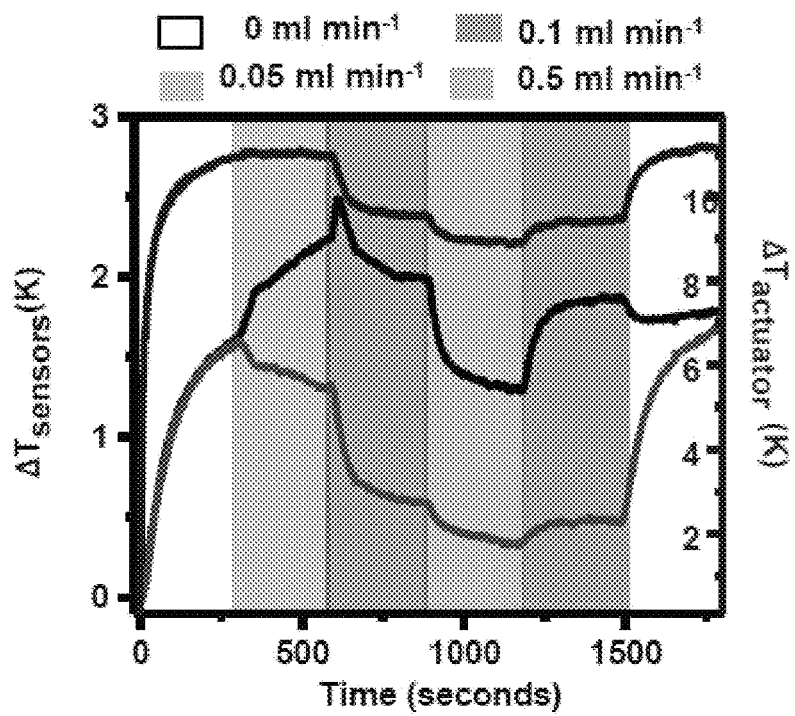
Figure 3C:
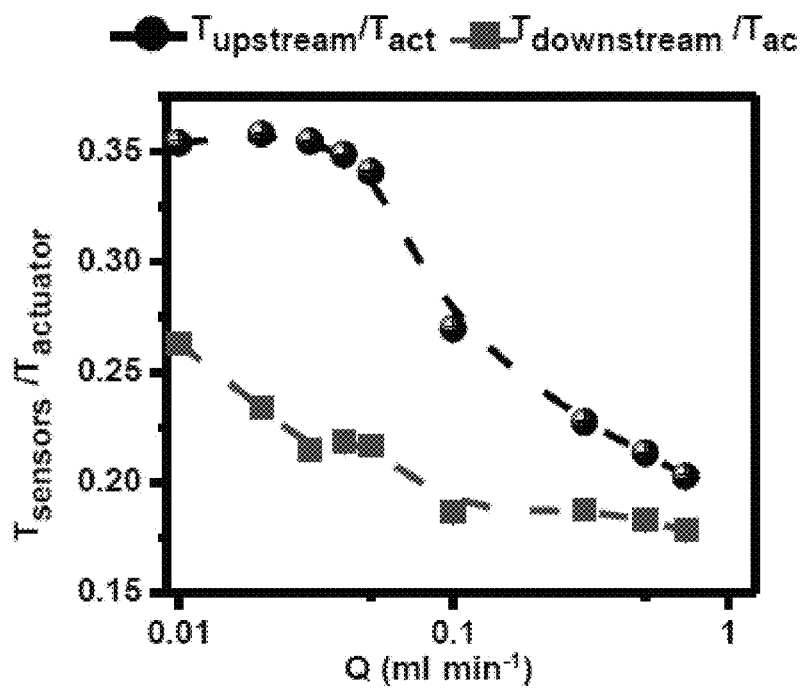
Figure 3D:
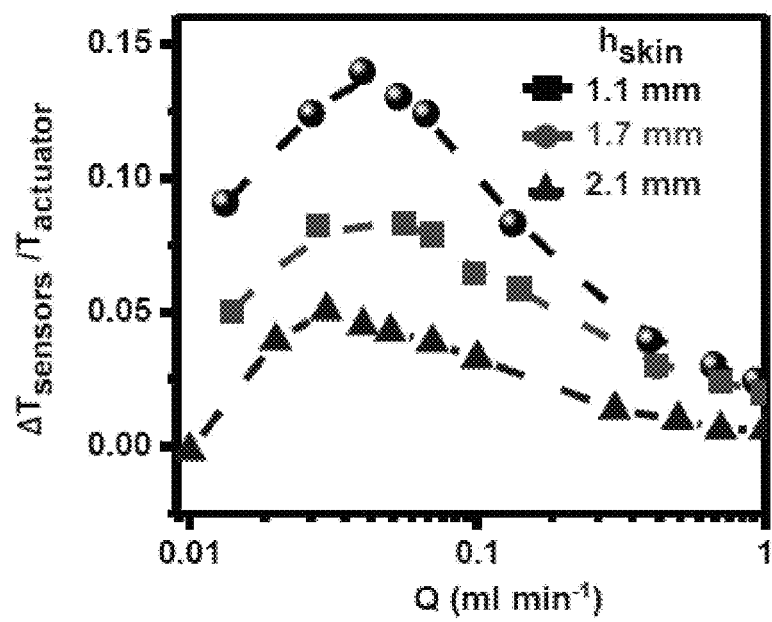
Figure 3E:
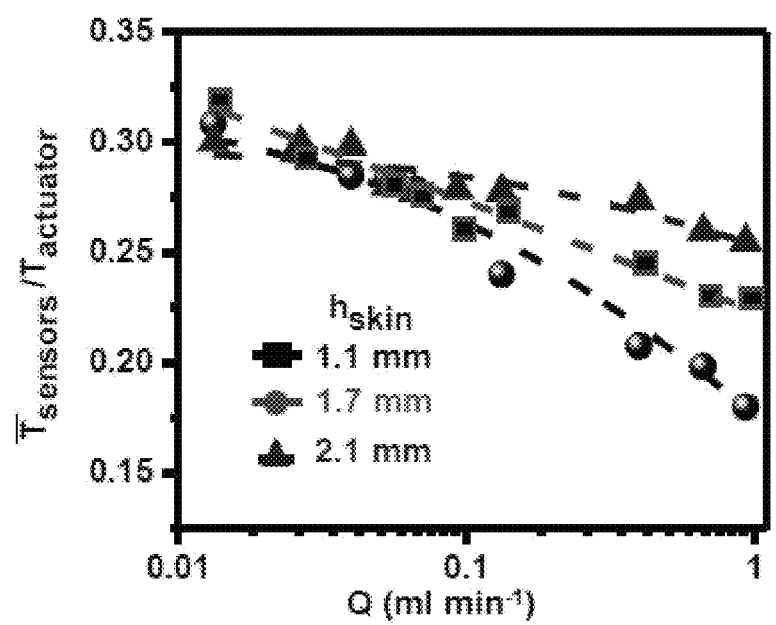
Figure 13A:
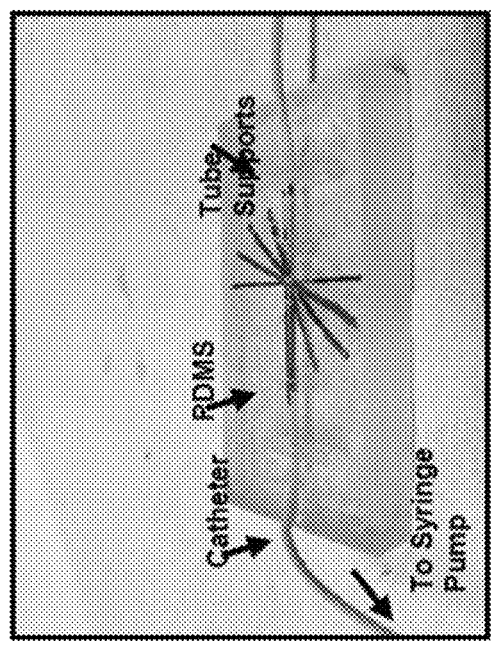
FIGS. 13A-13C. Benchtop flow system.

Quantitative analysis of flow and comparison to models: The full mapping results obtained with the high-density ESA suggest means for simplifying the sensor to allow rapid measurements in a low-cost platform that comprises at its core only of an actuator and a pair of sensors, located 1.5 mm upstream ($T_{upstream}$) and downstream ($T_{downstream}$) of the actuator respectively, which we refer to as an epidermal linear array (ELA). In this system, the actuator simultaneously serves as a temperature sensor, and the measured temperature of the actuator, $T_{actuator}$, yields a useful normalizing factor that facilitates data analysis independent of actuation power. Use of this system with a benchtop model allows for the controlled exploration of the effects of flow, thermal and geometric parameters. A schematic illustration of the device and evaluation set-up appear in FIG. 3A, with optical images of a representative system appearing in FIGS. 13A-13C. Operating the actuator at a controlled, low-power (1.35 mW/mm$^2$) level creates heat that diffuses through the silicone skin phantom (silicone) at a rate governed by the thermal diffusivity of this material, $\alpha_{skin}$. A scaling law that graphically illustrates the depth of penetration of this thermal field into the phantom appears in FIG. 14. Here, the phantom can be treated as a semi-infinite solid[14], which approaches a quasi-steady state equilibrium over relatively long (~400 s) times with a corresponding penetration depth of ~5 mm. Typical ventricular catheters are implanted subdermally, at depths of 1-2 mm [15], well within the range of detectability. The raw transient sensor and actuator responses after actuation ($\Delta T_{sensors}=T_{sensor}(t)-T_{sensor}(t_{actuation})$, $\Delta T_{actuator}=T_{actuator}(t)-T_{actuator}(t_{actuation})$), and during different flows ($Q_{CSF}$) in this system appear in FIG. 3B. In the absence of flow ($Q_{CSF}=0$) thermal transport from the actuator occurs equally in the $\mp x, \mp y$ and $-z$ directions, resulting in equal values for $\Delta T_{upstream}$, and $\Delta T_{downstream}$. This regime appears in the unshaded portion of FIG. 3B. The presence of flow leads to a non-monotonic effect on $\Delta T_{upstream}$, and $\Delta T_{downstream}$. At low flow rates (0 mL min$^{-1}<Q_{CSF}<0.05$ mL min$^{-1}$), the fluid serves to transport heat from the actuator preferentially to the downstream sensor, and away from the upstream sensor, resulting in a measured increase in $\Delta T_{downstream}$, and decrease in $\Delta T_{upstream}$, as seen in the blue shaded region in FIG. 3B. At higher flow rates (0.05 mL min$^{-1}<Q_{CSF}<1$ mL min$^{-1}$), the convective effects of the fluid dominate, leading to a net cooling effect on both sensors, but at different rates, with $\Delta T_{upstream}$ equilibrating at a lower value than $\Delta T_{downstream}$ as seen in the red and black shaded regions in FIG. 3B. The actuator is convectively cooled by the fluid at a rate governed by the magnitude of the flow, resulting in reductions of $\Delta T_{actuator}$, in the presence of flow as shown by the blue curve in FIG. 3B. These effects appear in the normalized quantities $T_{upstream}/T_{actuator}$ and $T_{upstream}/T_{actuator}$, shown for a complete range of physiologically relevant values of $Q_{CSF}$ in FIG. 3C. The non-monotonic effects of flow for different skin thicknesses ($h_{skin}$) increase and decrease when considering the difference between the sensors ($\Delta T_{sensors}/$ $T_{actuator}$) and their average ($T_{sensors}/T_{actuator}$), respectively, as shown in FIGS. 3D-3E. Here, $\Delta T_{sensors}/T_{actuator}$ and $T_{sensors}/T_{actuator}$ are measures of thermal anisotropy and flow magnitude, respectively. Taken together, these quantities allow for determination of flow rate, and can be used to distinguish degenerate points on either side of the peak values shown in FIG. 3D.

Figure 15:
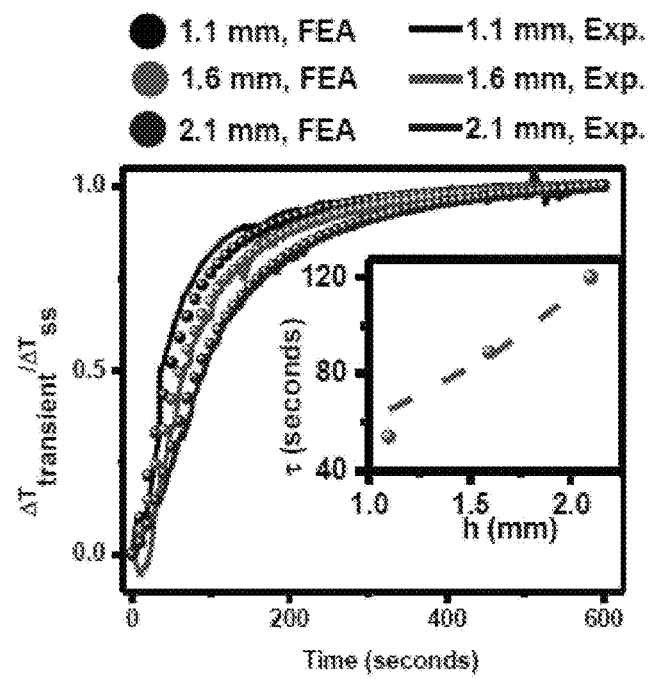
FIG. 15. Experimental and simulated transient responses of $\Delta T_{sensors}/T_{actuator}$ for three different values of $h_{skin}$ for $Q_{flow}=0.13$ mL min$^{-1}$ as a demonstration of an alternative method to quantify skin thickness, with data showing relationship between the time constant ($\tau$=time taken to reach 63.7% of steady-state value) and $h_{skin}$ (inset).

The thickness of the skin ($h_{skin}$) represents an important geometric parameter. As shown in FIGS. 3D-3E, increasing $h_{skin}$ decreases the effects of flow on the sensor responses, simply due to the finite depth of penetration of the thermal field. Although transient techniques can be used to determine $h_{skin}$ from thermal measurements, as shown in FIG. 15, in practice, $h_{skin}$ can be measured directly using CT and Doppler ultrasound, as discussed subsequently.

Figure 3F:
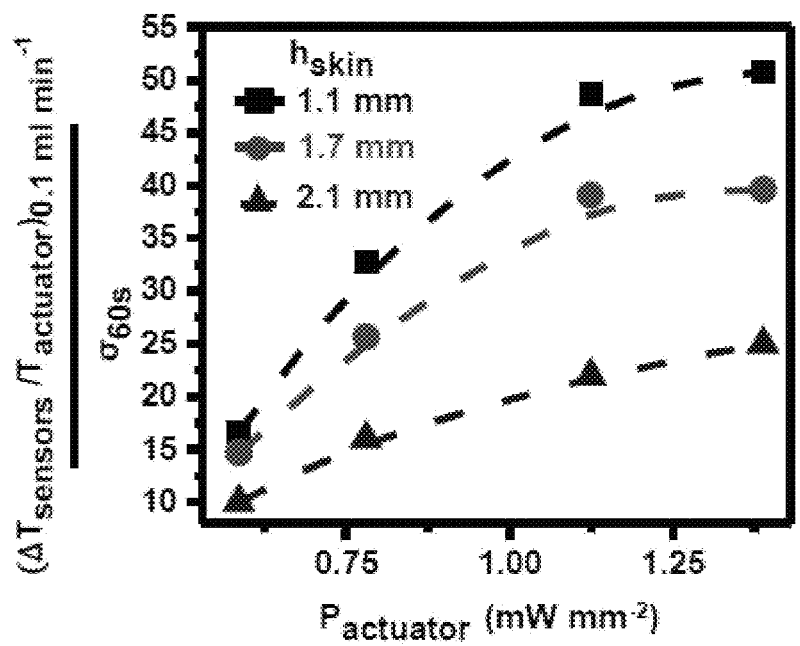
Figure 16:
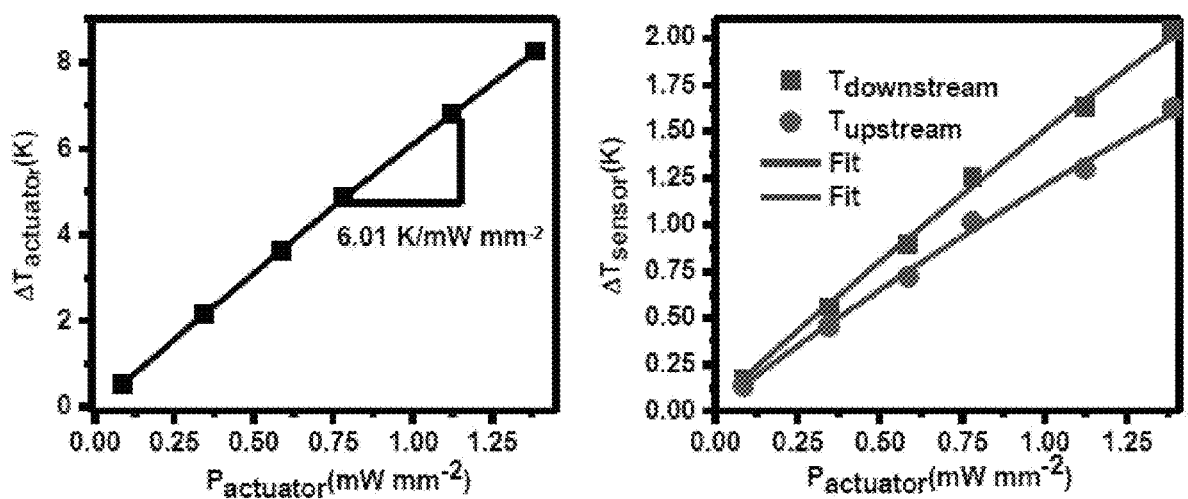
FIG. 16. $T_{actuator}$ and $T_{sensors}$ as a function of power level for $Q_{flow}=0.13$ mL min$^{-1}$ on Sylgard 184 skin phantom.

The power/area of the actuator ($P_{actuator}$) represents an important design consideration. Increasing $P_{actuator}$ improves the signal to noise ratio (S/N) of the measurements, but biological considerations set an upper limit for non-invasive use. The effects of $P_{actuator}$ on S/N appear in FIG. 3F, where the signal is an averaged measurement over 60 s (measured at 5 Hz) of $\Delta T_{sensors}/T_{actuator}$ for a flow rate of 0.13 mL min$^{-1}$. The noise is the standard deviation ($\sigma_{60s}$) computed to three significant digits. At sufficiently high values of $P_{actuator}$ ($P_{actuator}$>1 mW/mm$^2$) the advantages of increased actuation power diminish, and the noise stabilizes at 2% of the measured signal. The increase in local temperature varies linearly with $P_{actuator}$ at a rate of 6.01 K (mW mm$^{-2}$)$^{-1}$ on PDMS (Sylgard 184), as shown in FIG. 16.

Figure 3G:
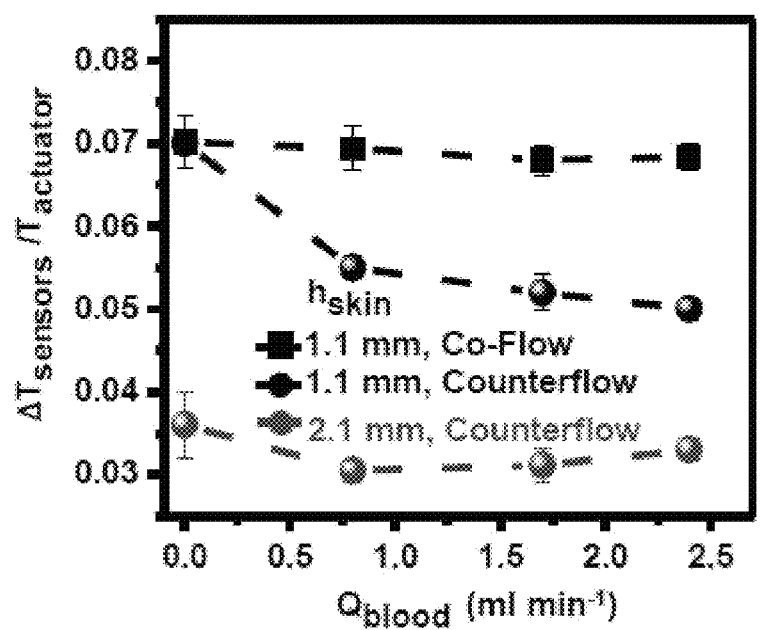
Figure 3H:
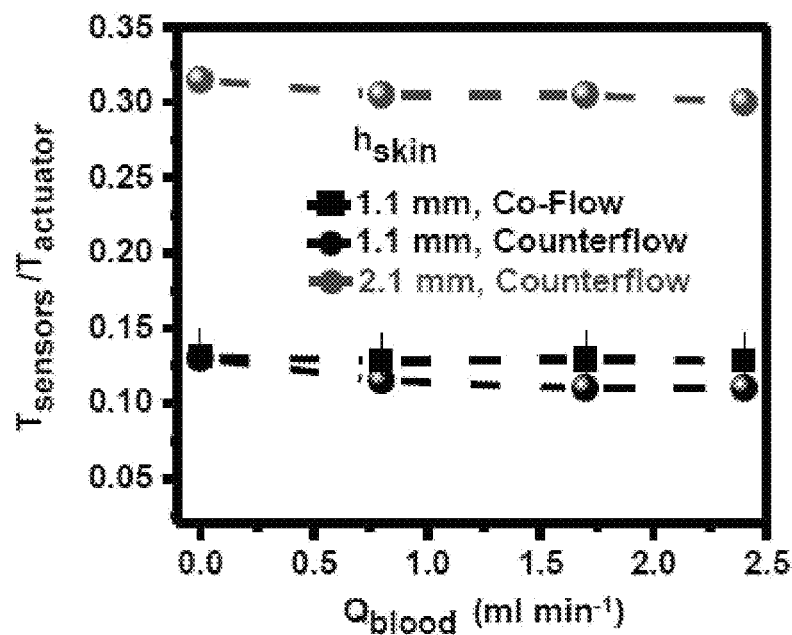

A possible confounding effect for the measurement follows from blood flow through superficial veins, as shown in a benchtop model in FIGS. 3G-3H, for two skin thicknesses and in two configurations: flow aligned with (+x, co-flow) and opposite to (−x, counter-flow) flow of CSF flow, for rates at the upper end of the range typically encountered in veins located near the surface of the skin of the neck. In practice, co-flow represents the most realistic case, as venous blood flow typically proceeds from the brain towards the heart. Arterial flow can be neglected since its depth (>1 cm) occurs below the limit of detectability for the sensors reported here. In experiments, flow through the catheter is 0.13 mL min$^{-1}$, and the phantom blood vessel ($R_{vessel}$=1 mm) resides ($d_{blood}$) 5 mm from the central axis of the sensor, and 2.5 mm from the edge of the actuator, as an extreme case. In this system, $h_{skin}$ is the same for both the catheter and the blood vessels. The counter-flow cases result in a 20% reduction in both $\Delta T_{sensors}/T_{actuator}$ and $T_{sensors}/T_{actuator}$, while the co-flow case results in a measured reduction of <5%.

Figure 3I:
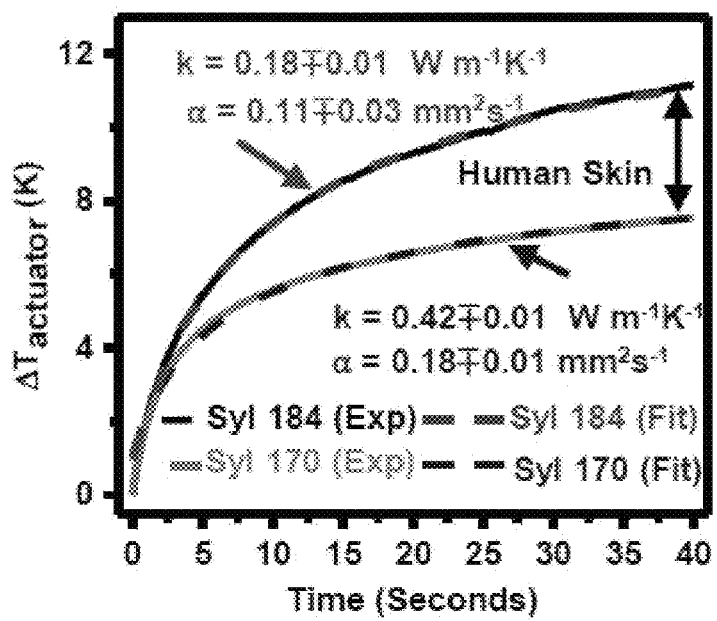
Figure 3J:
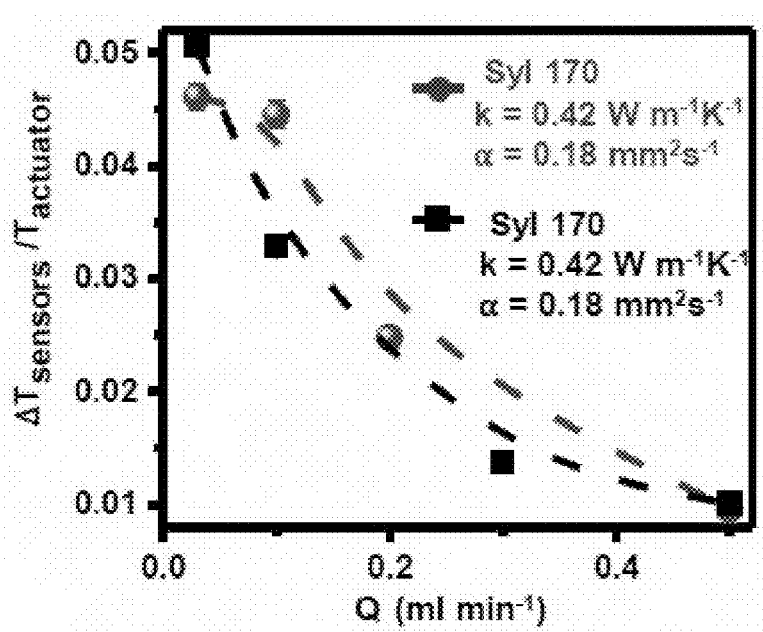
Figure 3K:
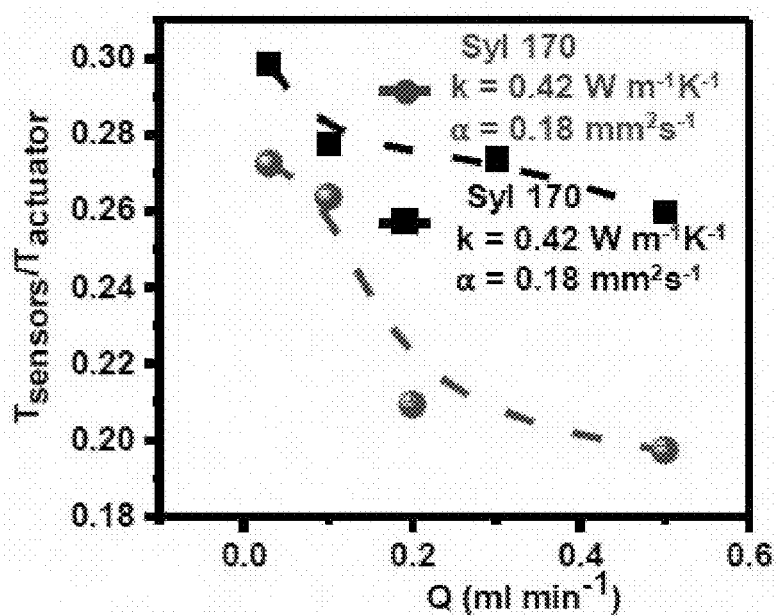

The thermal conductivity ($k_{skin}$) and diffusivity ($\alpha_{skin}$) of skin also represent unknowns, with human skin exhibiting a range of 0.2 W m$^{-1}$K$^{-1}$<$k_{skin}$<0.45 W m$^{-1}$K$^{-1}$ and 0.9 mm$^2$ s$^{-1}$<$\alpha_{skin}$<0.17 mm$^2$ s$^{-1}$ [11]. Phantom skins with properties that bound this range can be constructed from silicone materials with two different formulations (Sylgard 170 and Sylgard 184, Dow Corning, Inc.). Measurements of the thermal properties of these materials (FIG. 3I) match literature values: $k_{184}$=0.18∓0.01 W m$^{-1}$ K$^{-1}$, $\alpha_{184}$=0.11∓0.03 mm$^2$ s$^{-1}$ and: $k_{170}$=0.42∓0.01 W m$^{-1}$K$^{-1}$, $\alpha_{170}$=0.18∓0.01 mm$^2$ s$^{-1}$. The measured values of $\Delta T_{sensors}/T_{actuator}$ are nearly identical for these two cases, as shown in FIG. 3J. By contrast, the increased rates of thermal transport associated with Sylgard 170 increases the cooling effect of the fluid, thereby reducing the values of $T_{sensors}/T_{actuator}$ as shown in FIG. 3K. The result increases the sensitivity of the sensor.

Ventricular catheters are constructed from standard medical-grade silicones, and their thermal properties are assumed to be known a-priori ($k_{catheter}$=0.22 W m$^{-1}$ K$^{-1}$, $\alpha_{catheter}$=0.12 mm$^2$ s$^{-1}$) [16].

Figure 1C:
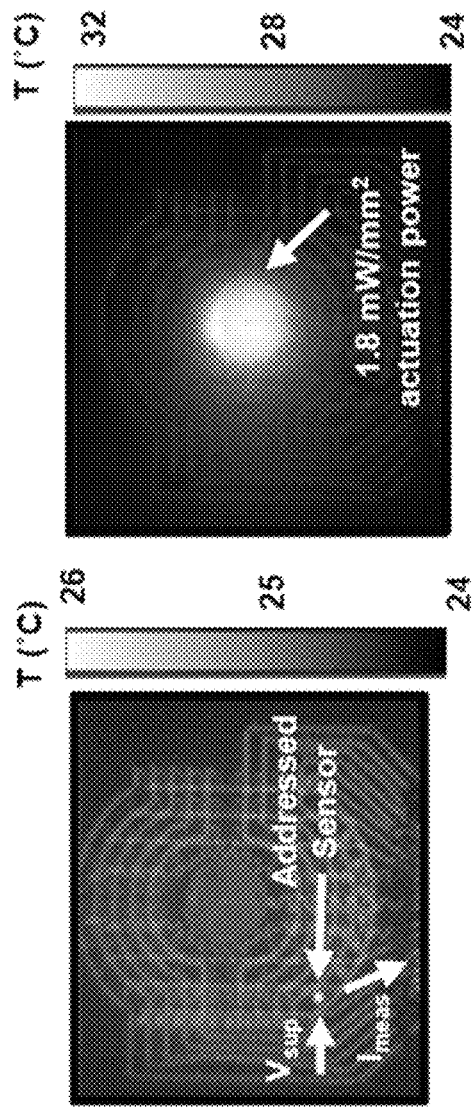
Figure 1D:
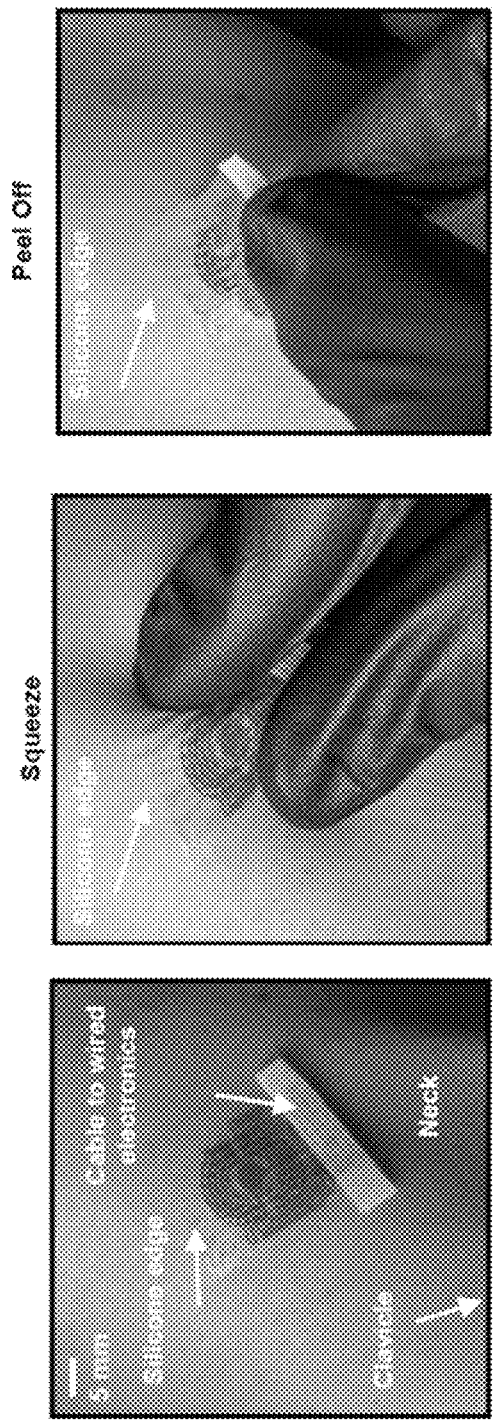

Additional experiments quantify the convective heat transfer coefficient ($H_{conv}$=20 W m$^{-2}$K$^{-1}$, FIG. 17), tolerance in positioning (30° rotational tolerance, FIG. 18B, ~1 mm translational tolerance, FIG. 18C) and noise introduced by the data acquisition system as a function of sampling window (FIGS. 19A-19D).

Systems provided herein are compatible with wireless data acquisition, including via Bluetooth. This represents an important patient care aspect, as the patient need not be hard-wired to any instruments. In this manner, continued monitoring is possible without confining patient location or motion.

Figure 5A:
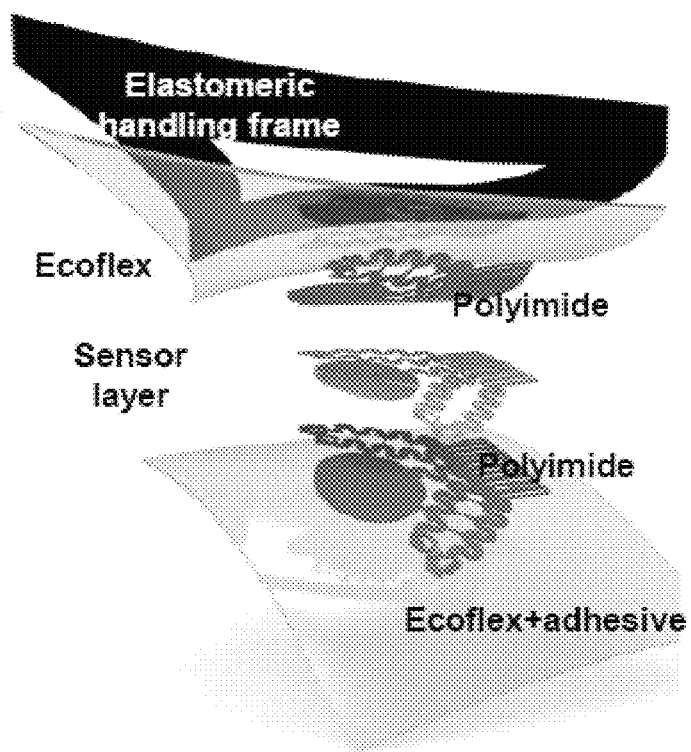
FIG. 5A-5J. Patient trials.
Figure 5B:
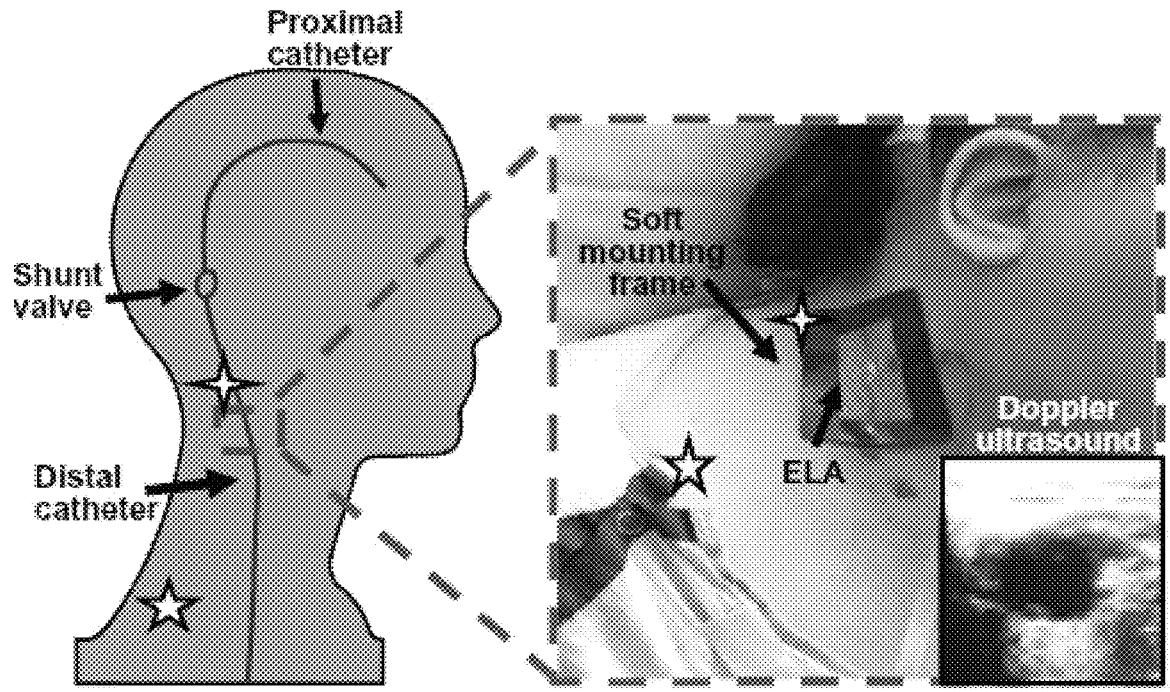
Figure 5C:
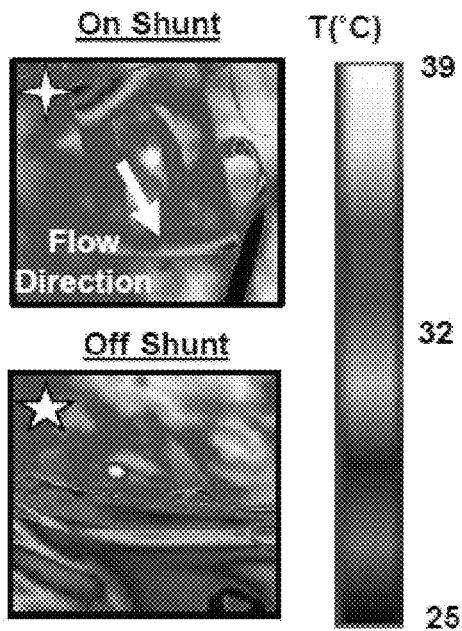

Human studies for the evaluation of ventricular shunt function: Experiments on five shunt recipients with varying pathologies demonstrate the utility of these measurement platforms. The device designs address three needs: (1) ease of handling for the surgeon to ensure facile placement and removal, (2) comfort for the patient during application, operation and removal, and (3) robust mechanical and thermal coupling to the skin. A schematic illustration of the resulting embodiment appears in FIG. 5A, showing the ELA and ultrathin elastomer substrate (100 μm, Ecoflex+MG7 1010 Adhesive) supported by an elastomeric frame (2 mm, Sylgard 170). These platforms adhere robustly and non-invasively to the skin via van der Waals interactions alone, without the need for separate adhesive layers, as illustrate in FIGS. 19A-19D, where a device maintains conformal contact with the skin even under extreme deformations. Successive measurements involve placement on the skin over the distal catheter ('on-shunt'), and at a location adjacent to the distal catheter ('off shunt'). The off-shunt measurement has two key uses: (1) it serves as a control for comparison to the on-shunt measurement and (2) it allows for the measurement of skin thermal properties without the influence of flow. FIG. 5B schematically illustrates the on-shunt and off-shunt location. Locating the catheter under the skin via touch was facile, and precise positioning was achieved with Doppler ultrasound (Sonosite Inc., Bellevue Wash.). A representative Doppler image of the catheter appears in FIG. 5B (inset). Linear markings on the device, visible in FIG. 5B, allow for easily alignment of the central axis of the actuator and sensors with the underlying shunt. Although the shunt is not visible under the skin, its ends can be easily aligned to the markings on the device via touch. Low-power actuation (1.3 mW/mm$^2$) ensures maximum temperature increases of <5° C., as confirmed by IR images in FIG. 5C. These values are well below the threshold for sensation, in accordance with IRB-approved protocols. Markers in FIG. 5B identify mounting locations in FIG. 5C. The results show a characteristic tear-drop distribution of temperature, consistent with flow.

Figure 5D:
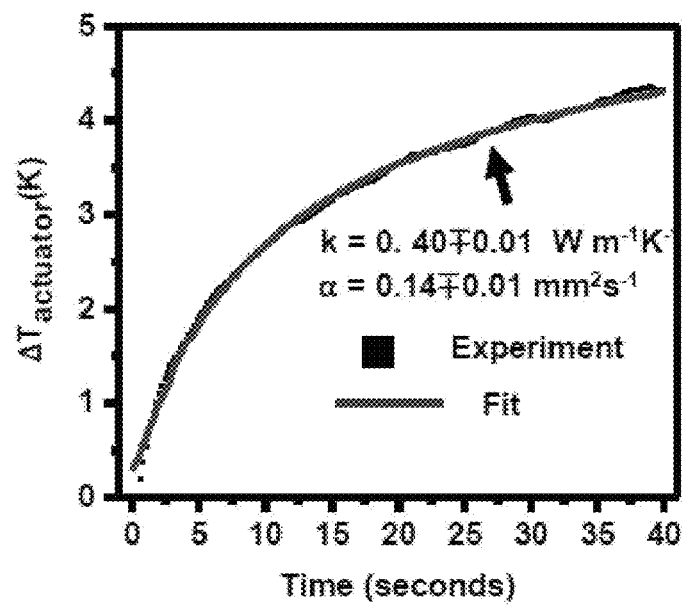
Figure 5E:
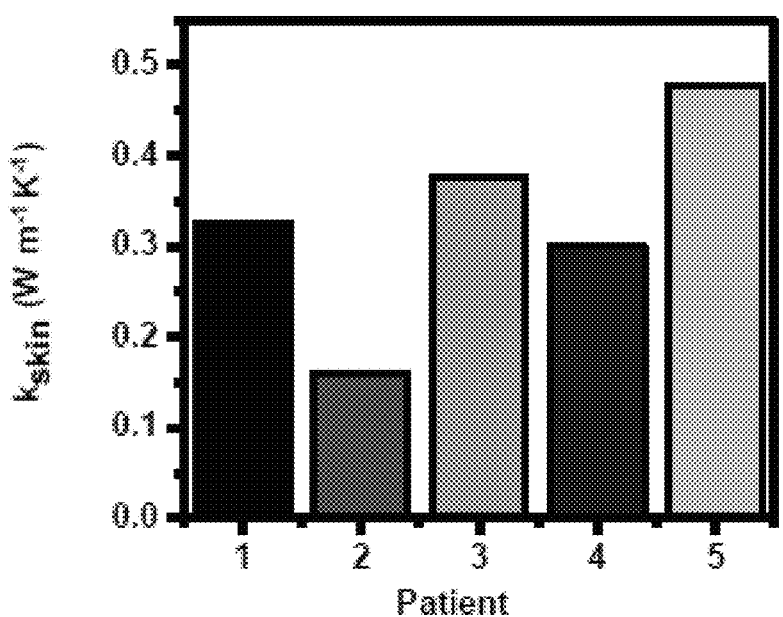
Figure 5F:
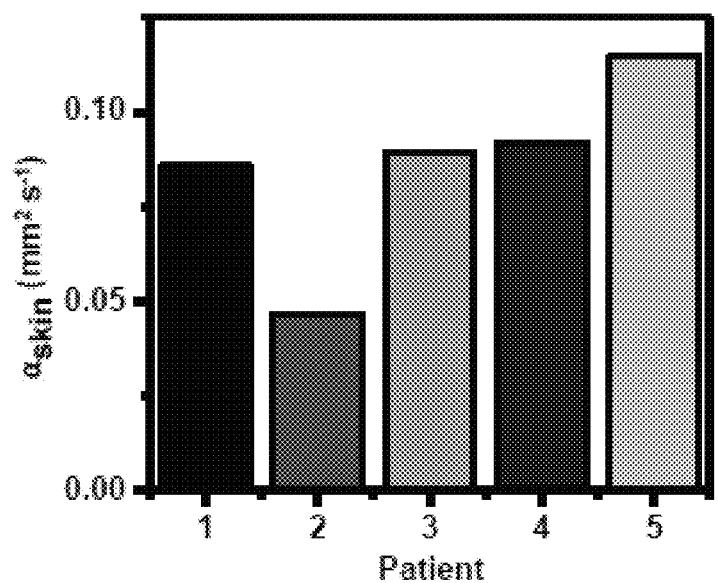
Figure 5G:
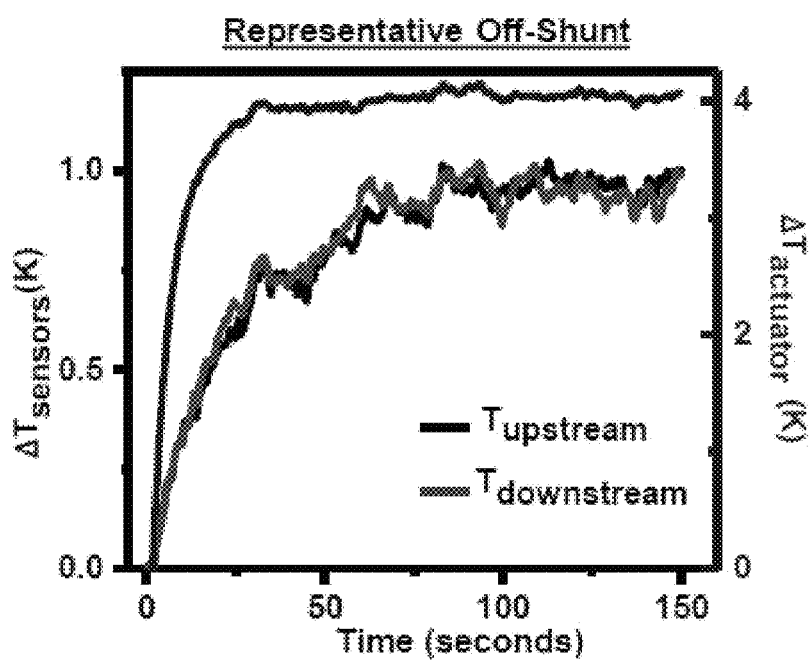
Figure 5H:
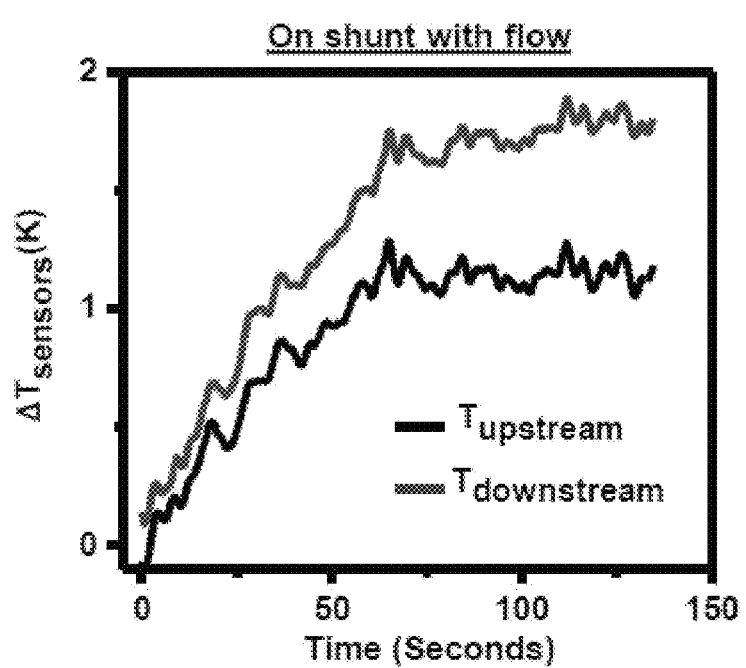
Figure 5I:
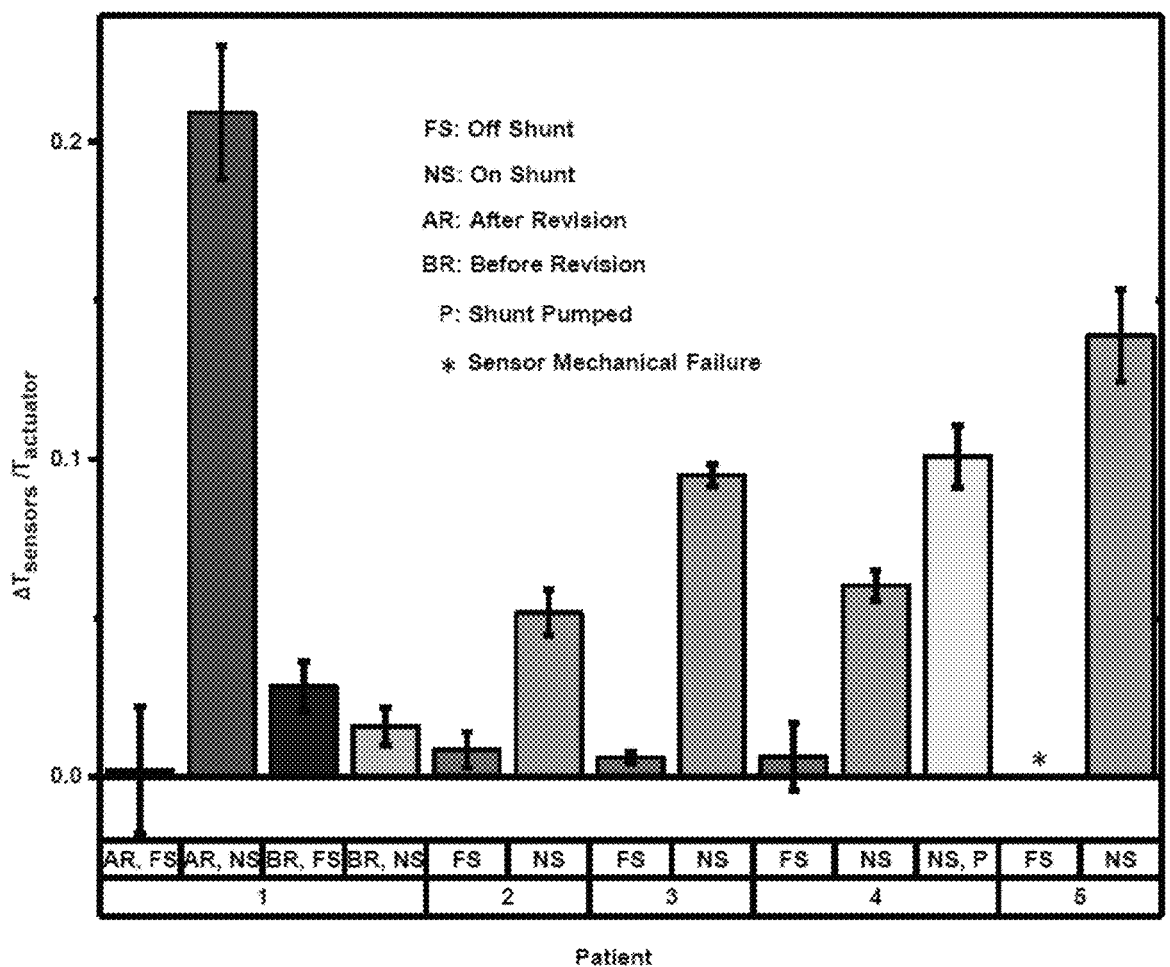
Figure 5J:
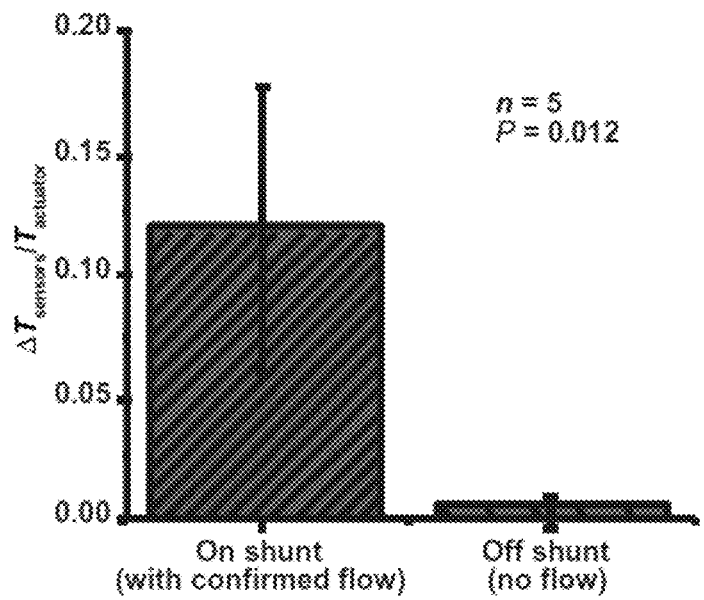

Transient, off-shunt measurements of $T_{actuator}$ define the thermal transport properties of the patient's skin. A representative response before, during and after actuation appear in FIG. 5D. Values of $k_{skin}$ and $\alpha_{skin}$ extracted from these data appear in FIGS. 5E-5F; the magnitudes are comparable to those expected for skin [11]. Data from the flow sensor are in FIGS. 5G-5H, where the red, black and blue curves represent the temperatures measured from the upstream sensor, the downstream sensor, and the actuator, respectively. Locations adjacent to the shunt that are free of near-surface blood vessels present no sources of thermal anisotropy and, therefore, can serve as control measurements. Results from a representative case are in FIG. 5G, where the upstream and downstream responses are nearly identical. Anisotropy that results from flow through a shunt appears in FIG. 5H. In a simple binary sense, the presence or absence of flow corresponding to shunt functioning or failure can be immediately determined simply by observing the presence or absence of thermal anisotropy. Measured values of $\Delta T_{sensors}/T_{actuator}$ appear in FIG. 5I for on-shunt and off-shunt locations for all 5 patients. Anisotropy appears clearly for all working shunts. Error bars correspond to standard deviations computed over 100 samples. Raw data from two additional cases appear in FIG. 20. Details of each patient's etiologies and results are in FIGS. 21A-21B.

Studies by X-Ray, MRI and CT imaging validate the measurements. FIG. 6A corresponds to a patient (F, 36) with a shunt malfunction suspected to be due to a kink in the distal catheter, and later confirmed by the X-Ray and Radionuclide Tracer (RT) images. Surgical intervention relieved the kink, causing a dramatic, visible increase in flow, as shown in the optical image in FIG. 6B. The continuous presence of flow was further confirmed via post-operative X-Ray and RT, revealing a straightened distal catheter and a clear trace beyond the valve, as shown in FIG. 6C. Placement of the ELA at on- and off-shunt locations respectively, revealed no flow before the revision, consistent with X-Ray and RT imaging. Post operatively, the off-shunt measurement showed no appreciable changes, while the on-shunt measurement showed the clear presence of flow, as shown in FIG. 6D.

Figure 7A:
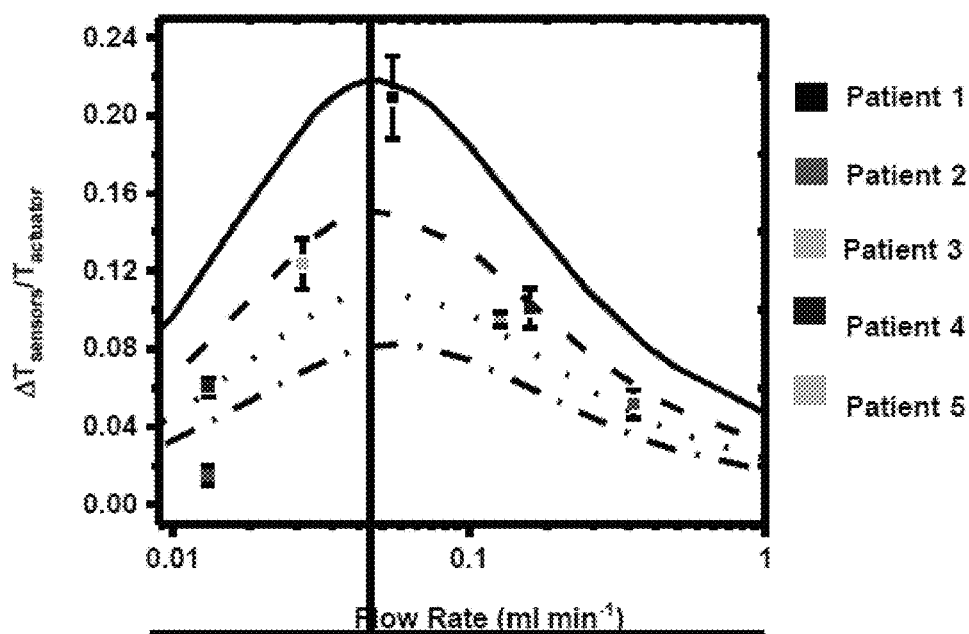
FIGS. 7A-7D. Computation of flow rates.
Figure 7B:
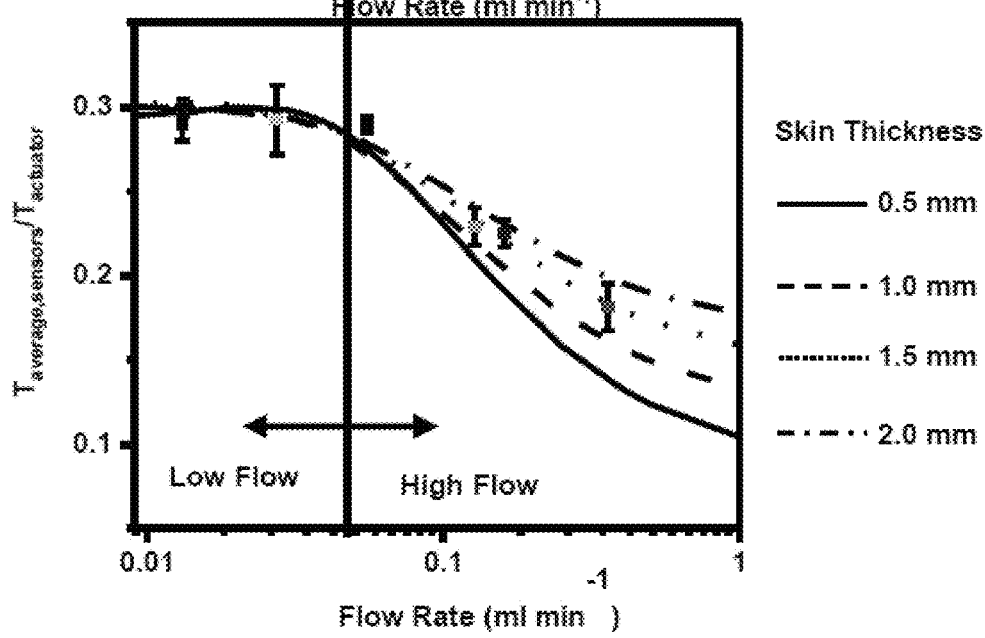
Figure 23:
FIG. 23. Representative CT image of skin thickness over superficial catheter location over clavicle.

The quantitative extraction of flow rates from such data can be accomplished via fitting to FEA models that use measurements of $k_{skin}$ and $\alpha_{skin}$, $\Delta T_{sensors}/T_{actuator}$ and $T_{sensors}/T_{actuator}$ and a priori knowledge of the inner and outer diameters of the catheter, and its thermal properties $k_{catheter}$ and $\alpha_{catheter}$. Placing the sensor at distal catheter locations that are determined, via touch, to be the most superficial maximizes the precision of the measurement. Analysis of CT and Doppler ultrasound images, such as the ones shown in FIG. 5B and FIG. 23 define $h_{skin}$ at these locations to be 1.5 mm∓0.1 mm. FEA yields computed curves for $T_{sensors}/T_{actuator}$ and $\Delta T_{sensors}/T_{actuator}$ for a 0.01 ml min$^{-1}$<$Q_{CSF}$<1 ml min$^{-1}$. In this way, measured values of $T_{sensors}/T_{actuator}$ define regimes of flow, i.e. high-flow (Q>0.05 mL min$^{-1}$) or low-flow (Q<0.05 mL min$^{-1}$). Specifically, values of $T_{sensors}/T_{actuator}$>0.29 represent low-flow, and $T_{sensors}/T_{actuator}$<0.29 represent high-flow for all skin thicknesses, as shown in FIG. 7B. Measured values of $T_{sensors}/T_{actuator}$ and $\Delta T_{sensors}/T_{actuator}$ are then iteratively fitted to yield a unique flow rate. Following this process for our measured data yields quantitative flow values.

Figure 7C:
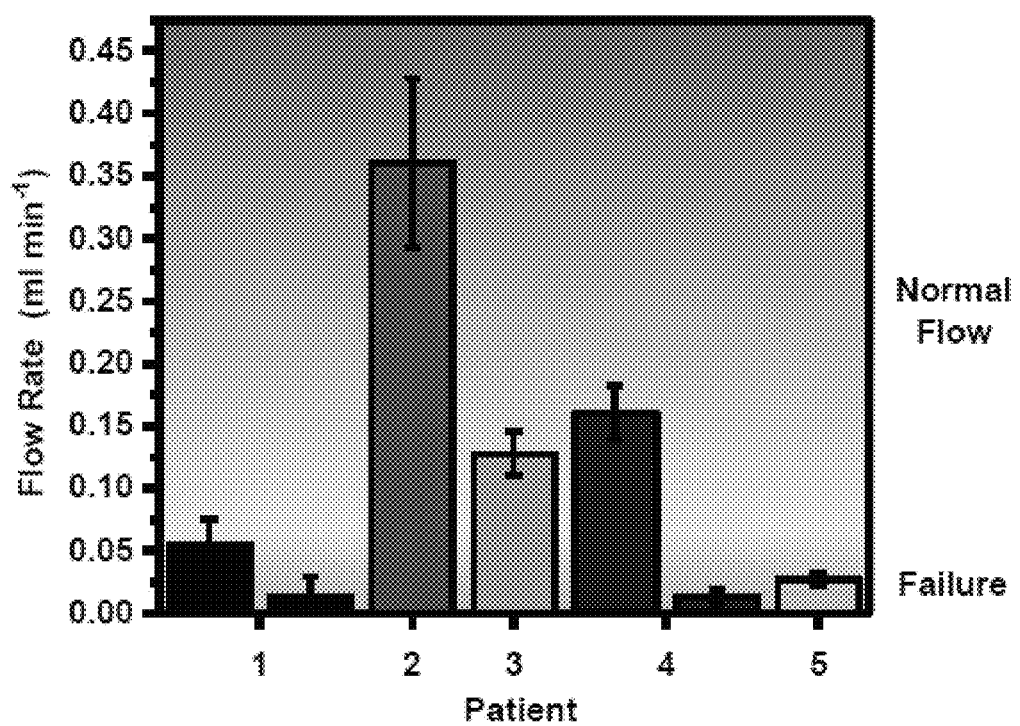
Figure 7D:
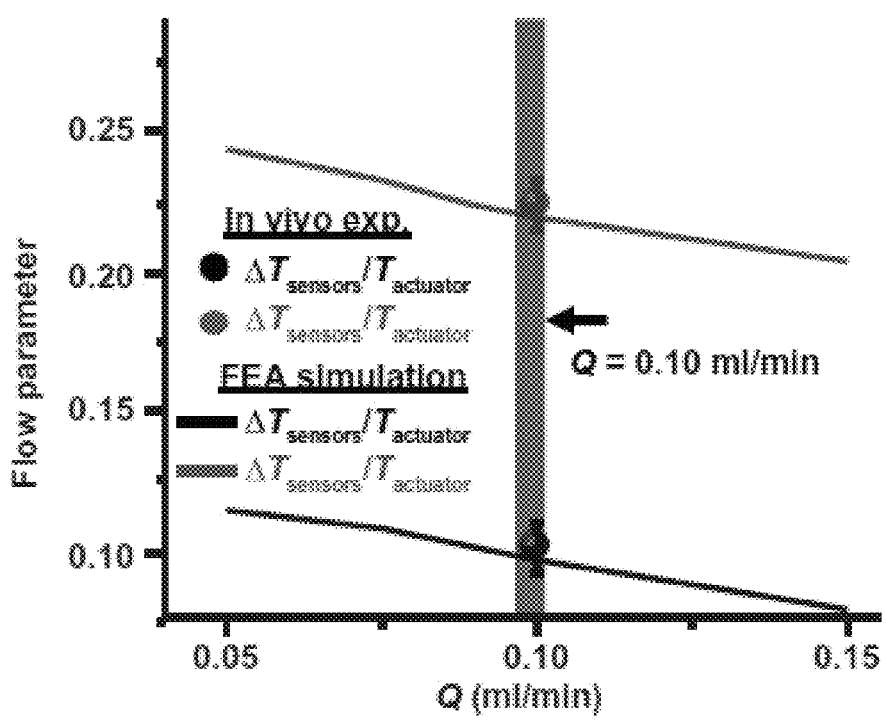

Applications on human subjects illustrate this process. Assessments of Patient 1 prior to corrective surgery, and as in FIGS. 6A-6D, indicated a shunt malfunction, consistent with ELA measurements (0.01∓0.01 mL min$^{-1}$). Measurements after a surgical revision revealed a flow rate of 0.06∓0.02 mL Patients 2 and 3 were not suspected of shunt malfunction and exhibited flow rates of 0.36∓0.04 mL min$^{-1}$ and 0.13∓0.02 mL min$^{-1}$ respectively, well within established ranges for healthy CSF flow [13]. Patient 4, was initially measured to have occluded flow (0.013∓0.002 mL min$^{-1}$). This patient had experienced severe and prolonged constipation for the past week and clinically deteriorated due to a likely pseudo-obstruction. Long term constipation can decrease the resorptive ability of the peritoneum due to increased intraabdominal pressure and a decreased pressure gradient from ventricle to peritoneum [17]. After administering a rigorous bowel regimen, the patient's mental status improved, and a subsequent measurement revealed healthy flow (0.16∓0.02 mL min$^{-1}$). Patient 5 was suspected to have shunt malfunction, and thermal measurements revealed highly occluded flow (0.027∓0.005 mL min$^{-1}$, which was later surgically confirmed. (For these studies, the sensors were not used to make clinical determinations). In patients 4 (pre-bowel examination) and 5 (pre-surgery), the results of the measurements were blinded to the physician assessment. These results appear in FIG. 7C.

Figure 18B:
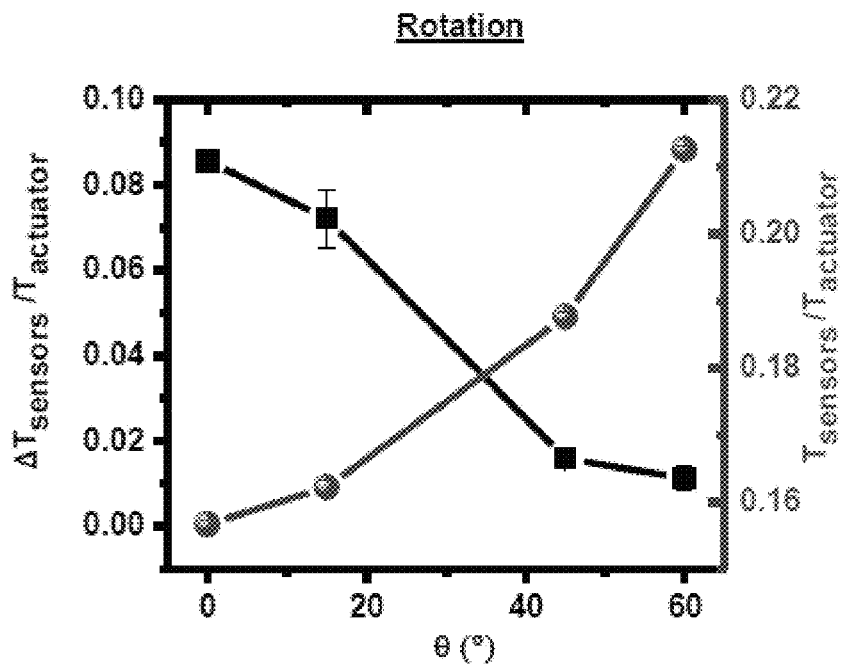
Figure 18C:
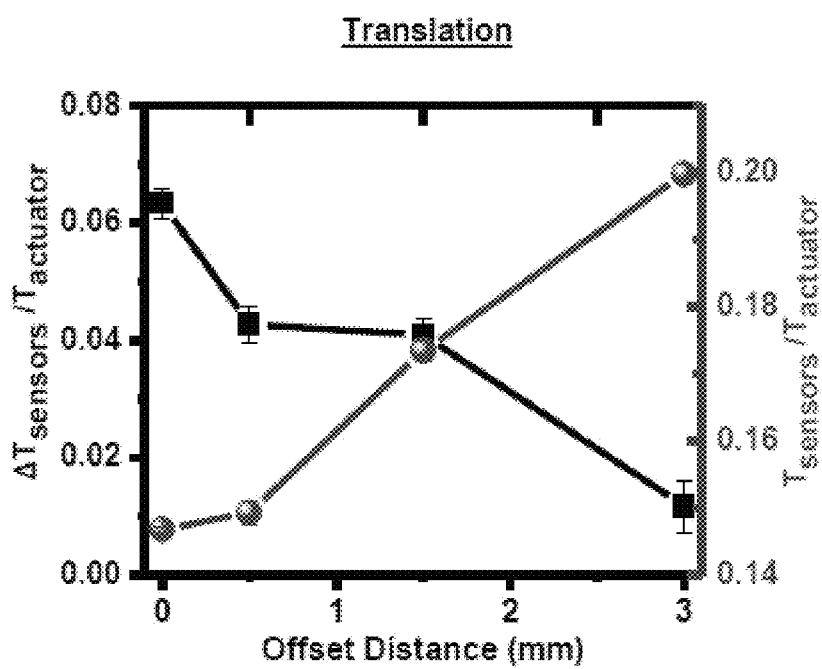
Figure 19A:
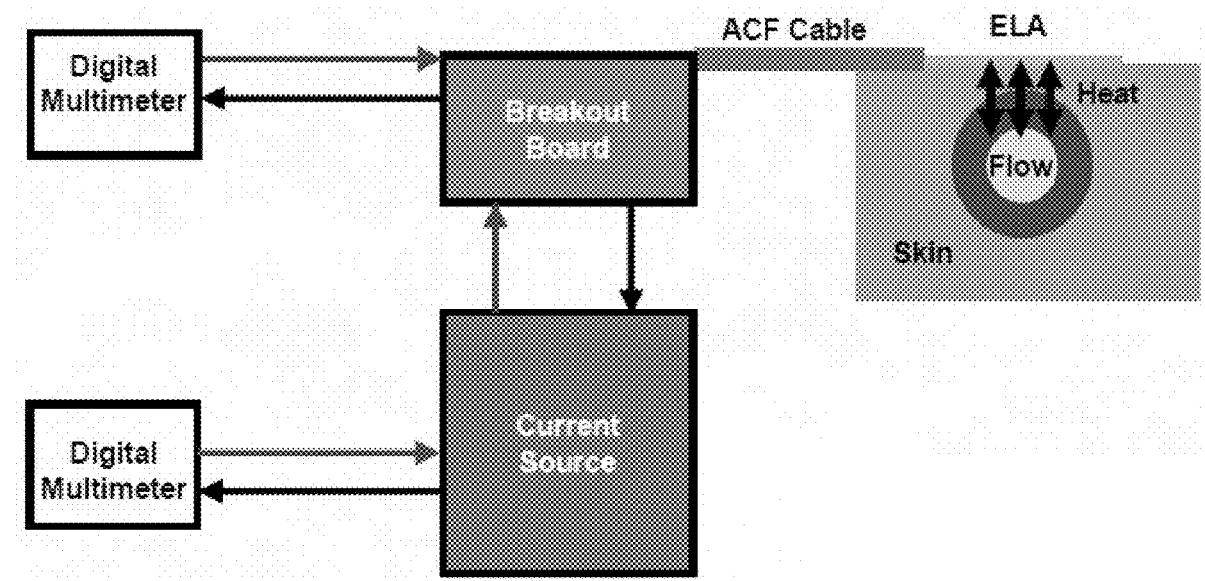
Figure 19B:
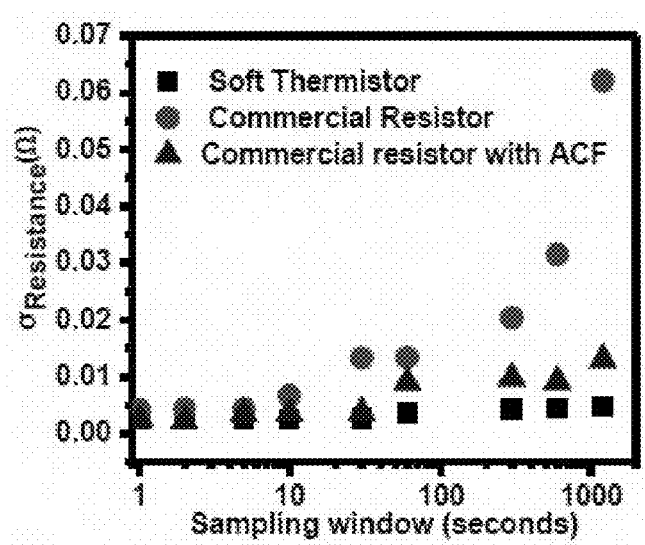
Figure 19E:
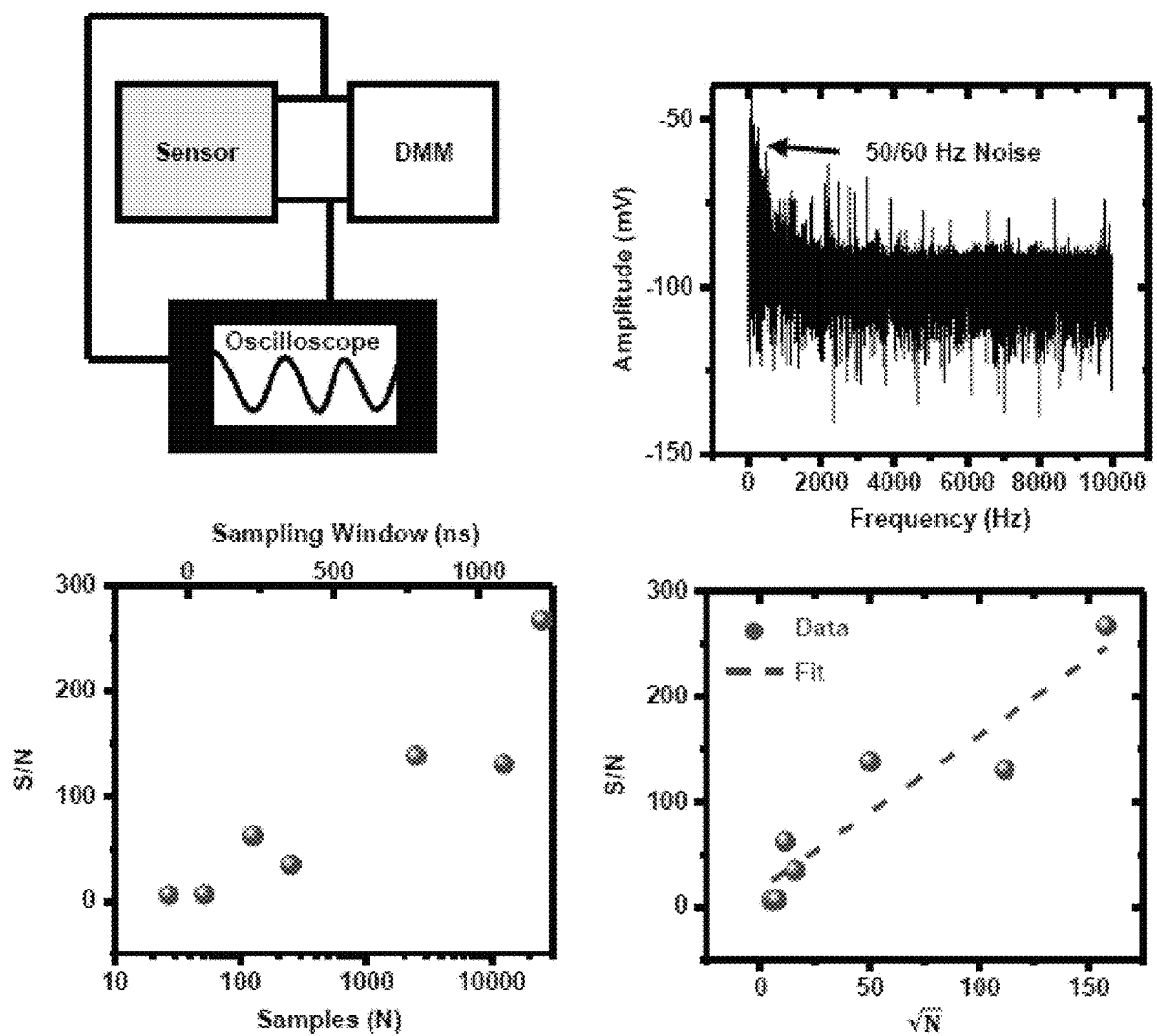
Figure 19F:
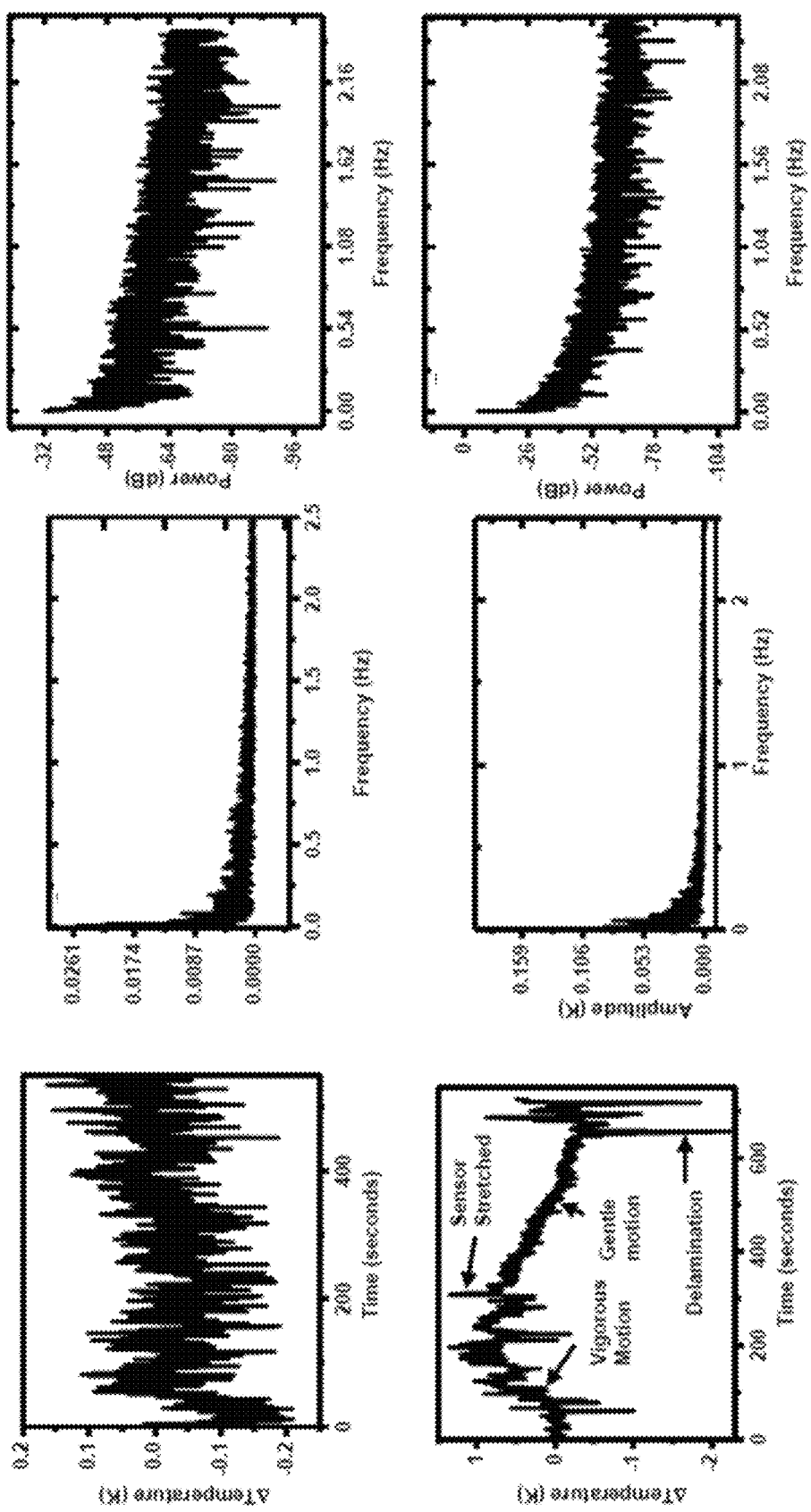

Error, Noise and Uncertainty: Data analysis requires conversion of measured resistances from two sensors and one actuator, first into temperature, and then into a flow rate. A simplified schematic of this process appears in FIG. 18A. The first conversion relies on a precise, high-resolution (10 mf) measurement of resistance performed with a digital multimeter at a sampling frequency of 5 Hz. The inherent noise in the resistance measurement is 4.8 ppm over a 20-minute sampling window, as measured with a commercial, 1 kΩ resistor and shown in FIG. 18B. The addition of a conducting anisotropic thin film (ACF) cable increases the noise to 12.5 ppm. Introducing the soft temperature sensing element and a second ACF connection further increases the noise to 93.9 ppm. Conversion to temperature relies on a linear calibration with $R^2$>0.999, corresponding to a temperature resolution of 15 mK. Actuation involves a high-performance constant current source that exhibits remarkably stable operation, with deviations of 1.73 ppm over a 20-minute sampling window, as shown in FIG. 18C. Taken together with the effects of skin thickness and in-plane heat dissipation, the total noise in measurements of $\Delta T$ sensors/$T_{actuator}$ are ~2%, as shown in FIG. 18D. In practice, strains on the mechanically mismatched ACF cable and soft bond pads induced by patient motion are the primary source of noise, which we measure in vivo, on average, to be 9-10% of the measured $\Delta T_{sensors}/T_{actuator}$ signal for all patients (on on-shunt locations). Elimination of ACF cable, either through wireless embodiments or through thin, soldered connections suggest straightforward ways of mitigating these effects.

Comparison to recent technologies: A commercially available sensor (ShuntCheck) offers an alternative to imaging-based diagnostic tools[18-21]. The system comprises a cooling pack that is held against the skin over the distal catheter, with conventional, bulk temperature sensors attached to the skin downstream, along the direction of the catheter. The pack cools flowing CSF, thereby decreasing the temperature of the downstream sensor. Although this system has high specificity (~100%)[20] and sensitivity (80%), it suffers from key limitations. First, the embodiment is bulky and offers a poorly coupled sensor-skin interface that demands the use of a large pack (2.5 cm×2.5 cm) and significant cooling. This requirement, together with a conventional, large-scale data acquisition (DAQ) system, decreases the usability of the system and prevents continuous, long-term measurements. Second, the measurements are semi-quantitative, without an ability to account for key factors such as skin thickness, skin thermal properties and device layout. Taken together, these factors lead to overall patient discomfort and prevent straightforward interpretation of data[20]. A comparison of existing diagnostic techniques is in FIG. 16.

Implications for the treatment of hydrocephalus: The skin-like, precision sensor systems introduced here have the potential to represent a paradigm shift in clinical diagnostics of shunt malfunction. Compared to radiographic imaging, invasive sampling, and ice-pack cooling, these platforms are unique in their integration of precision, soft, thermal sensors with wireless transmission capability. By exploiting advanced concepts in the measurement of thermal anisotropy and skin-conformal epidermal electronics, these devices can provide further quantitative modes of use beyond opportunities afforded by the embodiments studied here.

Clinically, shunted individuals suffer from prolonged and costly hospital observations, exposure to toxic radiation, painful procedural interventions and discrepancies in socioeconomic care. The current standard of care is a disservice to this vulnerable population, and a better method of diagnosis would be invaluable in the management of hydrocephalic patients. The technology introduced here will introduce capabilities in personalized medicine to the hydrocephalus landscape, currently only embodied by types and settings of generalized valve systems in current treatment. By quantitatively assessing CSF flow rates, baseline flow rates can be established for individual patients after initial surgeries and at follow-up, thereby providing new insights into a patient's hydrodynamic physiology. With an abundance of prior literature describing neurosurgical exploration and witnessed intraoperative flow, such results can shed insights into the levels of flow needed to generate symptoms in vivo. Further, wireless capabilities allow ventricular shunts to be monitored telemetrically, with mobile application development aiding clinical assessment for treating physicians. As value-based healthcare transforms medical environments, precision measurements and seamless wireless transmission will provide an economically practical, clinically effective tool for the clinician. Additionally, the psychological burden of non-specific symptoms creates significant anxiety for patients, families and caregivers. With careful validation, a sensor platform of the type introduced here can be employed in at-home diagnostics, mitigating uncertainty.

Research Applications: Many poorly understood conditions stem from neurological hydrodynamic dysfunction, including normal pressure hydrocephalus (NPH), idiopathic intracranial hypertension (IIH), and slit-ventricle syndrome. These conditions cause tremendous suffering for affected patients. NPH, characterized by a triad of neuropsychiatric changes, urinary incontinence, and gait imbalance, may affect up to 20 million (typically elderly) individuals annually. The associated pathophysiology may be related to choroid villous malabsorption, and overdrainage in these individuals may cause venous rupture and subdural hematoma, often necessitating neurosurgical intervention [Kameda, Lesniak]. IIH predominantly affects younger female patients and has been linked to abnormal Vitamin A metabolism and intracranial venous stenosis. The comparatively diminutive ventricular systems possessed by these patients lead to high risks of shunt malfunction stemming from ventricular collapse, complicating revision surgical attempts and leading to extended, painful hospital stays [McGirt, Karsy, Liu]. Similarly, slit-ventricle syndrome patients experience poor ventricular wall compliance, with malfunctions largely undetectable in radiographic study [Drake]. By understanding individual flow rates in each of these conditions, novel and improved treatment approaches can be developed for their care. Ultimately, personalized, better-designed shunt systems, with integrated flow monitoring systems, will offer the ability to appropriately compensate for these physiological flow patterns, providing hope to a population with significant need.

Fabrication of the sensor system: For the sensors presented here, fabrication began with spin-casting a sacrificial layer of poly(methyl methacrylate) (700 nm) onto a 4", undoped Si-wafer. A dielectric layer, polyimide (PI, 3 µm) is then spun on. For the epidermal linear array (ELA), a single bilayer film of Cr/Au 10/100 nm deposited by electron-beam evaporation onto the wafer, and patterned by photolithography and etching formed the sensors and serpentine interconnects, in accordance with design rules in stretchable electronics [22-25]. For the epidermal square array (ESA), a bilayer film of Cr/Au 10/100 nm was photolithographically defined to form 100 resistive temperature sensing elements, arranged in a 10×10 array, around a central resistive thermal actuator. A multilayer film of Ti/Cu/Ti/Au 20/600/20/25 nm evaporated and photolithographically defined yielded a first layer of rows of serpentine interconnects to address each row of sensors. Photolithography and reactive ion etching (RIE defined via holes in a second, spin-cast layer of PI (3 µm). A second multilayer film of Ti/Cu/Ti/Au 20/600/20/25 nm formed using the same methods as the first, defined columnar serpentine interconnects to address each column. For both the ELA and ESA designs, spin-casting defined a final layer of PI layer (3 µm) also patterned in the geometry of the metal traces. A final RIE step isolated the outline of the device and opened via holes for wired connections to external data acquisition electronics. Immersion in an acetone bath undercuts the sacrificial PMMA layer, allowing for release and transfer via water soluble tape. The devices were then transferred to a thin, bi-layer silicone membrane (Ecoflex, 20 µm, Dow Corning, MG 7 1010 Skin Adhesive, 20 µm), spin-cast onto a glass slide. Immersion in warm water dissolved the tape, and a spin-cast top layer of silicone (Ecoflex, 50 µm) completed the device. A thin (100 µm), double-sided sheet adhesive (JMS 1400, Label Innovations, Ontario, Canada) was laser structured to form an outline around the device. This sheet adhered to the silicone and a handling frame, either in the form of a printed circuit board containing wireless transmission electronics, or a simple, thick, elastomeric frame to facilitate handling of the wired electronics. Anisotropically conducting films (ACF) established connections to wired data acquisition electronics. The sensor resistances were then calibrated to temperatures measured by IR imaging.

Fabrication of Flexible Printed Circuit Boards: Fabrication began with a commercially available, dense, tri-layer Cu/PI/Cu laminate (Pyralux, 6535, DuPont, 18 µm/75 µm/18 µm). Laser structuring (LPKF U4, LPKF Systems, Germany) patterned conducting traces and bond pads, with a resolution of 50 µm. Commercially available SMD resistors, capacitors, along with a Bluetooth microcontroller (NRF 52, Nordic Semiconductor) and battery, in addition to the soft electronic components were bonded to the PCB via reflow soldering.

Data Acquisition Systems: Data were recorded from the ELA resistive elements via digital multimeters (DMM) (NI, USB 4065, National Instruments). Actuation power was supplied with a constant current source (Keithley 6220, Tektronix). The ESA requires a voltage output module (NI 9264, National Instruments) that sequentially actuates each of the ten input channels with 3V, and a single-channel DMM to measure current. A red LED connected in series with each channel served as a visual indicator of multiplexing and the status of each addressed channel. A mechanical REED relay module (J-Works, 2418, J-Works Inc.) was used to time multiplex measurements from each of the ten channels. All data were recorded via custom software designed and programmed in LabView (National Instruments), and processed with custom algorithms in Matlab (Mathworks Inc., Natick, Mass.).

Thermo-Mechanical Modeling and Finite Element Analysis

Figure 13C:
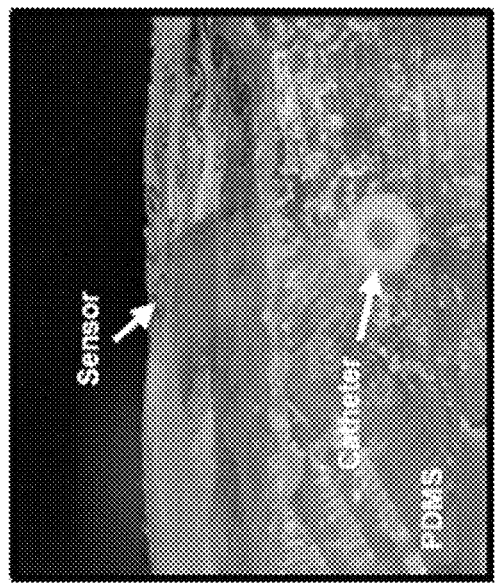
Figure 13B:
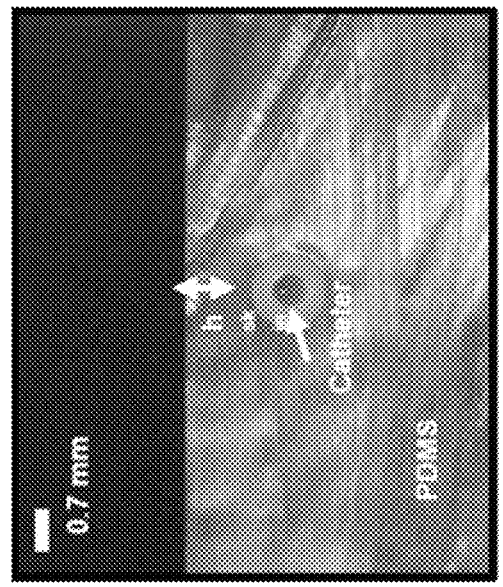
Figure 14:
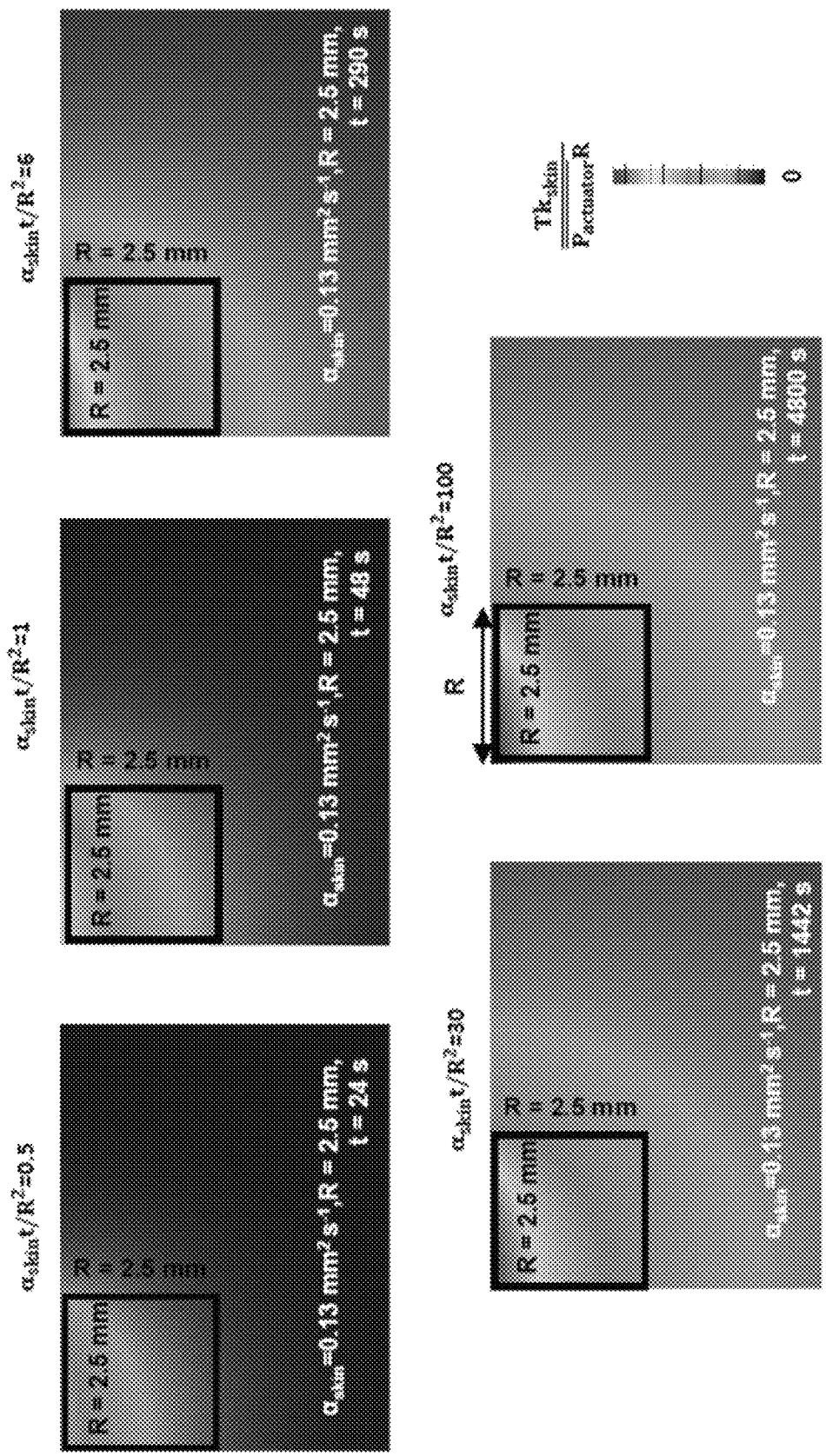
FIG. 14. Finite element simulations of dimensionless scaling parameters illustrating time evolution of heat through skin, as a measure of depth penetration, with experimentally measured numbers from the system overlaid.

Benchtop Experiments: A phantom skin assembly was constructed for in-vitro evaluation. A distal shunt catheter (Medtronic, Minneapolis, Minn.) was embedded in a matrix of PDMS (Sylgard 184, Dow Corning) supported by a 3D printed mold containing struts to preventing sagging of the catheter. Optical images of this assembly appear in FIGS. 13A-13C. The depth of the catheter under the PDMS was 1.1 mm, as seen in FIG. 13B, and the sensor was laminated onto the free surface of the assembly, as shown in FIG. 13C. The catheter was connected to a syringe pump, through which flow rates were varied to yield the experimental data shown in FIGS. 3A-3K. Water was chosen to be the test fluid for these experiments. The observed flow rates were 33% higher than values displayed on the pump, which was corrected for via a simple, linear calibration, where true flow values were measured with precise weight measurements on an analytical balance at fixed time intervals. The syringe pump was allowed to come to steady state at a flow rate for 180 s before the measurement was made. Each measurement consisted of a 60 s "off" period with $Q_{actuator}$<0.001 mW/mm$^2$, followed by a 600 s actuation ("on") period, with $Q_{actuator}$=1.45 mW/mm$^2$, followed by a 180 s off period to return the sensor back to its baseline, pre-actuation temperature value.

Simultaneously, thermographs were recorded with an IR Camera (FLIR Systems, a6255sc), with a high-magnification lens. Different skin-thicknesses were achieved by casting PDMS onto 3D printed molds with negative relief structures with defined heights and laminating the resulting sheets onto the fluidic assembly described above.

Human Study Design: Patients were recruited from an existing ICU population. The inclusion criterion was any patient with an implanted ventricular shunt, regardless of whether they were suspected of shunt malfunction. Patient 1 (36, F) presented with a Pseudotumor cerebri and suspected shunt malfunction that was then surgically corrected. Patient 2 (F, 53) presented with a Chiari I malformation, and was not suspected of shunt malfunction. Patient 3 (M, 32), presented with a Glioblastoma multiform, with no suspected malfunction, and Patient 4 (F, 58) presented with a Glioblastoma multiforme with suspected pseudoobstruction due to acute and prolonged constipation that was resolved with a rigorous bowel examination. Patient 5 (F, 30) presented with suspected malfunction due to obstruction, with severely diminished but non-zero flow, which was confirmed during surgery. Depending on the clinical condition of the patient, they were either asked to either sit at 45° or completely supine. A single measurement consisted of placing the sensor on the skin and waiting for 60 s for the sensor to equilibrate with the skin. Low power thermal actuation (1.6 mW/mm$^2$) was then supplied for 240 s, and then halted for the next 120 s, while making continuous temperature measurements of both the sensors and the actuator. All data recording occurred at 5 Hz and processing used an adjacent-averaging filter with a 10-point sampling window. Two successive measurements each were made on skin directly overlying the shunt, and at a skin location adjacent to the shunt. The shunt was easily located, and alignment marks on the device allowed for easy alignment. An elastomeric enclosure around the device facilitated handling of the device.

TABLE 1

Table summarizing etiology of, and measurements made on each patient.

| | Underlying Condition | Age | Sex | Malfunction Present | Flow Detected (pre-intervention) | Flow Detected (post-intervention) | Imaging Correlate | Skin Irritation |
|---|---|---|---|---|---|---|---|---|
| 1 | Pseudotumor cerebri | 36 | F | Y | N | Y | Y[1] | N |
| 2 | Chiari I malformation | 53 | F | N | Y | N/A | N/A | N |
| 3 | Glioblastoma multiforme | 32 | M | N | Y | N/A | N/A | N |
| 4 | Glioblastoma multiforme | 58 | F | Y | N | Y | Y[2] | N |
| 5 | Post-hemorrhagic | 30 | F | Y | Y | N/A[3] | Y[4] | N |

TABLE 2

Table summarizing existing shunt diagnostic tools and techniques.

| Modality | Cost | Time (min) | Sensitivity | Specificity | PPV | NPV |
|---|---|---|---|---|---|---|
| X-Ray [1,2] | 440 | 84 | 4-26% | 92-99% | 13 | 93.9 |
| CT [3-6] | 1323 | 83 | 54-80% | 80-90% | 71 | 90.8 |
| MRI [5-8] | 3239 | 115 | 40-62.8% | 84-92% | 75 | 86.5 |
| RSPS [9-12] | 750 | 45 | 47-65% | 86-92% | 71 | 71 |
| ShuntCheck [13-15]* | Unknown | 360 | 80% | 100% | 58 | 96 |

REFERENCES

1. Xu, S., et al., Soft microfluidic assemblies of sensors, circuits, and radios for the skin. Science, 2014. 344 (6179): p. 70-74.
2. Norton, J. J., et al., Soft, curved electrode systems capable of integration on the auricle as a persistent brain—computer interface. Proceedings of the National Academy of Sciences, 2015. 112(13): p. 3920-3925.
3. Kim, J., et al., Epidermal electronics with advanced capabilities in near-field communication. small, 2015. 11(8): p. 906-912.
4. Dagdeviren, C., et al., Conformal piezoelectric systems for clinical and experimental characterization of soft tissue biomechanics. Nature materials, 2015. 14(7): p. 728-736.
5. Choi, J., et al., Thin, Soft, Skin-Mounted Microfluidic Networks with Capillary Bursting Valves for Chrono-Sampling of Sweat. Advanced healthcare materials, 2017. 6(5).
6. Koh, A., et al., A soft, wearable microfluidic device for the capture, storage, and colorimetric sensing of sweat. Science translational medicine, 2016. 8(366): p. 366ra165-366ra165.
7. Tian, L., et al., Flexible and Stretchable 3ω Sensors for Thermal Characterization of Human Skin. Advanced Functional Materials, 2017.
8. Krishnan, S., et al., Multimodal epidermal devices for hydration monitoring. Microsystems & Nanoengineering, 2017. 3: p. 17014.
9. Zhang, Y., et al., Theoretical and Experimental Studies of Epidermal Heat Flux Sensors for Measurements of Core Body Temperature. Advanced healthcare materials, 2016. 5(1): p. 119-127.
10. Webb, R. C., S. Krishnan, and J. A. Rogers, Ultrathin, Skin-Like Devices for Precise, Continuous Thermal Property Mapping of Human Skin and Soft Tissues, in Stretchable Bioelectronics for Medical Devices and Systems. 2016, Springer. p. 117-132.
11. Webb, R. C., et al., Thermal transport characteristics of human skin measured in vivo using ultrathin conformal arrays of thermal sensors and actuators. PLoS One, 2015. 10(2): p. e0118131.
12. Webb, R. C., et al., Epidermal devices for noninvasive, precise, and continuous mapping of macrovascular and microvascular blood flow. Sci Adv, 2015. 1(9): p. e1500701.
13. Hidaka, M., et al., Dynamic measurement of the flow rate in cerebrospinal fluid shunts in hydrocephalic patients. European Journal of Nuclear Medicine, 2001. 28(7): p. 888-893.
14. Carslaw, H. S. and J. C. Jaeger, Conduction of heat in solids. Oxford: Clarendon Press, 1959, 2nd ed., 1959.
15. Sandby-Moller, J., T. Poulsen, and H. C. Wulf, Epidermal thickness at different body sites: relationship to age, gender, pigmentation, blood content, skin type and smoking habits. Acta Dermato Venereologica, 2003. 83(6): p. 410-413.
16. Braley, S., The chemistry and properties of the medical-grade silicones. Journal of Macromolecular Science-Chemistry, 1970. 4(3): p. 529-544.
17. Martinez-Lage, J. F., et al., Severe constipation: an under-appreciated cause of VP shunt malfunction: a case-based update. Child's Nervous System, 2008. 24(4): p. 431-435.
18. Ragavan, V. V., Evaluation of shunt flow through a hydrocephalic shunt: a controlled model for evaluation of the performance using Shuntcheck. 2017: p. 1-4.
19. Boyle, T. M., J; Neuman, M; Tamber, M; Hickey, R W; Heuer G, Leonard J; Leonard J C, Keating R; Chamberlain J; Frim I D, Zakrzewski, Klinge, P; Merck, L; Platt, J; Bennett, J; Sandberg, I D, Boop, Zorc, J, ShuntCheck versus Neuroimaging for Diagnosing Ventricular Shunt Malfunction in the Emergency Department. American Association of Pediatrics, 2017: p. 1-2.
20. Madsen, J. R., et al., Evaluation of the ShuntCheck Noninvasive Thermal Technique for Shunt Flow Detection in Hydrocephalic Patients. Neurosurgery, 2011. 68(1): p. 198-205.
21. Recinos, V. A., E; Carson, B; Jallo, G, Shuntcheck, A Non-invasive Device To Assess Ventricular Shunt Flow: One Institution's Early Experience. American Association of Neurological Surgeons, 2009. Abstract: p. 1-1.
22. Zhang, Y., Y. Huang, and J. A. Rogers, Mechanics of stretchable batteries and supercapacitors. Current Opinion in Solid State and Materials Science, 2015. 19(3): p. 190-199.
23. Zhang, Y. H., et al., Experimental and Theoretical Studies of Serpentine Microstructures Bonded To Pre-strained Elastomers for Stretchable Electronics. Advanced Functional Materials, 2014. 24(14): p. 2028-2037.
24. Zhang, Y., et al., Mechanics of ultra-stretchable self-similar serpentine interconnects. Acta Materialia, 2013. 61(20): p. 7816-7827.
25. Zhang, Y., et al., Buckling in serpentine microstructures and applications in elastomer-supported ultra-stretchable electronics with high areal coverage. Soft Matter, 2013. 9(33): p. 8062-8070.

Example 2: System Characterization and Use

Figure 24:
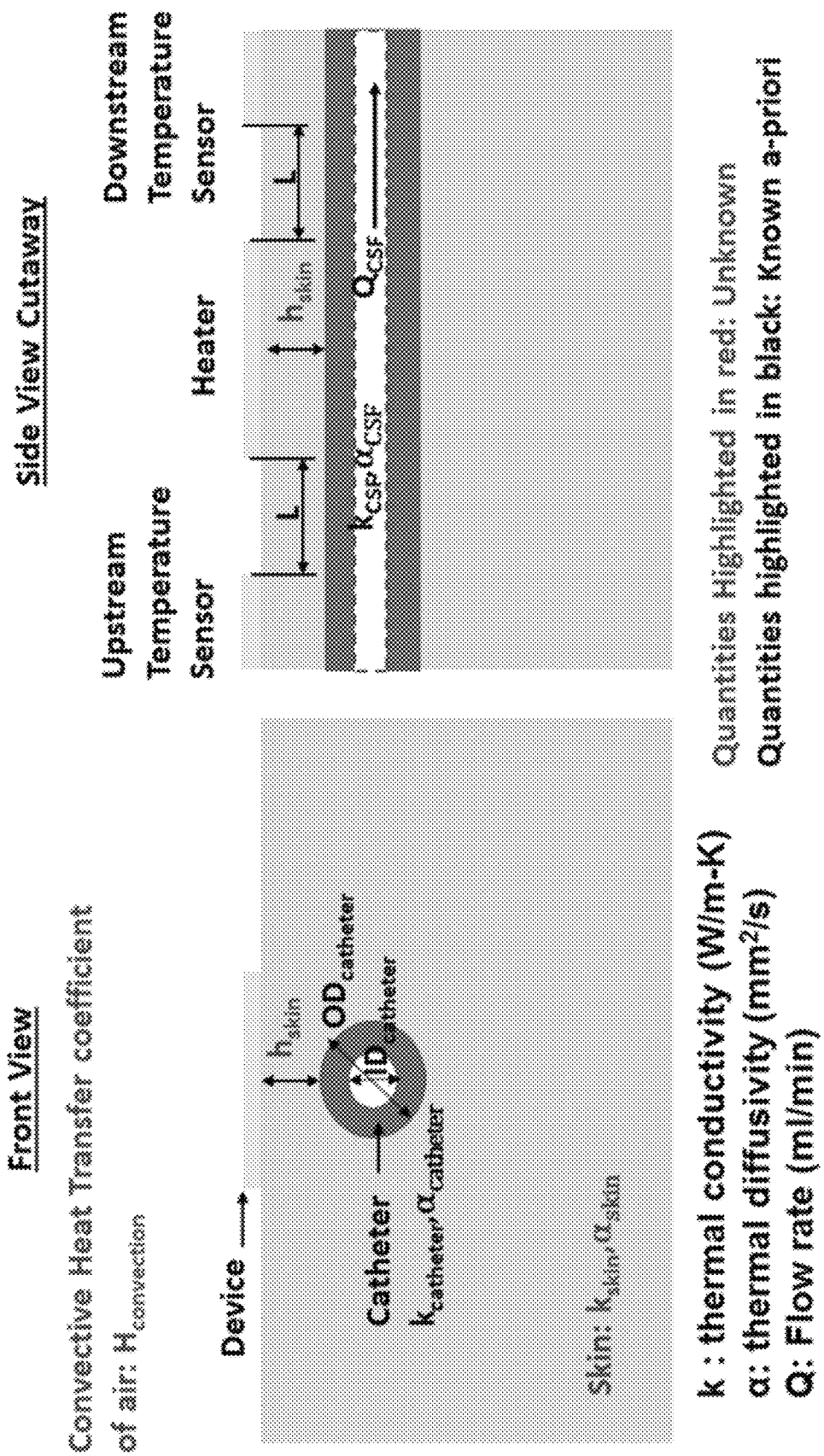
FIG. 24. Schematic illustration of relevant parameters.
Figure 25:
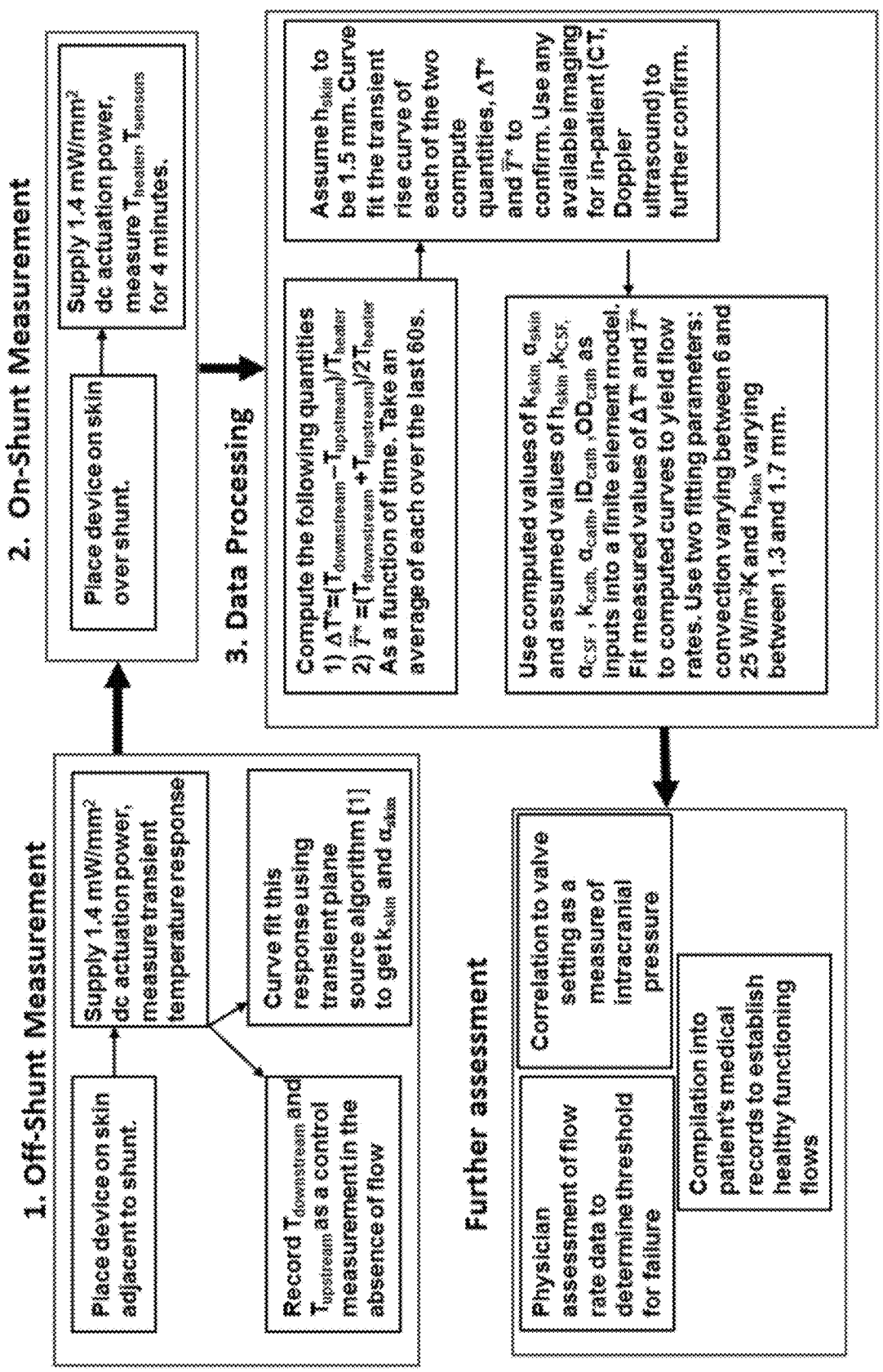
FIG. 25. Flow-chart summary of flow rate determination using any of the devices described herein.

FIGS. 24-28 illustrate various features of the devices and methods described herein. FIG. 24 illustrates the position of the device and temperature sensors and various parameters used to calculate temperature and flow-rate in a subdermal conduit (described in FIG. 24 as "catheter"). Unknown quantities include skin-related parameters, such as depth of the conduit from the skin surface ($h_{skin}$), as well as thermal conductivity (k) and diffusivity (α) of the skin. Known parameters include the thermal conductivity (k) and diffusivity (α) of the conduit and fluid in the conduit, outer and inner diameters of the conduit, and upstream, downstream distance between the sensors and the actuator (labeled "heater"), and temperature measured by the sensor and applied by the heater. In controlled conditions, the flow-rate (Q) of the fluid in the conduit may be known. From these parameters, flow-rate may be determined, as summarized in the flow-chart of FIG. 25.

Figure 26:
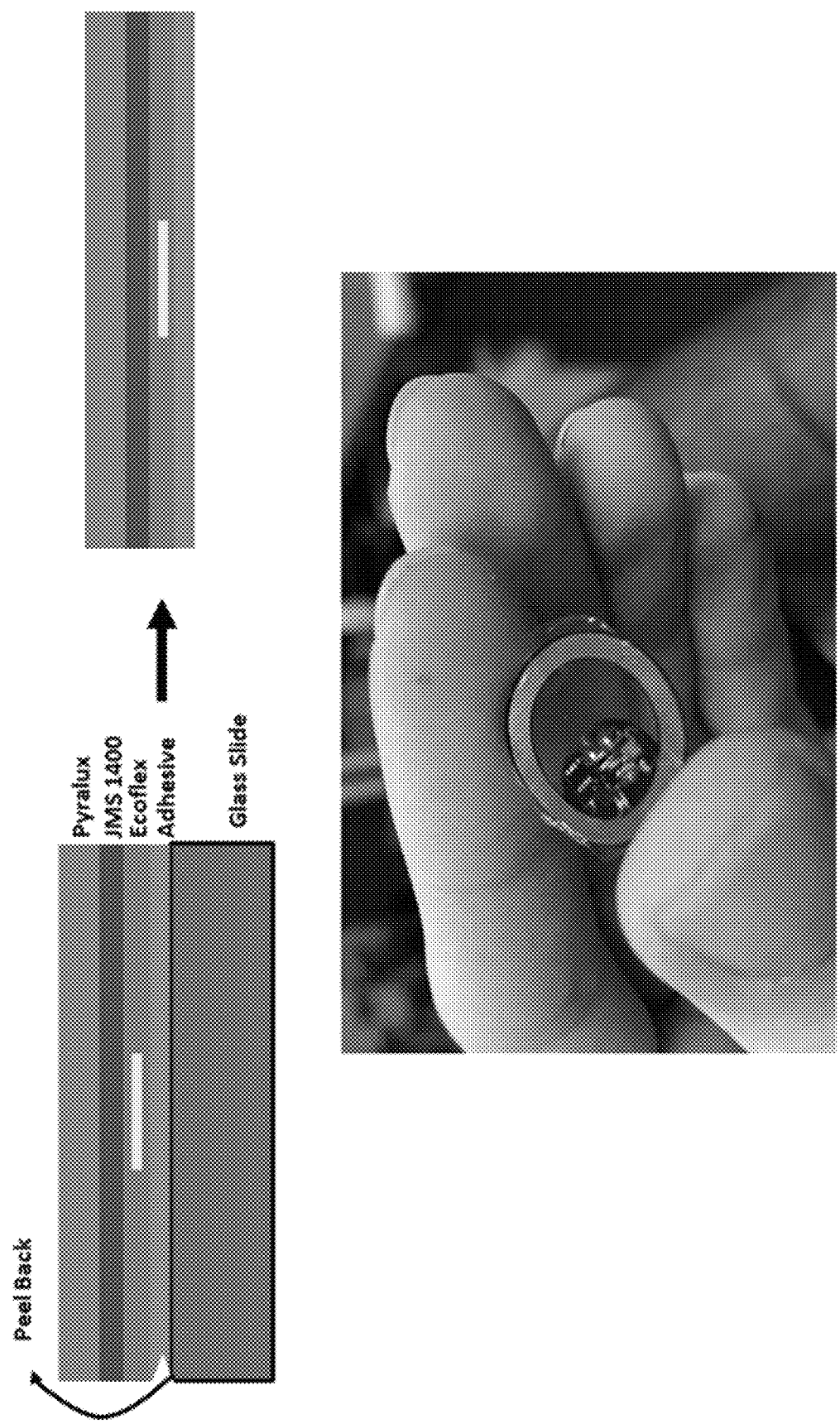
FIG. 26. Illustration of carrier and handling layer, with the device peeled back and away from the rigid handling layer of glass.

The active sensing portion of the device is extremely thin and, therefore, relatively difficult to handle. To assist with handling, any of the devices described herein may have a handle layer, including as shown in FIG. 26. A rigid layer, such as a glass slide, may support any of the devices described herein, including with an adhesive layer and encapsulation layers. The device may be peeled off the handle layer and be ready for conformal contact with the skin.

Figure 28:
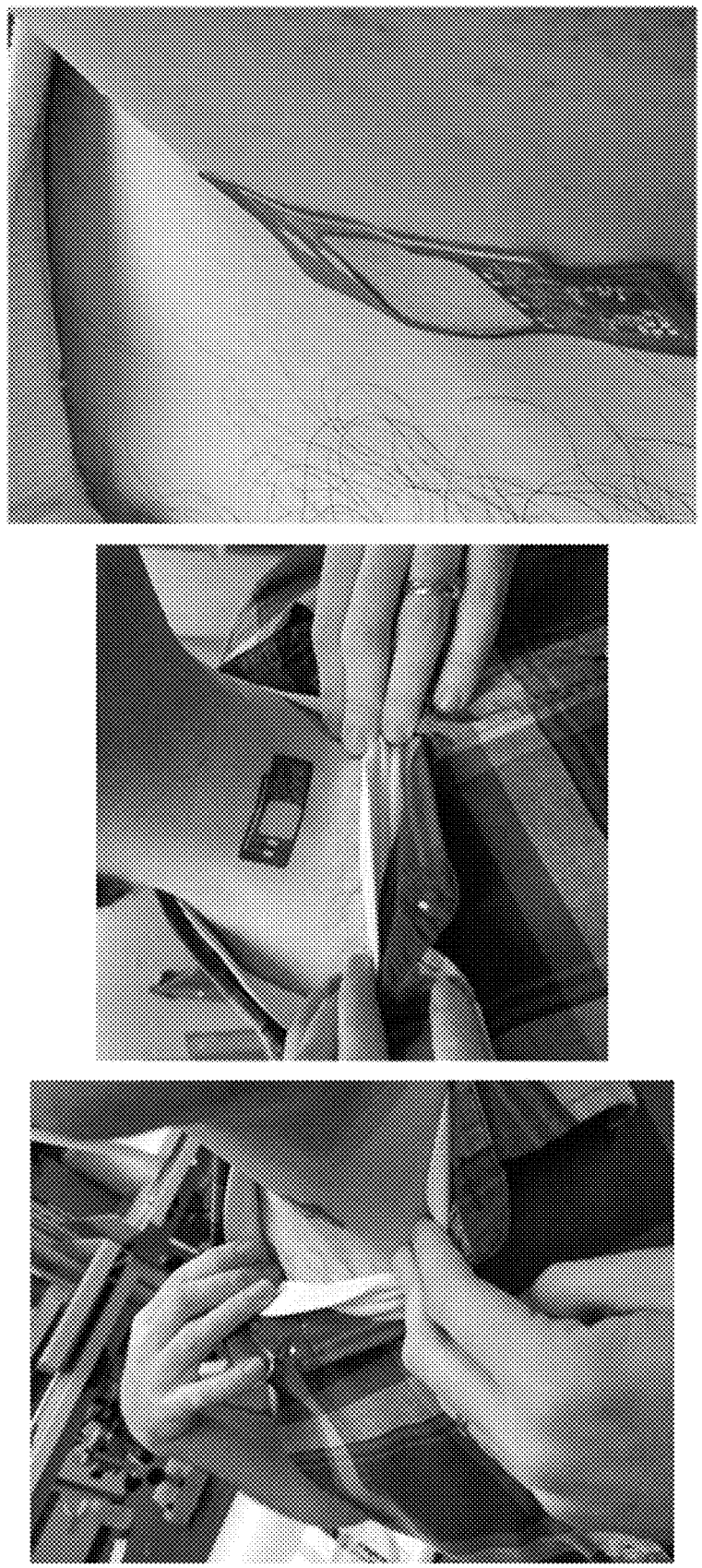
FIG. 28. Another illustration showing the handling substrate with an opening where the active sensing portion of device may be positioned.

FIGS. 27-28 illustrate a carrier substrate having an open passage through a central portion of the carrier substrate, wherein the conformable device is positioned in the open passage to provide improved handling characteristics during application and durability during use. The carrier substrate in FIG. 27 is circular, and in FIG. 28 is rectangular. Any number of shapes may be used, including depending on the application and location of interest.

The sensor described herein has many potential applications in wide range of applications, including in the medical field. For example, bypass vascular grafts, and cardiac stent flow may be assessed post-procedurally. This involves placing a sensor over an applicable area with appropriate depth and quantifying flow parameters. Similarly, sensors applied over large vessels may be used to assist in detecting microemboli pertinent to the management of diseases such as carotid atherosclerotic disease. Finally, appropriate pressure readings may be invaluable in providing non-invasive arterial pressure measurements in the operating room or angiography suite, abrogating the need for invasive arterial line placement.

Example 3: Soft Tissue Mounted Flow Sensors

Abstract

Hydrocephalus and shunt-related expenditures cost the US system over $2 billion dollars in annual expenses, with 125,000 shunt surgeries per year and an untreated mortality rate estimated at 50-60%. Existing diagnostics are expensive, inaccurate, and often harmful or invasive, and can lead to unnecessary admissions, further testing, or needless surgery. Collaborative efforts between Northwestern materials engineers headed by Dr. John Rogers alongside the leadership of neurological surgeons at Northwestern Memorial Hospital and Lurie Children's Hospital have produced and validated a noninvasive, thermal biosensor capable of diagnosing ventricular shunt malfunction.

Applications

Non-invasive, rapid, accurate detection of shunt malfunction

Conformal, painless sensor technology with wireless capability

Extended use can capture occult malfunction, akin to a holter monitor for cerebrospinal fluid Advantages Minimal devices with similar capabilities in market currently Present analogues (i.e.: Shuntcheck) require use of ice cubes, cumbersome technology and supplementary devices Provides minimal, sensitive and rapid detection of flow through silastic tubing Components and manufacturing flows that are compatible with existing scalable, ISO:13485 compliant approaches

BRIEF SUMMARY OF TECHNOLOGY

Provided herein are devices that allow for the sensing of fluid flow through near-surface conduits, both natural and implanted. Examples of these conduits include near-surface blood vessels such as veins and arteries, and implanted silicone shunt catheters for the drainage of excess cerebrospinal fluid in patients with hydrocephalus. The sensor relies on measurements of thermal transport through the skin, owing to the fact that near-surface flow affects thermal transport, causing heat from a localized heat source to flow preferentially along the direction of flow. Earlier disclosures have covered concepts relevant to hydrocephalus diagnostics. This disclosure describes technologies for advanced clinical deployment, manufacturability and usability by patients and physicians alike. A feature of the technologies described below is their immediate relevance to clinical deployment. Specifically, the components and technologies described below are compatible with scalable, ISO:13485 compliant manufacturing approaches, and the key features described are informed by patient trials. These advances are important to any related technology seeking regulatory clearance, for example in the form of a pre-market approval (PMA) or 510(k) from the federal food and drug administration.

Technical Description

Figure 29:
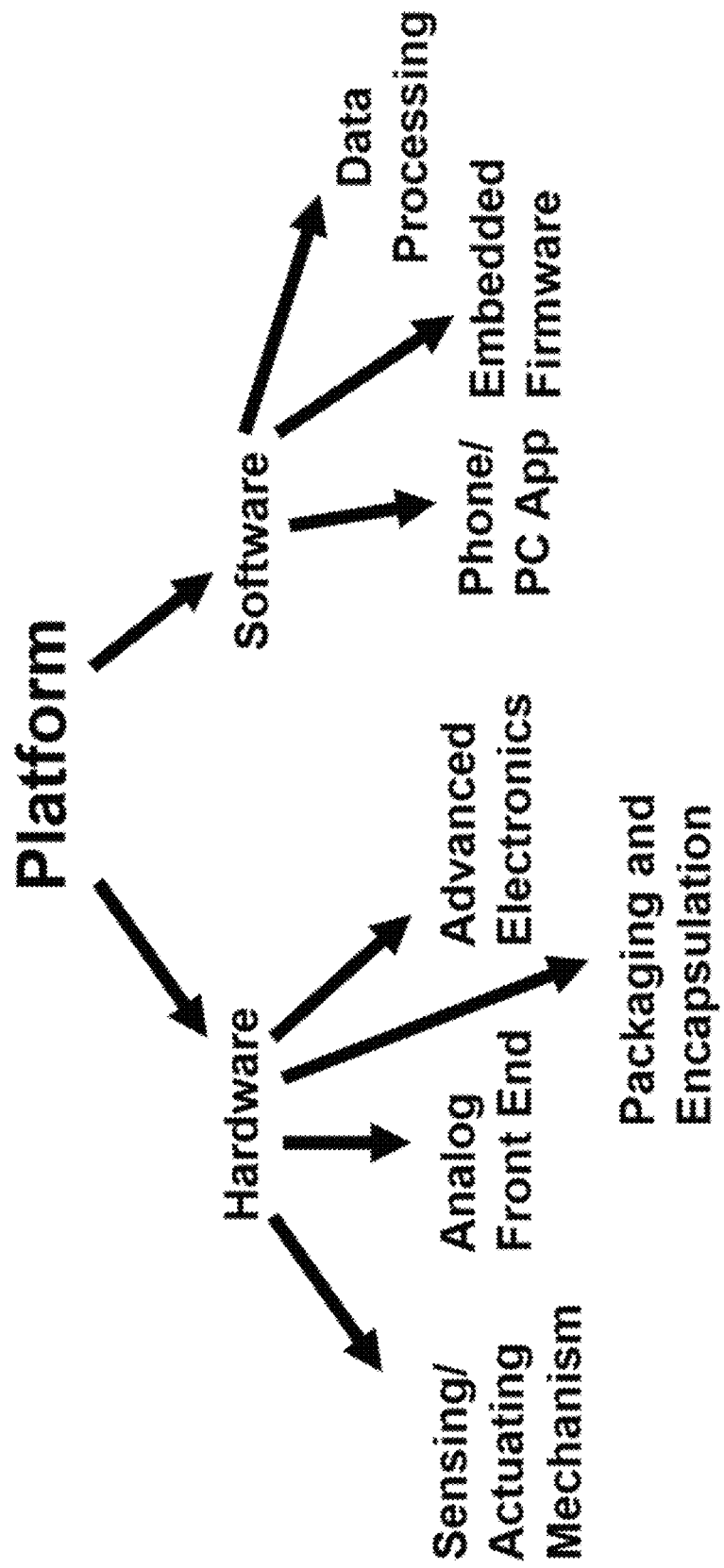
FIG. 29. provides an overview of the sensing platform technology, including hardware and software.

FIG. 29 provides an overview of new platform technologies and various aspects of the systems and methods described herein.

Sensing/Actuating Hardware

As an example, the sensing hardware involves collections of thermal actuators (e.g., heating elements) and temperature sensors with layouts and form factors that allow them to map heat flow across the skin to reveal near-surface flows and their magnitudes at depths of up to 8 mm. Their form factors also allow them to couple closely to the skin, with low thermal masses and interfacial resistances. We describe three distinct technologies that allow this:

Thin film electronic actuators/sensors: These describe any technologies capable of responding specifically to changes in temperature with changes in their electronic properties, or capable of inducing localized temperature changes on demand, with total thicknesses of <10 µm. Examples of sensing mechanisms include piezoresistive sensors constructed from metals or semiconducting materials, that can exhibit either a positive or negative correlation with changes in temperature, and diodes which exhibit temperature-dependent turn-on voltages. Examples of actuating elements include metallic heating coils constructed from metals or their alloys, that exhibit joule heating on the application of current.

Figure 30:
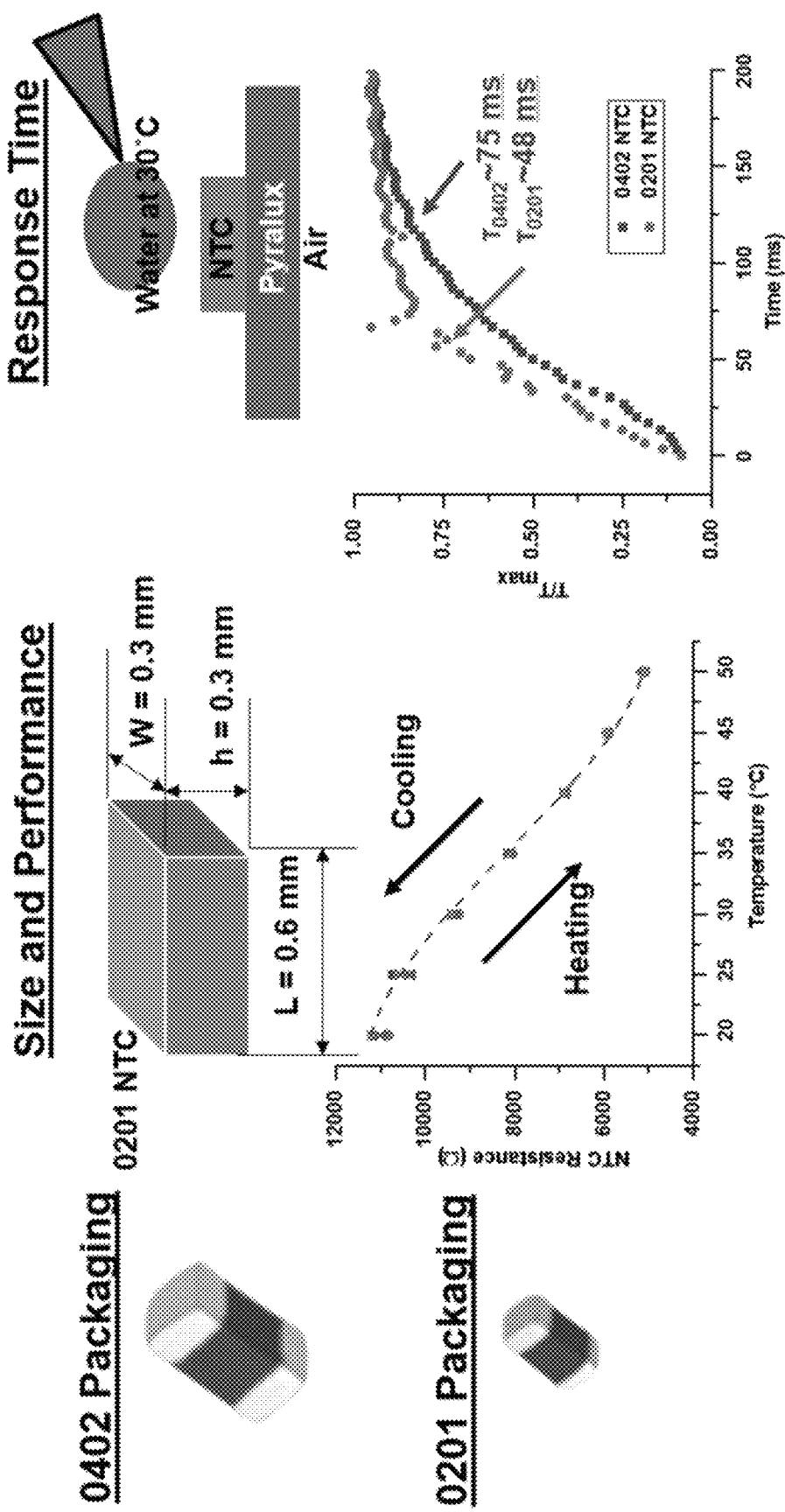
FIG. 30. illustrates an example sensor design for commercial, surface mounted temperature sensors.
Figure 31:
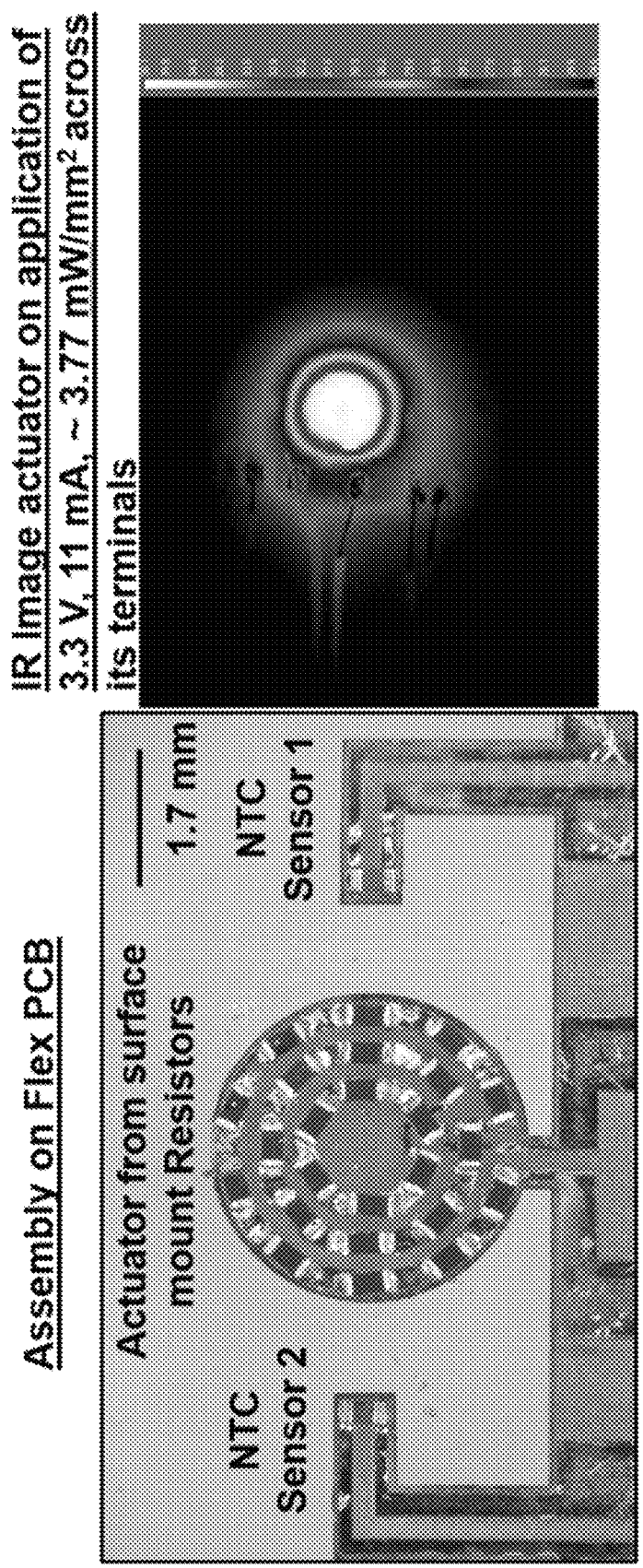
FIG. 31. provides an example of a flexible printed circuit board (PCT) based flow sensor including thermal actuation by an array of resistive elements.
Figure 35:
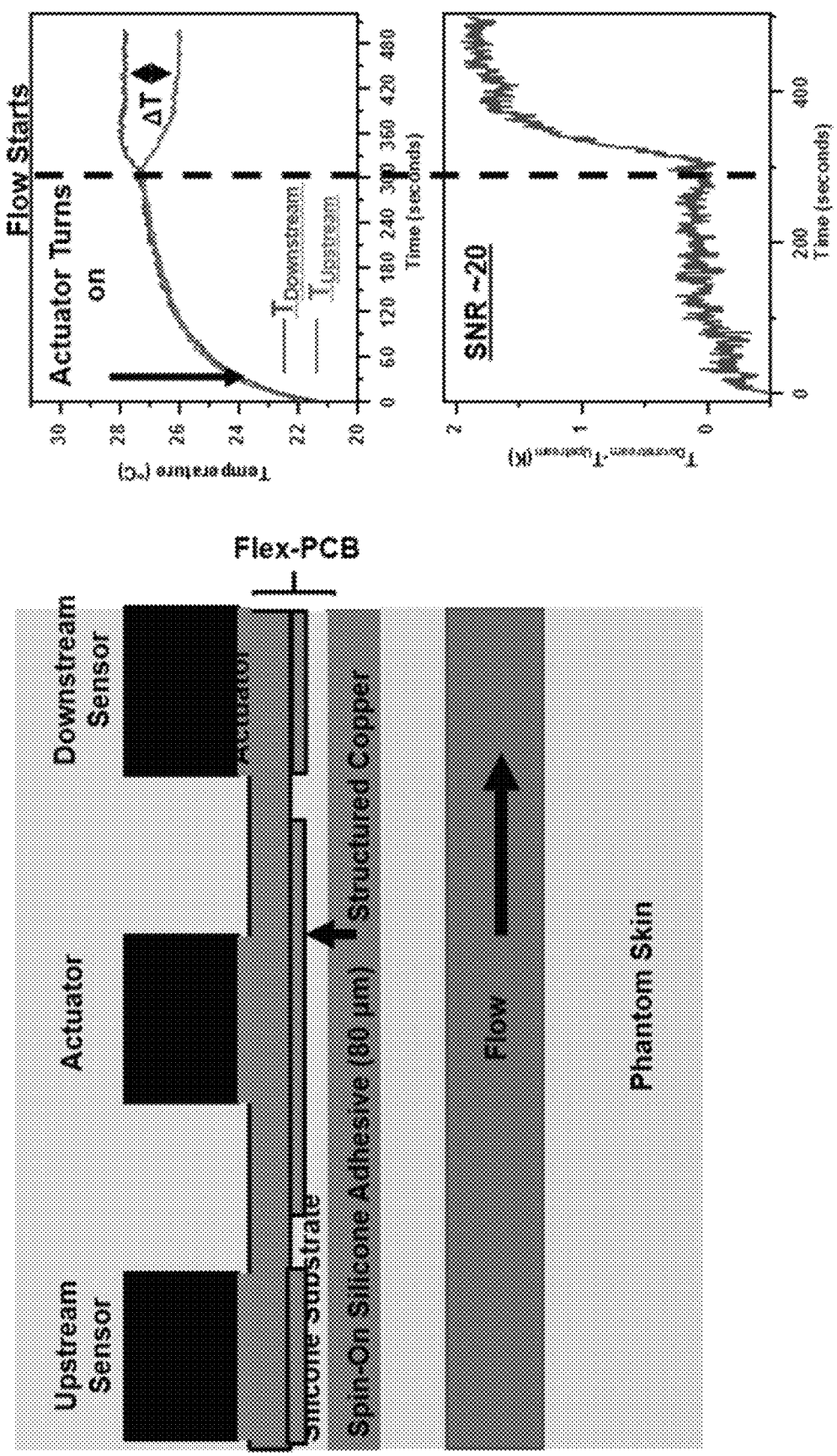
FIG. 35. provides an example of in vitro testing of a surface-mount device ad described herein without foam insulation.
Figure 36:
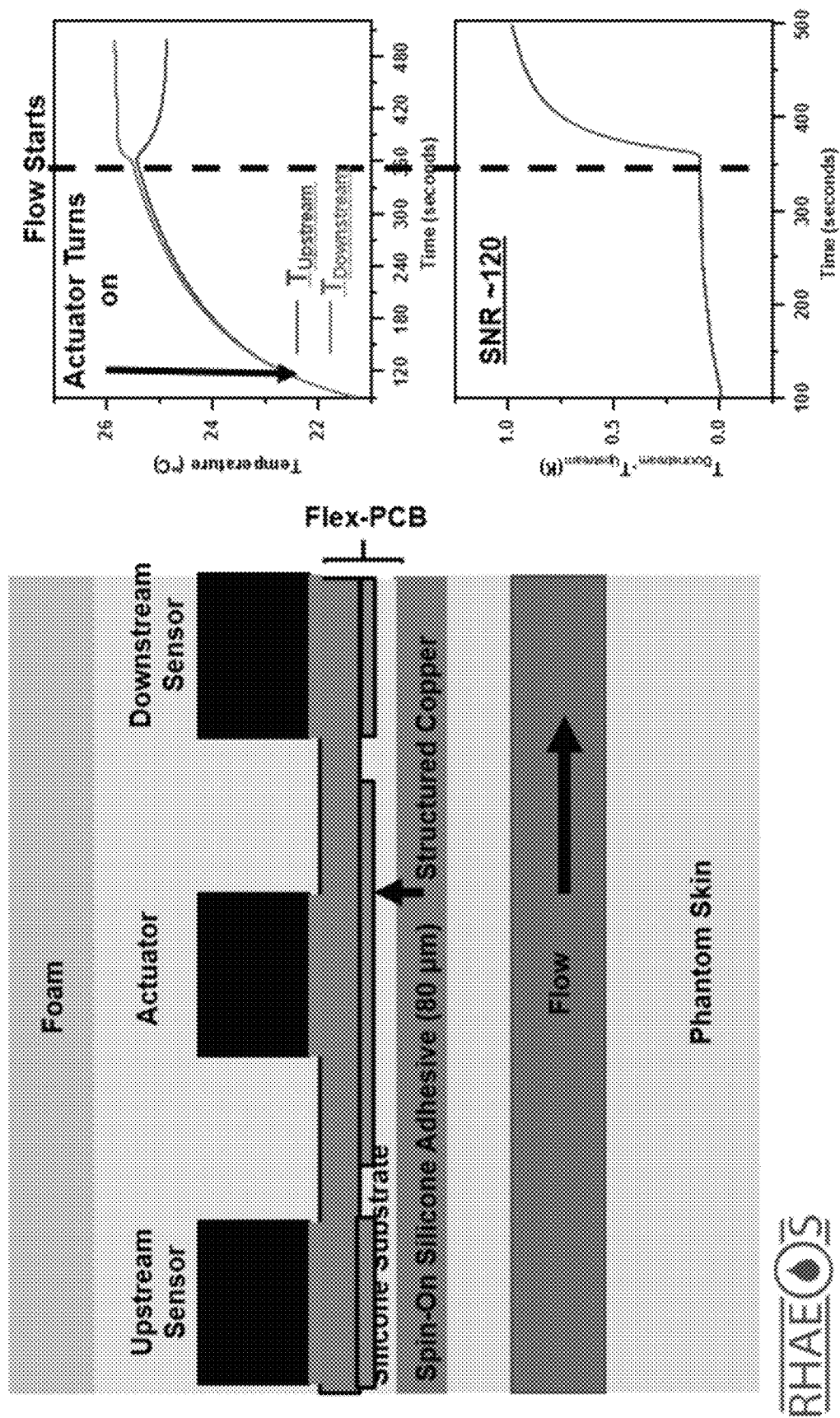
FIG. 36. provides an example of in vitro testing of a surface-mount device ad described herein with a foam insulation layer, illustrating the increase in signal to noise ratio provided by insulation.
Figure 37:
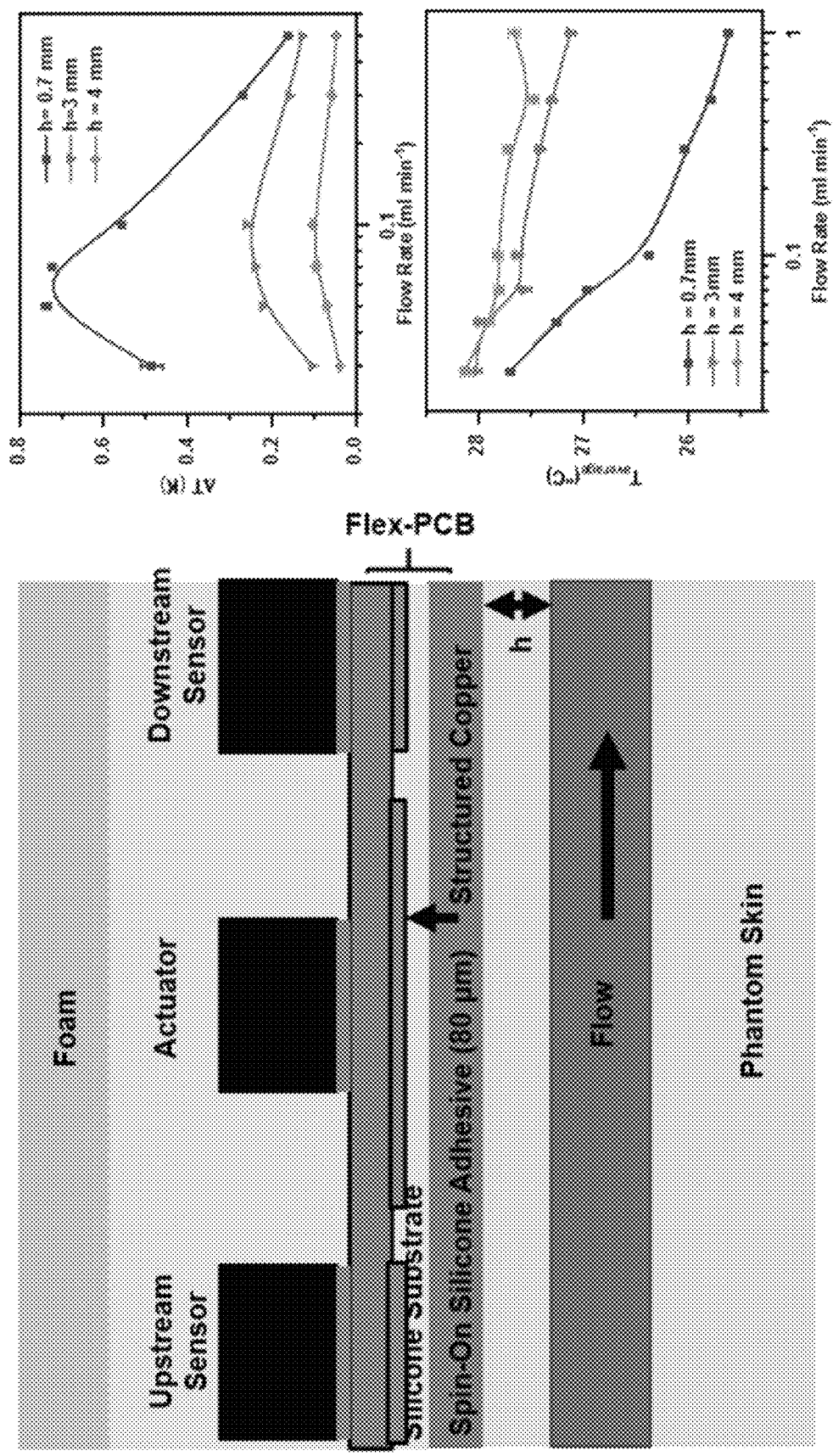
FIG. 37. provides in vitro testing of a surface-mount device with foam insulation across flow rates and relevant skin thicknesses, including a discontinuous thermally conductive layer positioned proximate to the thermal actuator and sensors.

Commercial surface-mount technologies: These describe miniaturized commercial components for temperature sensing and thermal actuation. Examples of temperature sensing technologies include positive-temperature coefficient (PTC) and negative temperature coefficient (NTC) temperature sensors, typically in surface-mounted, lightweight form-factors that allow for low thermal mass sensing, and can be easily integrated with flexible circuit boards via reflow soldering or commercial pick and place technologies. They are in some cases constituted of metals, metal oxides and polymers, and are commercially available for a range of sensing applications from the automotive industry to manufacturing. The typical sizes of these sensors are 1200 µm×600 µm×600 µm or less. They exhibit temperature response times that are <100 ms, and are precise to temperature changes of 50 mK or better. These results are characterized in in FIG. 30. Similarly, commercially available, surface-mounted resistors, when wired together in series on a flexible circuit board serve as thermal actuators on the application of a voltage. The spacing and layout of these components determines localized thermal transport into underlying layers of tissue. Infrared images and optical images shown in FIG. 31 illustrate these concepts. The flexible circuit materials can be constructed of metals (e.g., Copper, Al, Nickel, chromium, or their alloys/combinations) or polymers (e.g. polyimide, polyether ether ketone, polyester, polyethylene terephthalate) with combined thicknesses of <1 mm. Exemplary performance of these devices is shown in FIGS. 35-37.

For both approaches 1) and 2), changes in the piezoresistive or other electronic properties are converted to precise, measurable changes in voltage or current using a customized analog conditioning circuit. This voltage or current is then digitized via an analog to digital converter (ADC), rendering the signal suitable for wired or wireless data transmission. This circuit can consist of Wheatstone bridges, voltage dividers, amplifiers and combinations of these. An example of an analog circuit, along with a circuit simulation, consisting of an NTC temperature sensor, wheatstone bridge and an operational amplifier appears in FIG. 32, and is capable of temperature measurements of <5 mK precision across an ADC range of 2-5V.

Optical Approaches: This encompasses a set of technologies designed to optically measure flow through near-surface conduits such as shunts via thermal transport measurements, either in addition to, or independent of the approaches described above. Broadly, these approaches can be divided into two techniques:

Colorimetric approaches: The arrangement of thermochromic dyes around an actuating element, as described by Gao, et. al [1] allows for the quantitative imaging of heat flow through biological tissue. Images can be recorded via a commercial camera, or through a camera built into a commercial smartphone, and exploit image processing algorithms capable of converting subtle color changes into thermal maps with <100 mK temperature resolution. Examples of such constructions are in FIG. 33.

Infrared/Thermal imaging: The availability of low-cost, commercially available infrared imaging technologies, many of which can seamlessly integrate with a smartphone camera allows for imaging of thermal transport directly through a thermal camera. An example of such a commercially available imager is in FIG. 34, with representative examples of infrared images in the presence (top) and absence (bottom) of flow in a benchtop system.

Both of the above optical approaches require thermal actuation, which can proceed either via the approaches described in points 1-2, or through wireless, inductive power coupling to an on-board receiver coil, as in Gao, et. al[1]

Packaging and Encapsulation

We have developed packaging and encapsulation strategies with the following goals:

Insulation from thermal noise: The introduction of a thermal foam or gel allows for the removal of ambient convective noise. The effects of this foam are shown in FIGS. 35-37, wherein the introduction of a foam increases the signal to noise performance an order of magnitude.

Figure 38:
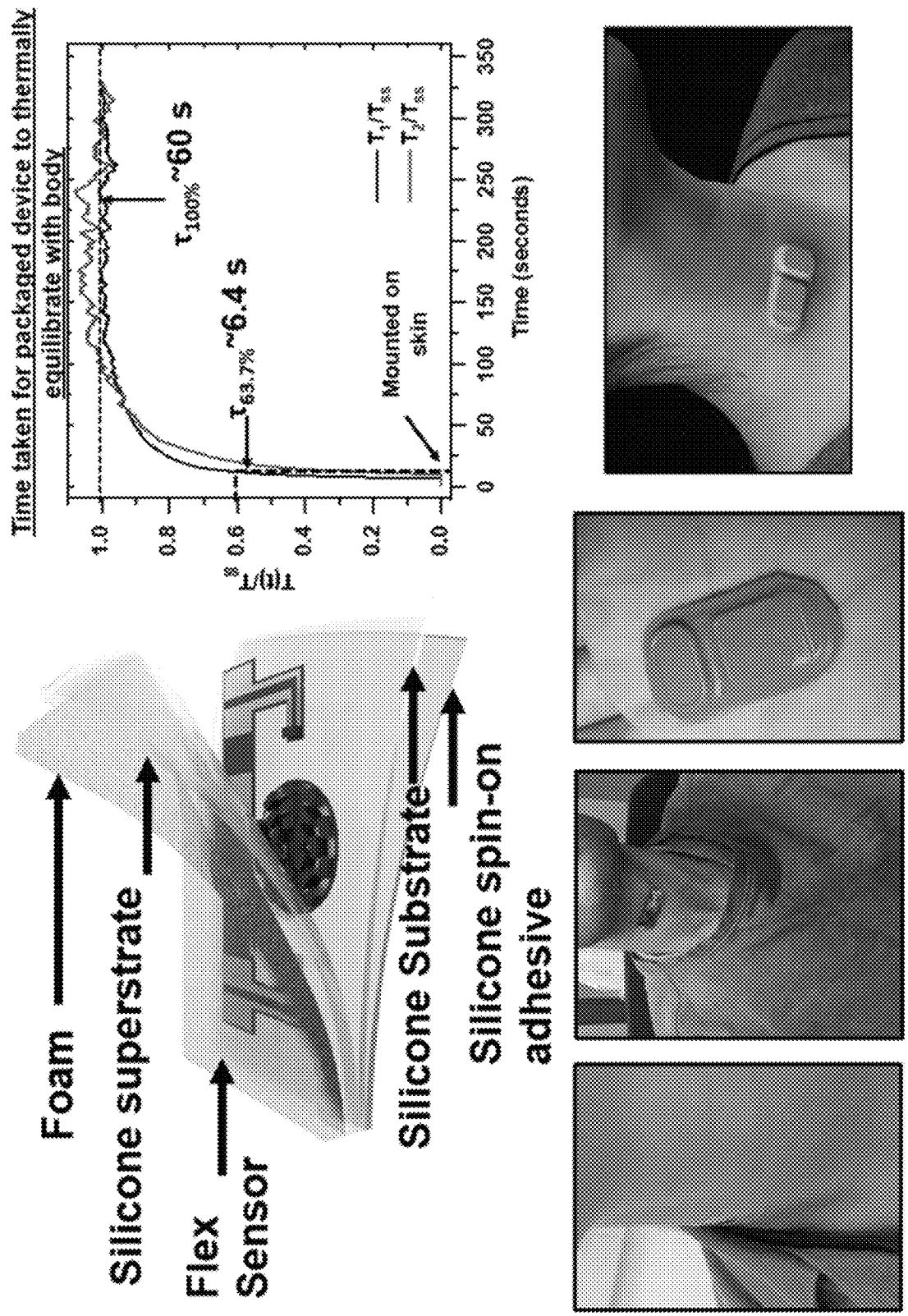
FIG. 38. provides an example sensor integrated with packaging and encapsulation for thermal insulation.

Soft, flexible, user-friendly: The addition of an elastomeric substrate, superstrate and shell allow for easy modulation of external appearance, with a soft finish. These features can be accomplished via casting or molding, as shown in FIG. 38.

Strong, non-irritating adhesion to human skin: The use of customized, silicone or acrylate based adhesive with adhesion energies of <1000 N/m accomplish this.

Easy alignment with shunt, accomplished with alignment markers.

Figure 39:
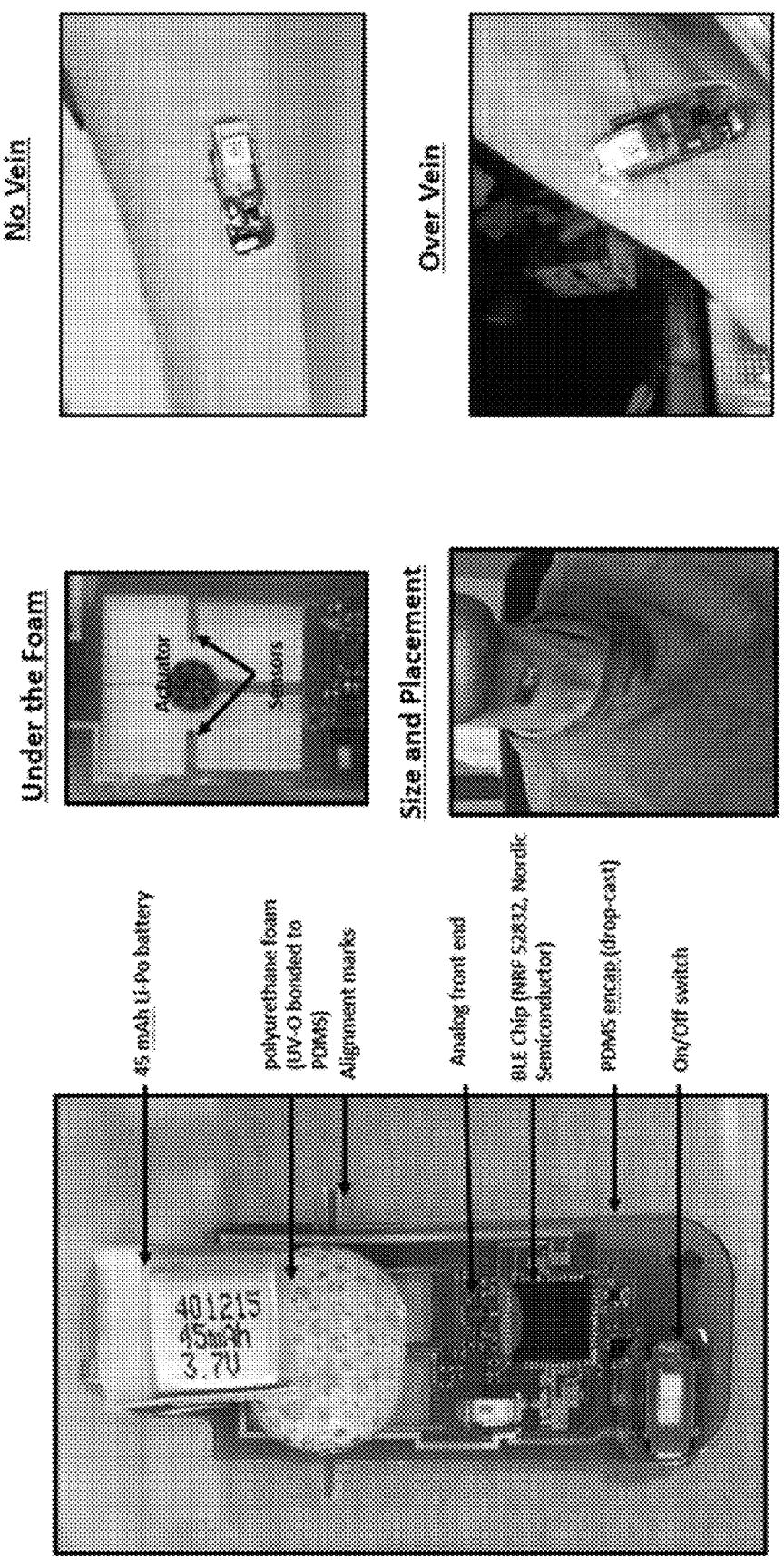
FIG. 39. shows an example device with encapsulation removed to expose and illustrate the various components as described herein.
Figure 40:
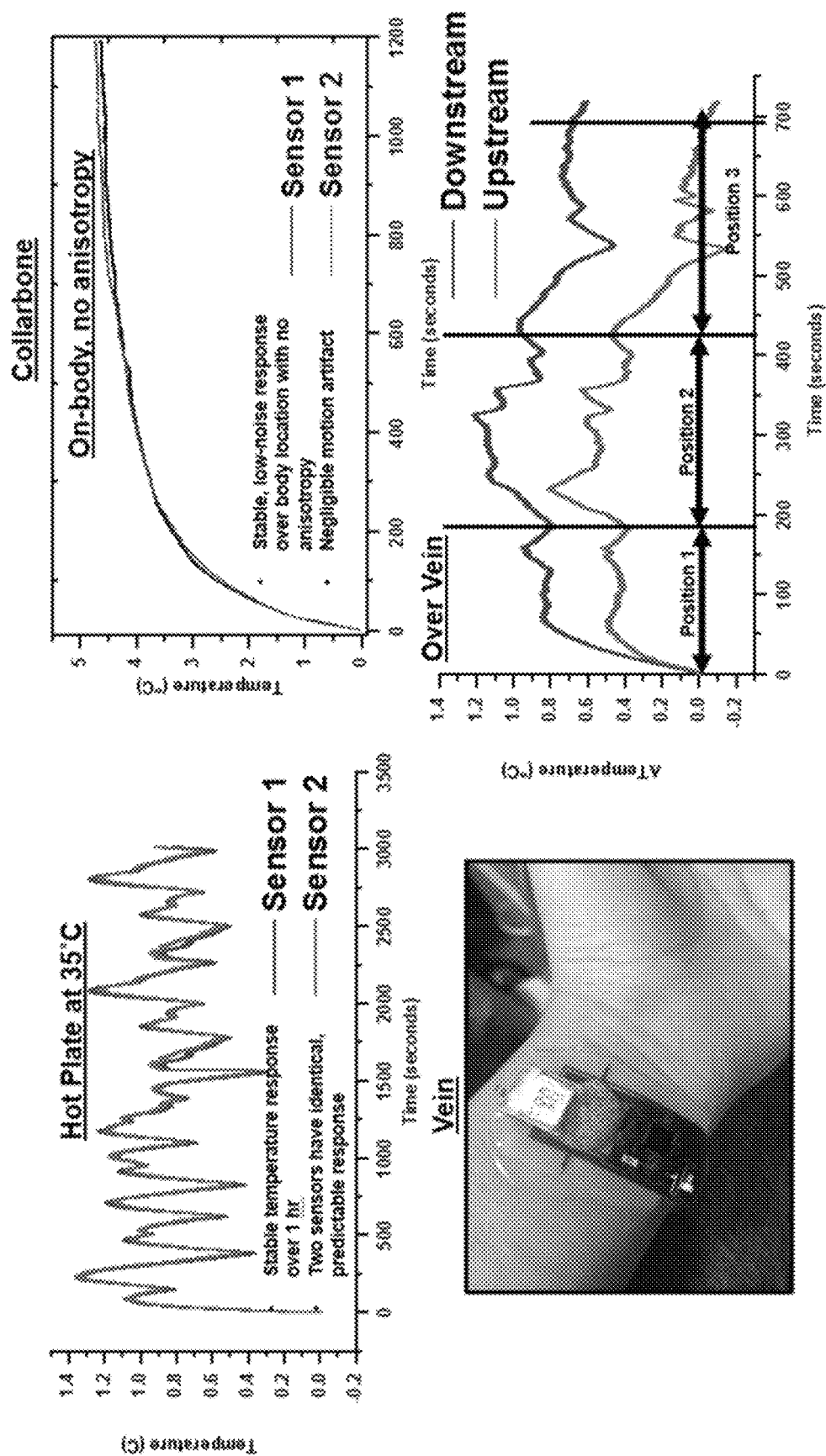
FIG. 40. provides both benchtop and on-body sensing results of an example device.
Figure 41:
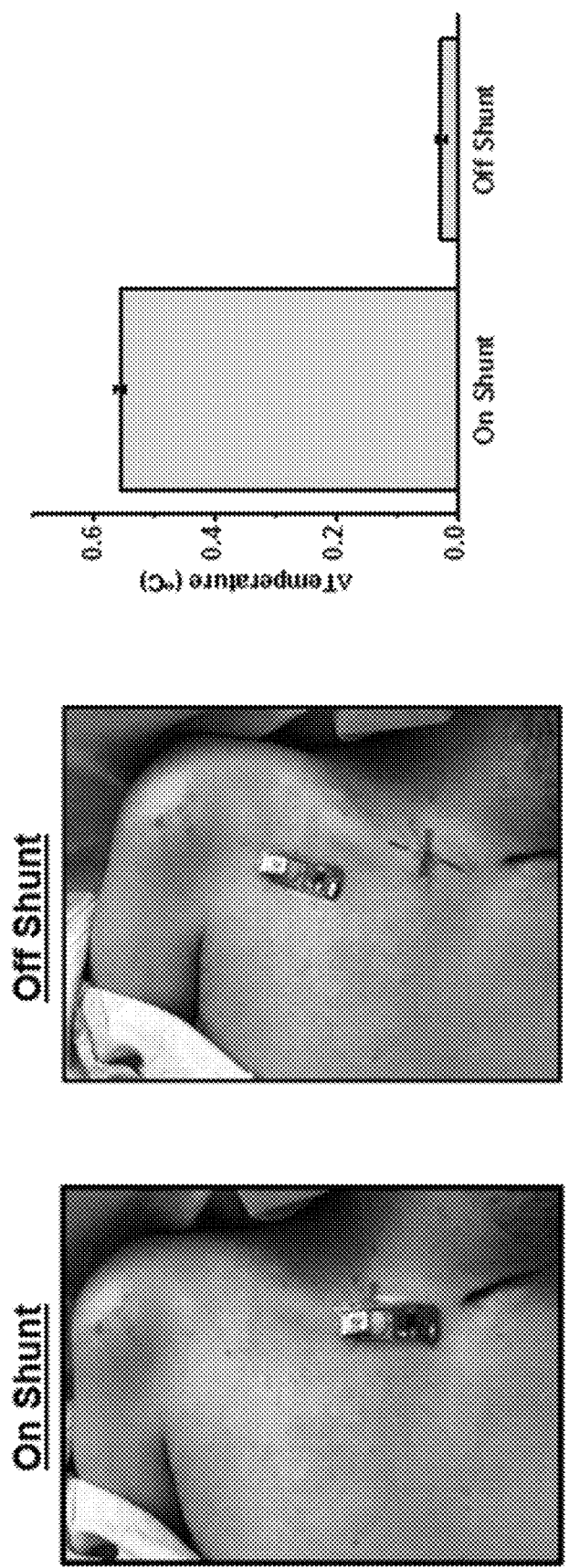
FIG. 41. illustrates the ability of a sensing device to measure change in temperature when positioned over a shunt as an in vivo example.

The miniaturized form factor, alignment markers are visible in FIG. 39, where a measurement made by the platform can clearly distinguish between instances where flow is present and absent, respectively, on a patient with an implanted shunt. Further examples on a patient's volar wrist vein and collar bone, along with in vitro data on a temperature controlled hot-plate are shown in FIG. 40, illustrating the stability of the temperature sensors, and representative data in the presence (vein) and absence (collarbone) of flow induced anisotropies, respectively. FIG. 41 shows the sensor working on a patient with a shunt in an IRB-approved study.

Electronics

Figure 42:
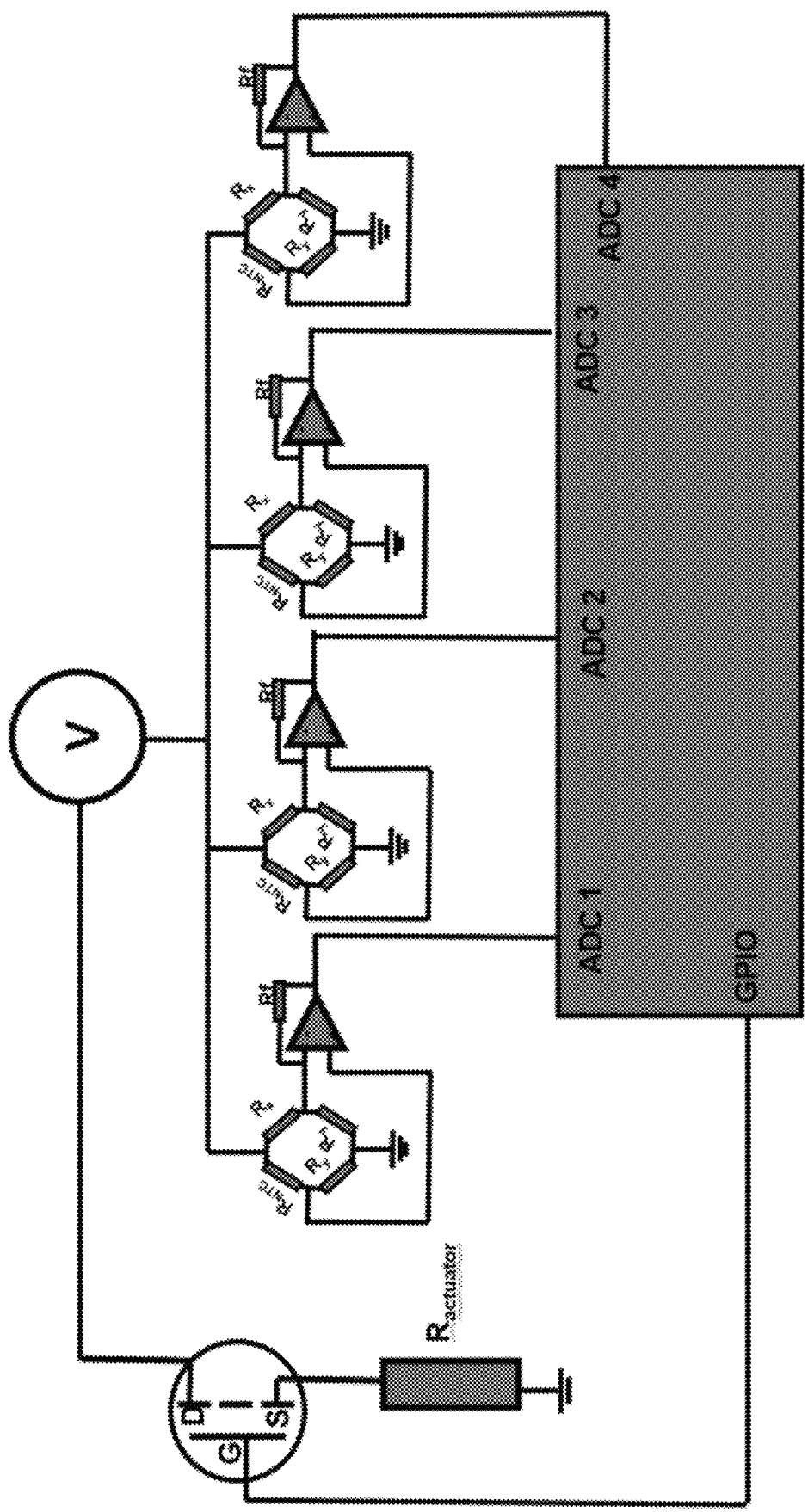
FIG. 42. illustrates the use of a device with multiple sensors and provides an example circuit diagram.
Figure 43:
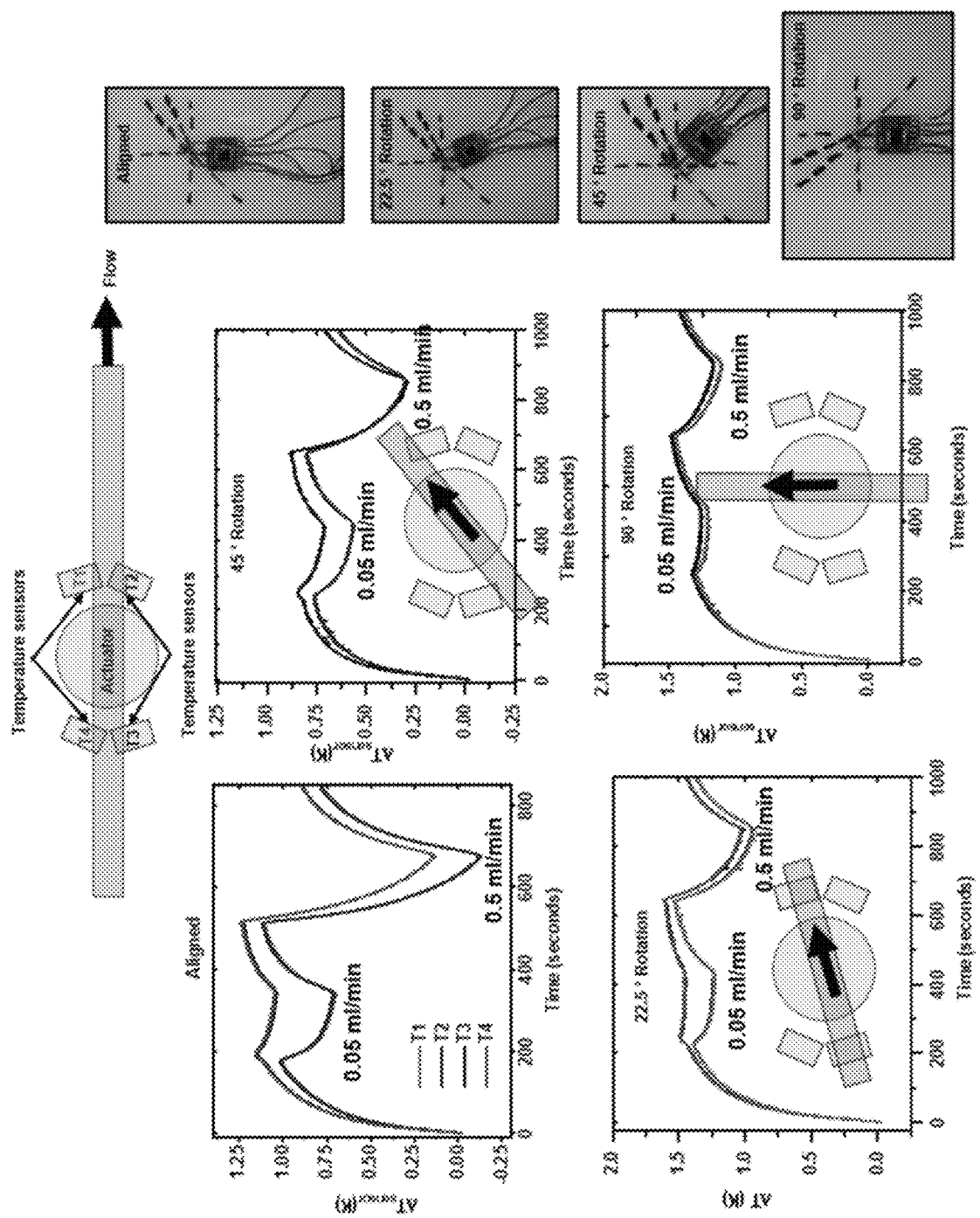
FIG. 43. illustrates the increase in rotational tolerance for 4-sensor device.
Figure 44:
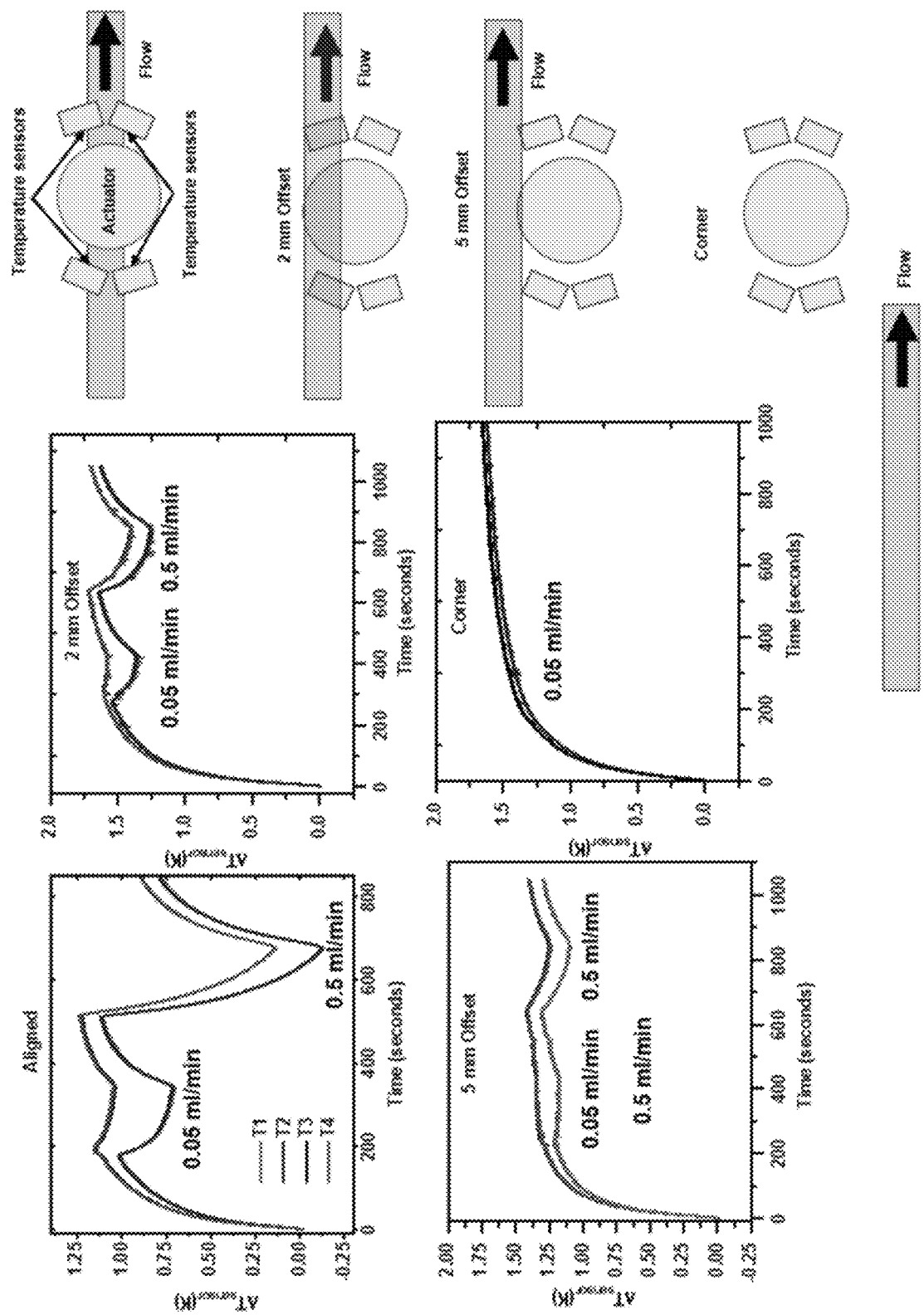
FIG. 44. illustrates the increase in translational tolerance for 4-sensor device.

This disclosure involves the following advanced electronics features, specifically in the context of a wearable, wireless flow sensor, with near-term opportunities in monitoring flow through shunts in patients with hydrocephalus:

Multiple temperature sensors (>2), interfacing and being multiplexed by multiple ADCs on-board the Bluetooth chip. These could be addressed directly to ADC pins, or rapidly addressed via a miniaturized multiplexing unit. The addition of multiple sensors provides redundancy in the measurement, and also ensures larger tolerances to positional uncertainties. Schematics and benchtop data from a 4-sensor embodiment are shown in FIGS. 42-44.

Figure 45:
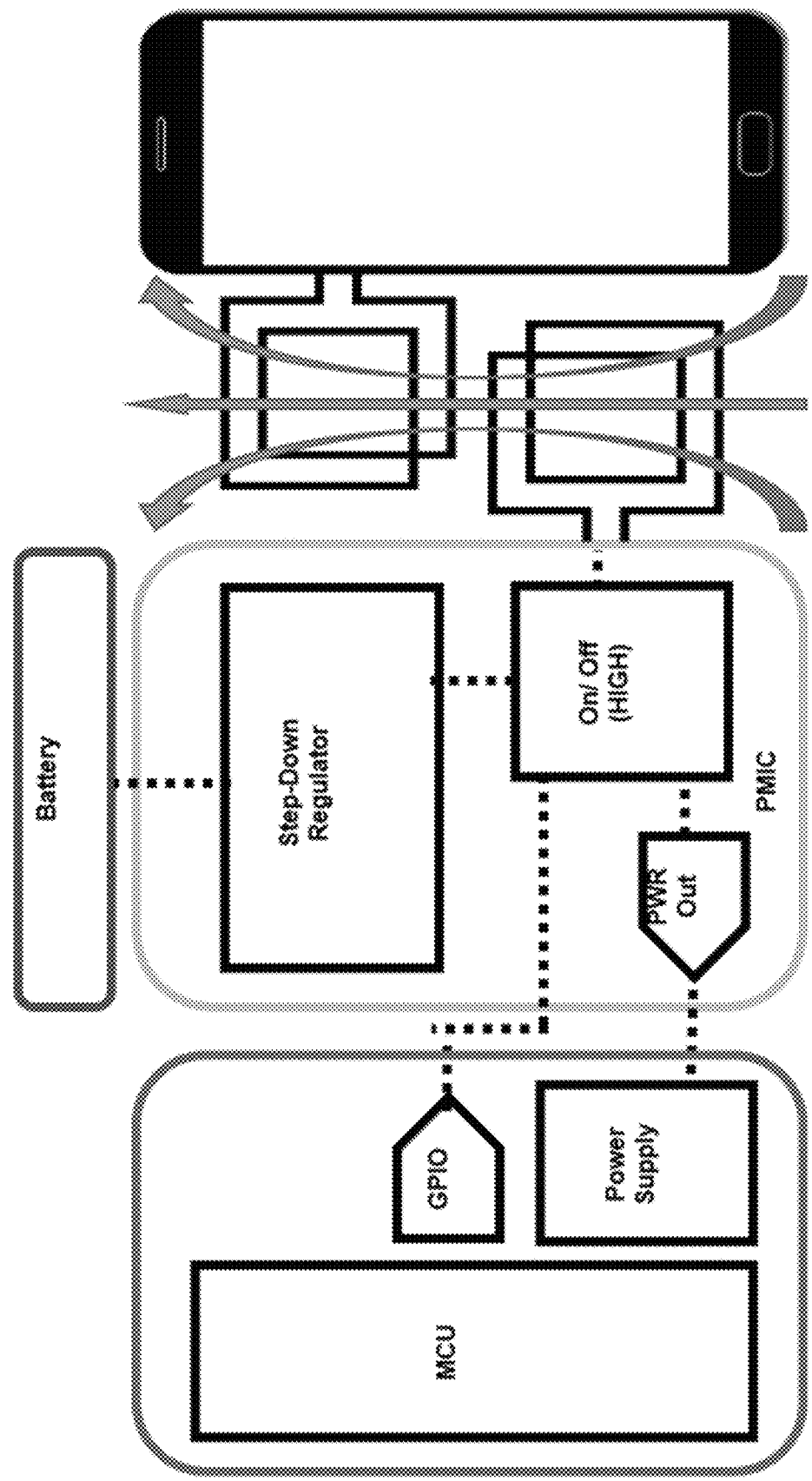
FIG. 45. provides example hardware for wireless, inductive power coupling for recharging and BLE wake-up.

The inclusion of a coiled wire to wirelessly inductively couple power into the circuit for powering, wireless recharging, or for operations on the Bluetooth chip such as waking it up from deep sleep mode. A schematic of such a system is shown in FIG. 45.

The inclusion of relevant power management components, such as regulators, DC-DC converters, and rectifying circuit elements such as diodes and capacitors to form full or half wave rectifiers.

The use of frequencies for power transfer that are compatible with near-field communication protocols (e.g., 13.56 MHz).

The use of gate actuation schemes to switch large loads to the actuator with low current outputs from the Bluetooth chip.

Each of the above features contributes to system level usability, as borne out by multiple patient trials.

Software

1. Creation of a firmware embedded application (henceforth referred to as the "Application") that can operate on a Nordic Semiconductor NRF52 development board or System on Chip (SoC).

2. The Application will be able to read from four temperature sensors attached to the development board at a rate of 3 samples per second or greater.

3. The Application will transmit the temperature readings to a Bluetooth 4.0 stream, where the data can then be received by a paired Bluetooth 4.0 capable device.

4. The Application will have a time indicator for each temperature sample taken. This will also be transferred on the Bluetooth 4.0 data stream.

5. The Application will be able to activate a heating element or collection of heating elements through a button or option on the application screen.

6. Creation of a windows/android/iOS application (henceforth referred to as the "Application") that can operate on the Windows 10 Home Operating System, Android or iPhone environments respectively.

7. The Application will require to operate that the device it is being operated on supports Bluetooth 4.0 through the operating system.

Application.

8. The Application will be able to read the data stream from the Application.

9. The Application will be able to graph the 4 temperature readings on the same plot, or on different plots, along with other relevant quantities 10. The Application will be able to update the graph as new data is sent from the Application.

11. The application will be able to perform mathematical operations relevant to the conversion of thermal signals to quantitative flow rates.

Additional features include, but are not limited to:

Text reminders to the user for periodic checks.

Instructions for use, integrated directly into the app, as a step by step guide with cartoons, etc.

Quick-link interfaces to the hospital and/or attending physician

An example of such an application is provided in FIG. 46.

Figure 47:
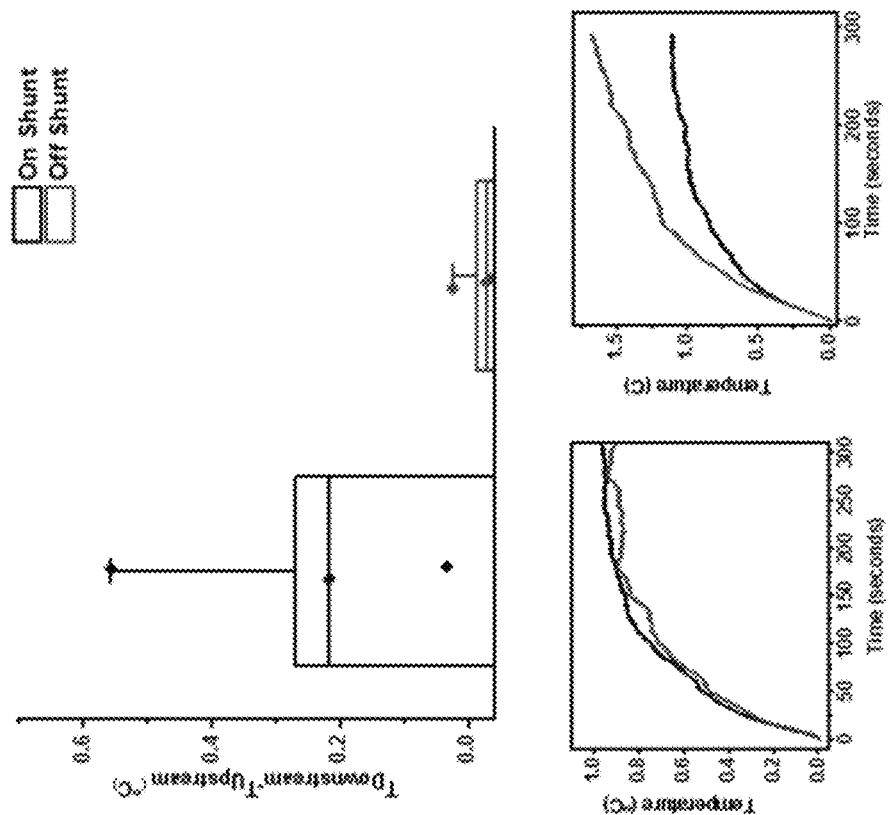
FIG. 47. provides a summary of clinical results.

Clinical Protocols:

We include our clinical protocols and checklists, developed in conjunction with the sensor, to reduce inter-operator variability, and increase patient and physician use. Examples are in FIGS. 47-48, with clinical data validating these protocols in FIG. 47.

While established shunt diagnostics are alternatives to this new technology, there is one competitor that has developed a device based on similar thermal principals. ShuntCheck, developed by the late Dr. Samuel Neff in 2005, utilizes an ice-pack based thermal cooling system connected to a Windows PC DAQ. While it has established itself with 12 years, 11 manuscripts or abstracts, largely positive studies demonstrating its value and over $3 million in NIH funding, the technology is cumbersome and time-consuming. Marketing efforts and publicity have been sparse until this year. Though Phase III trials are underway at NeuroDX and may ultimately demonstrate equivalence to clinical measures, the device's cumbersome, multi-step protocol; equivocal or negative past clinical studies; and need for ice-pack cooling have limited its acceptance. Additionally, patient discomfort due to prolonged skin cooling (detrimental for pediatric diagnostics) and absence of chronic monitoring further limits its diagnostic relevance.

To our knowledge, there is no other comparable wireless noninvasive shunt diagnostic, with or without biometric capabilities or epidermal properties, in the research literature or the commercial domain.

References Related to Example 3

1. Gao, L., et al., *Epidermal photonic devices for quantitative imaging of temperature and thermal transport characteristics of the skin*. Nat Commun, 2014. 5: p. 4938.

Example 4—Exemplary Schematics

Figure 50:
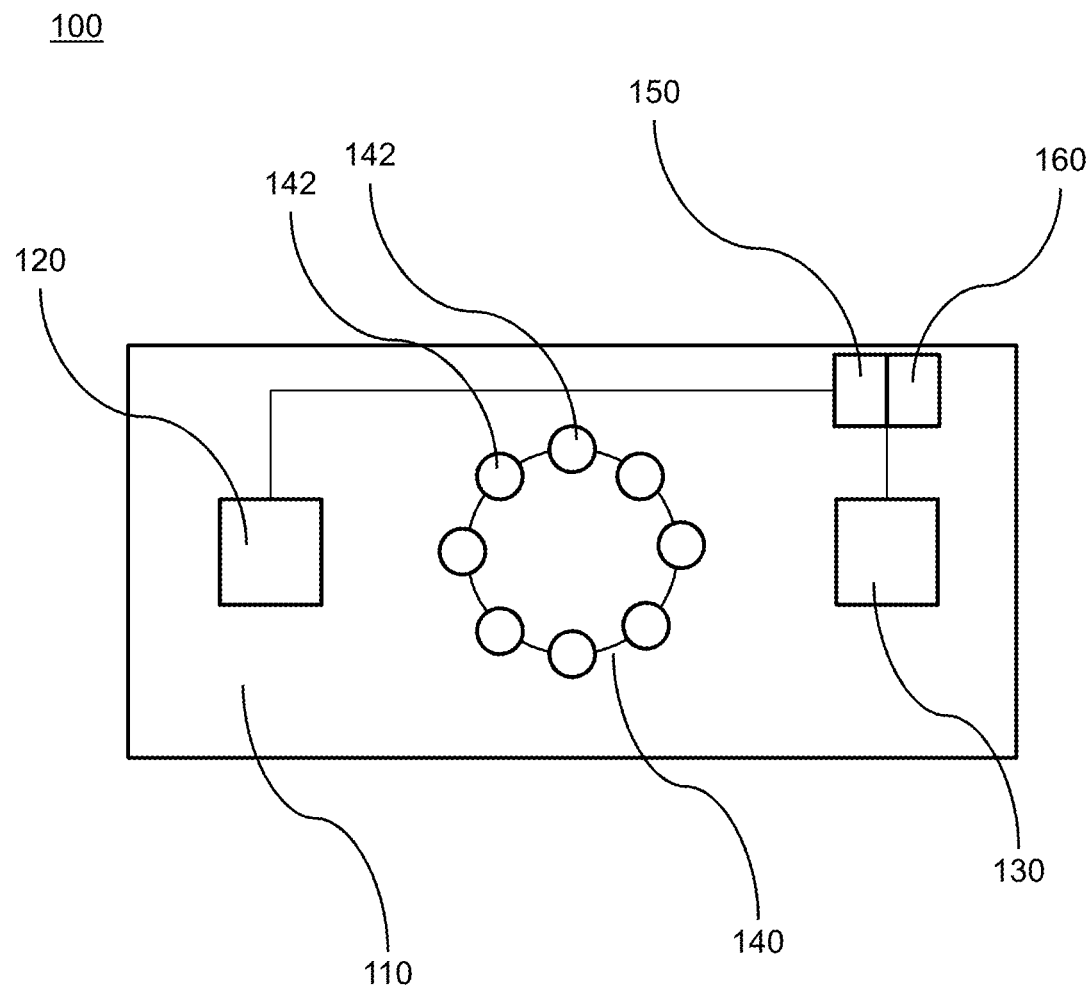
FIG. 50. provides an example schematic of a device as described herein utilizing an array of resistors to provide thermal actuation.

FIG. 50 provides an example of a thermal sensing device 100 that uses an array of resistors 142 as a thermal actuator 140. The thermal actuator 140 is positioned between an upstream temperature sensor 120 and a downstream temperature sensor 130 along a potential fluid flow path, for example, an artery, vein or shunt. Both the temperature sensors 120, 130 and the thermal actuator 140 are supported by a substrate 110. Either the upstream temperature sensor 120, the downstream temperature sensor 130 or both may be an array or plurality of temperature sensors.

In some embodiments, the device 100 may further comprise a power source 150 (e.g. a rechargeable battery) supported by the substrate 110 and operably connected to the temperature sensors 120, 130 and/or the thermal actuator 140. Additionally, a microprocessor 160 may also be provided in operable communication with the temperature sensors 120, 130 and/or the thermal actuator 140.

Figure 51:
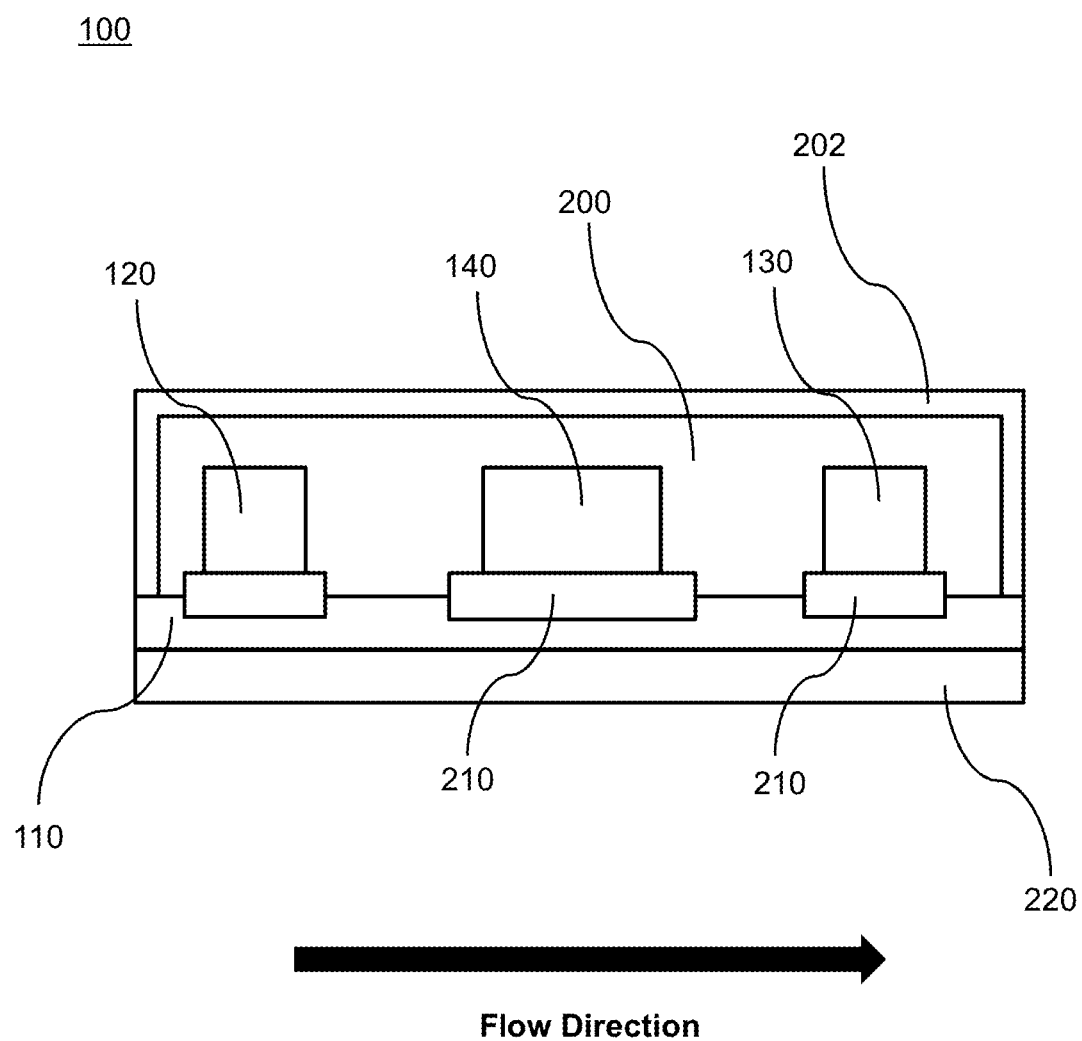
FIG. 51 provides an example cross-sectional schematic of a device incorporating an insulating layer and a discontinuous thermally conductive layer.
Figure 52A:
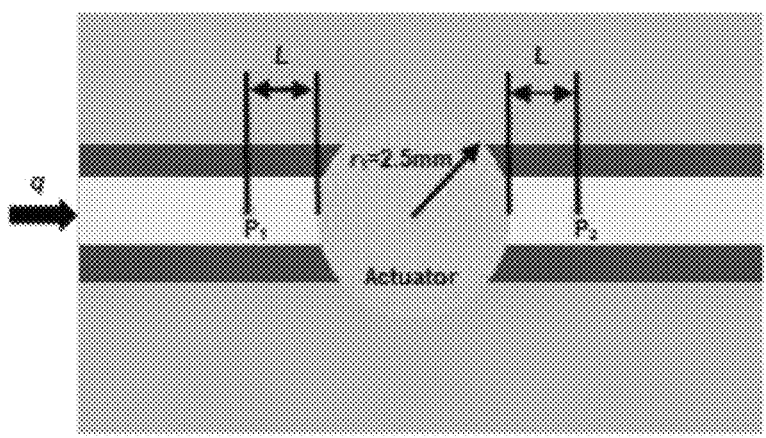
FIGS. 52A-52C illustrate the effect of altered intersensor distances (L).
Figure 52B:
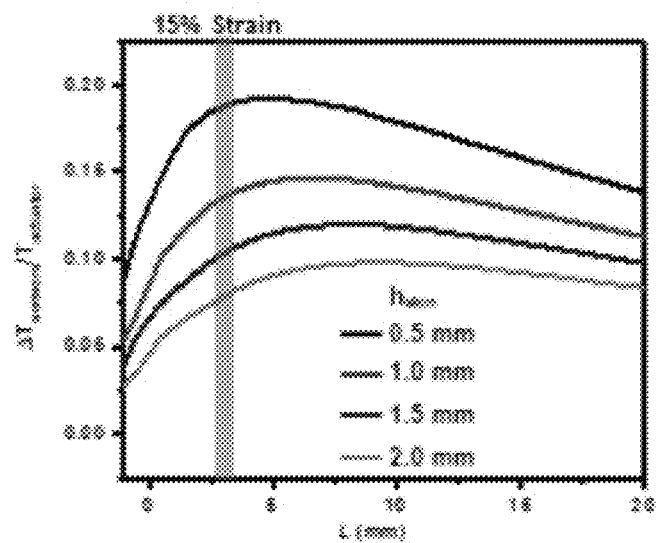
Figure 52C:
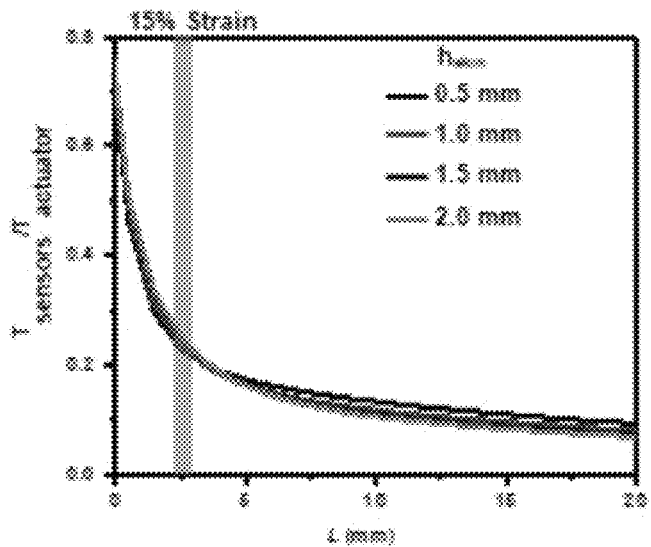

FIG. 51 provides an example cross-sectional schematic of a thermal sensing device 100 that includes an insulating layer 200 and a discontinuous thermally conductive layer 210. Again, the thermal actuator 140 is positioned between an upstream temperature sensor 120 and a downstream temperature sensor 130 along a potential fluid flow path, for example, an artery, vein or shunt. Both the temperature sensors 120, 130 and the thermal actuator 140 are supported by a substrate 110.

The temperature sensors 120, 130 and the thermal actuator 140 are encapsulated by an insulating layer 200, for example, a foam which reduces outside temperature interference and increases the thermal signal to noise ratio captured by the temperature sensors 120, 130. In some embodiments, the insulating layer 200 is further encapsulated by a superstrate 202. A discontinuous thermally conductive layer 210 may be included proximate to the temperature sensors 120, 130, the thermal actuator 140 or both. Additionally, an adhesive layer 220 may be included for establishing and maintain contact with a tissue of a subject or patient.

Example 5: Long-Term, Continuous Measurements of CSF Hydrodynamics in Vivo

Hydrocephalus is a common and debilitating condition resulting in the buildup of cerebrospinal fluid in the ventricles of the brain. It affects >1,000,000 people in the United States, including >350,000 children. The current standard of care for hydrocephalus is the surgical implantation of a ventricular shunt assembly to drain the excess fluid away from the brain and into a distal absorptive site such as the peritoneal cavity. Unfortunately, shunts have an extremely high failure rate (50% over the first two years and about 10% for every year thereafter), and diagnosing shunt malfunction accurately presents a significant clinical challenge due to ambiguous symptoms such as headaches and nausea. Additionally, real-time in vivo CSF hydrodynamic remain poorly understood, frustrating the development of advanced shunt technology. As an example, shunt intermittency is a well-known phenomenon but varies in frequency and magnitude in each patient. As a result, a working but intermittent shunt can be mistaken for shunt failure when tested with a shunt tap or other well-known diagnostic techniques, such as ice-pack mediated cooling. We introduce a wearable, thermal-transport based sensor that relies on anisotropic thermal transport to make precise measurements of shunt flow rate. In this example, we build on those platforms to provide a clinically focused device constructed entirely from commercially available components and using techniques that are aligned with scalable manufacture. The resulting fully wireless, miniaturized embodiment possesses a set of properties in accuracy, precision, size, weight and cost that represent a significant improvement. Importantly, the size and construction of the platform allow it to be worn continuously over extended periods, enabling, for the first time, long-term, continuous measurements of CSF hydrodynamics in vivo.

Fully integrated flow sensing using commercially-available components:

Fabrication An exploded view illustration of the sensor is in FIG. 53A. The platform utilizes commercially mature flexible circuit board (flex-PCB) structuring technology and relies entirely on commercial off the shelf (COTS) components for operation. A commercial UV laser structures conducting traces and bond pads on a dense, trilayer laminate material of copper-polyimide-copper (18 μm-75 μm-18 μm). Reflow soldering using low temperature solder paste allows for the precise, rapid placement of miniaturized surface mounted device (SMD) elements onto the board. Separately, a thin silicone sheet (Silbione, Bluestar Silicones 100 µm) is spin-cast onto a smooth glass slide, surface treated to be hydrophobic. Importantly, it is semi-cured in order to enhance its adhesion. Flash curing the entire assembly at 100° C. for 120 s ensures robust adhesion between the silicone and the device. A top silicone layer is then drop cast and cured at 70° C. for 60 minutes to form a 300 µm superstrate. A UV-Ozone treatment of the top surface renders it hydrophilic, and in-situ curing of a soft, flat (3 mm) poly-urethane foam layer (FlexFoam, Smooth On Inc.) over the sensing and actuating components ensures robust insulation from ambient thermal noise. Separately, a thin (<2 mm) silicone (Silbione) shell (FIG. 61) is formed by casting a liquid precursor into a pair of customized male and female fittings, milled from commercially available Aluminum in a 3-axis CNC milling machine, and curing at 100° C. for 15 minutes. A UV-Ozone treatment of the superstrate layer on the device and the shell creates a hydrophilic interface, and the two surfaces are bonded by curing at 70° C. for 6 hours. Laser cutting the outline of the sensor and mounting a commercially available, skin-safe, laser-cut adhesive completes the fabrication.

Figure 54D:
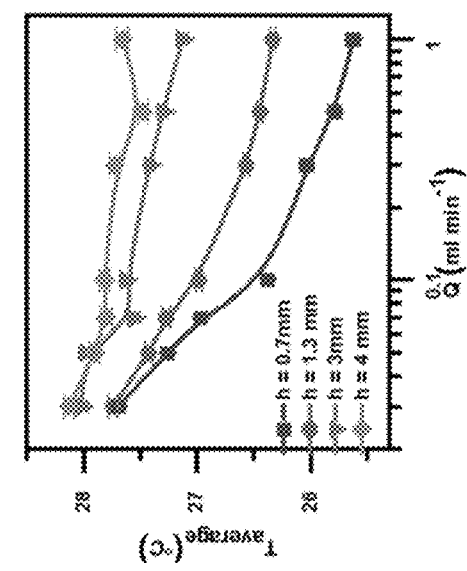
FIGS. 54A-54F. Benchtop flow characterization using platform.
Figure 54C:
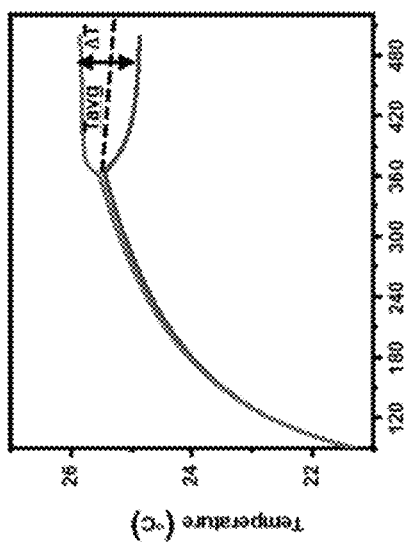
Figure 54A:
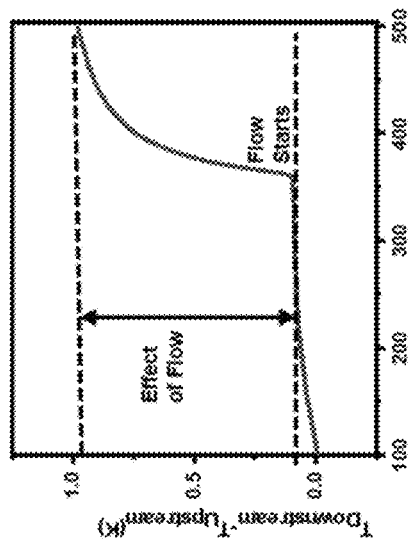
Figure 54F:
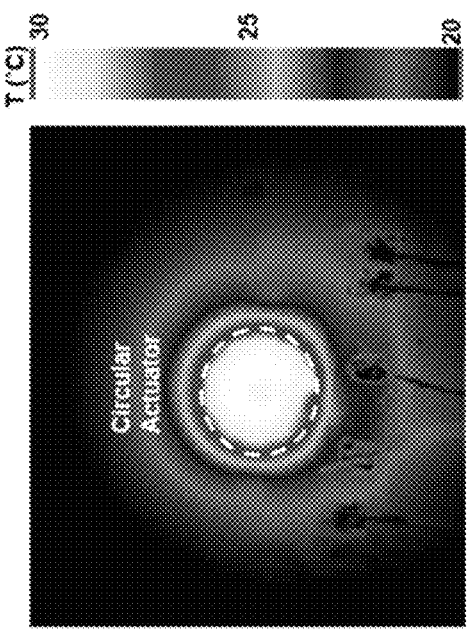
Figure 54E:
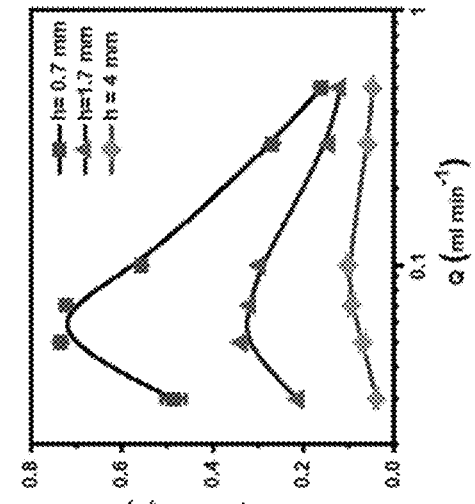
Figure 54B:
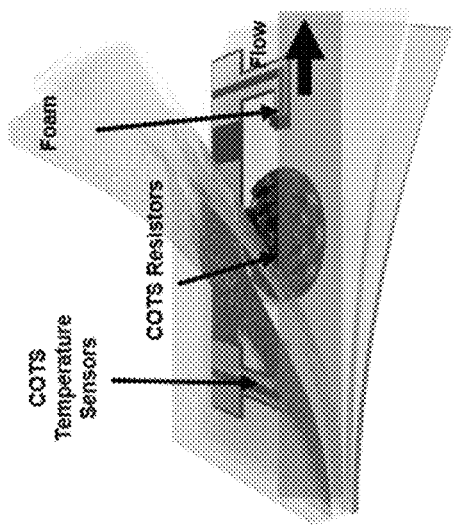
Figure 55A:
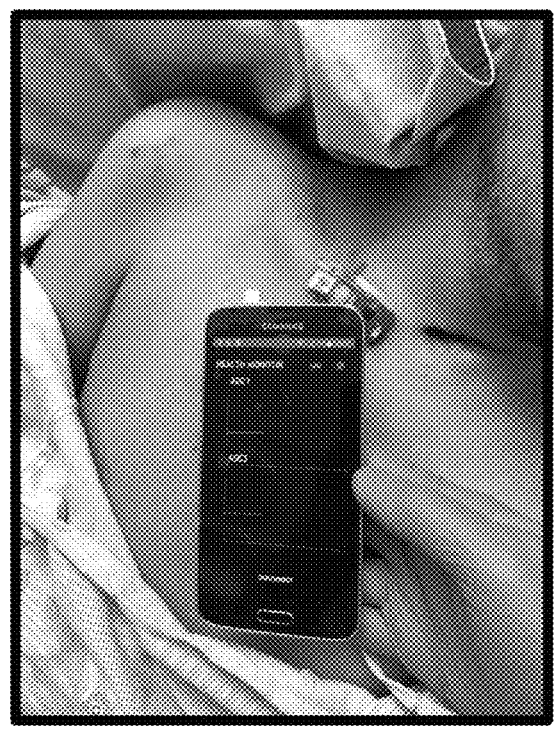
FIGS. 55A-55B. Patient studies on adults.
Figure 55B:
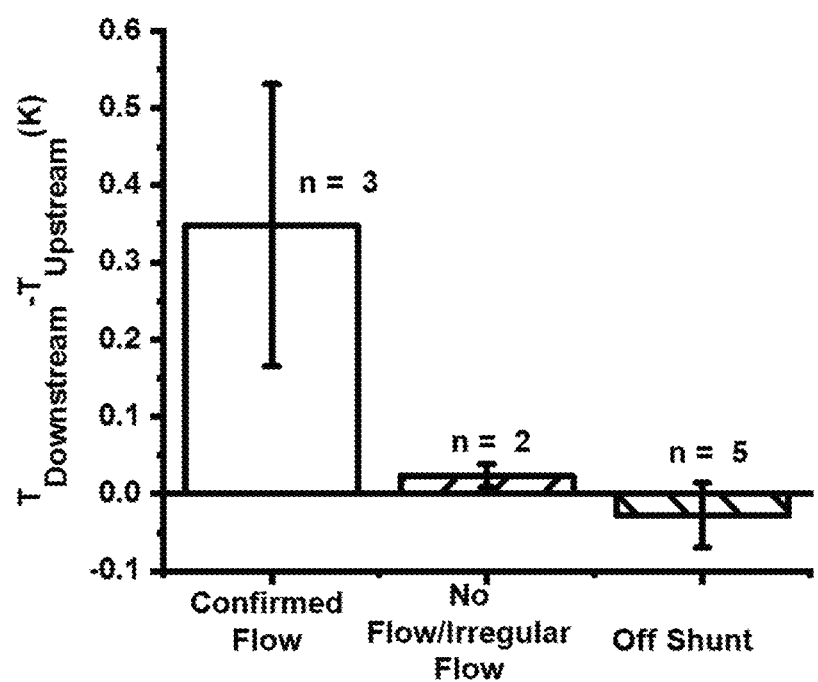
Figure 56:
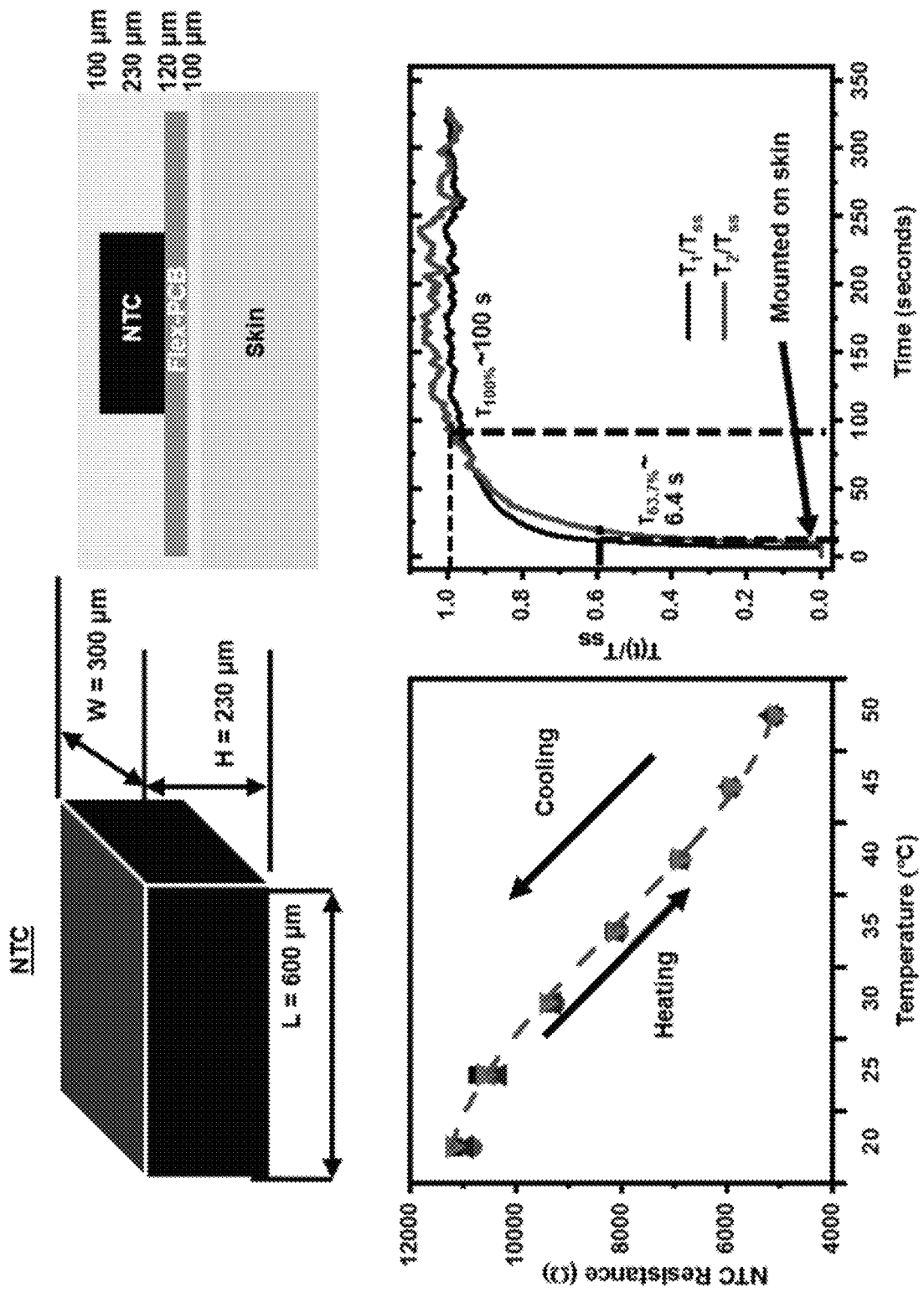
FIG. 56. Spatial and Temporal Precision of negative temperature coefficient temperature sensors (NTCs).
Figure 57:
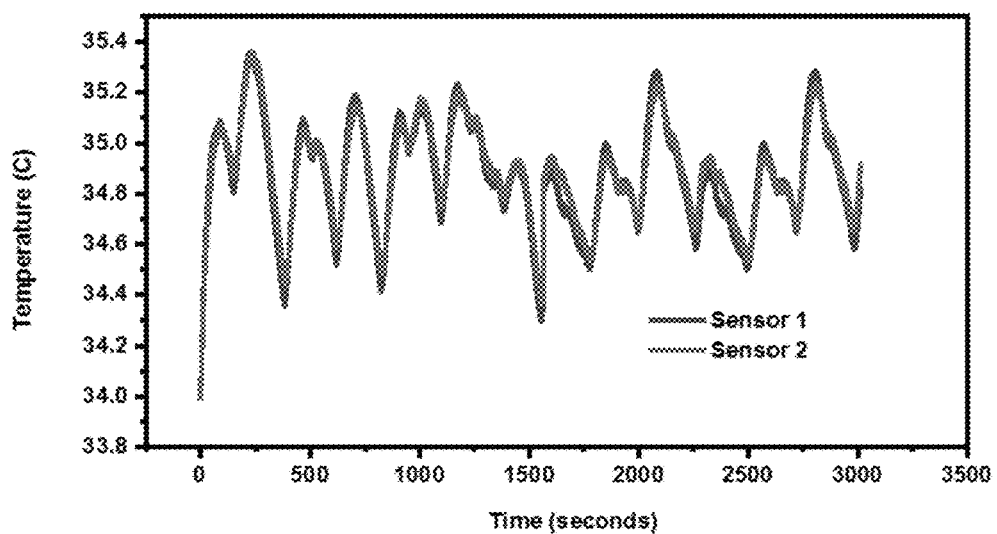
FIG. 57. Stability of temperature sensors, with measured temperature from two temperature sensors as a function of time.

Working Principles: The sensing platform relies on measurements of thermal transport yielded by combinations of thermal sensors and actuators, closely thermo-mechanically coupled to the underlying skin, with the soft, flexible construction of the device ensuring a tight thermo-mechanical coupling to the underlying skin. The sensing platform comprises a thermal actuator and a set of coplanar temperature sensors located upstream and downstream of the underlying shunt catheter (FIG. 54A). The actuator is constructed from a series of fixed, surface mounted resistors (230 um×300 um×600 um) electrically connected in series and laid out in a circular, densely packed array. The packing density of the resistors represents a tradeoff between yield, with high densities exceeding the capabilities of commercial and place technologies, and thermal transport considerations. Packing densities of <40 $\Omega/mm^2$ result in uneven thermal transport and significant in-plane thermal dissipation. The application of a fixed, controlled voltage results in localized thermal actuation of 1.7 $mW/mm^2$, causing a local temperature increase of ~5K (FIG. 54B). As described in previous reports, the presence of flow underlying the actuator results in anisotropic thermal transport (FIG. 54C). Commercially available negative temperature coefficient (NTC) temperature sensors constructed from metallic oxides form high-precision (2 mK), low-hysteresis temperature sensors whose resistance varies approximately linearly in a biological relevant regime (FIG. 56). The low thermal masses of these elements result in equilibration times of ~60 s with underlying tissue. Locating these elements upstream and downstream of the actuator along the direction of the shunt captures the effects of flow, with the downstream and upstream temperature measurements ($T_{Downstream}, T_{upstream}$) bifurcating (FIGS. 54D-54C). The resulting temperature differential, $T=(T_{Downstream}-T_{upstream})$ obeys a non-monotonic but well-understood relationship with flow rate across a range relevant to CSF flow through shunts (FIG. 54E), extensively described in a previous report. The average temperature of the two sensors, $T_{average}=(T_{Downstream}+T_{upstream})/2$ can be used to differentiate between high flow and low flow values with the same levels of thermal anisotopy, by capturing the net temperature decrease brought about by the convective effects of flow at high rates (FIG. 54E). Skin thickness plays a key role in regulating thermal transport to the underlying shunt, and an increased skin thickness will result in diminished signal to noise, with 6 mm representing an outer limit for reliable measurements.

Figure 61:
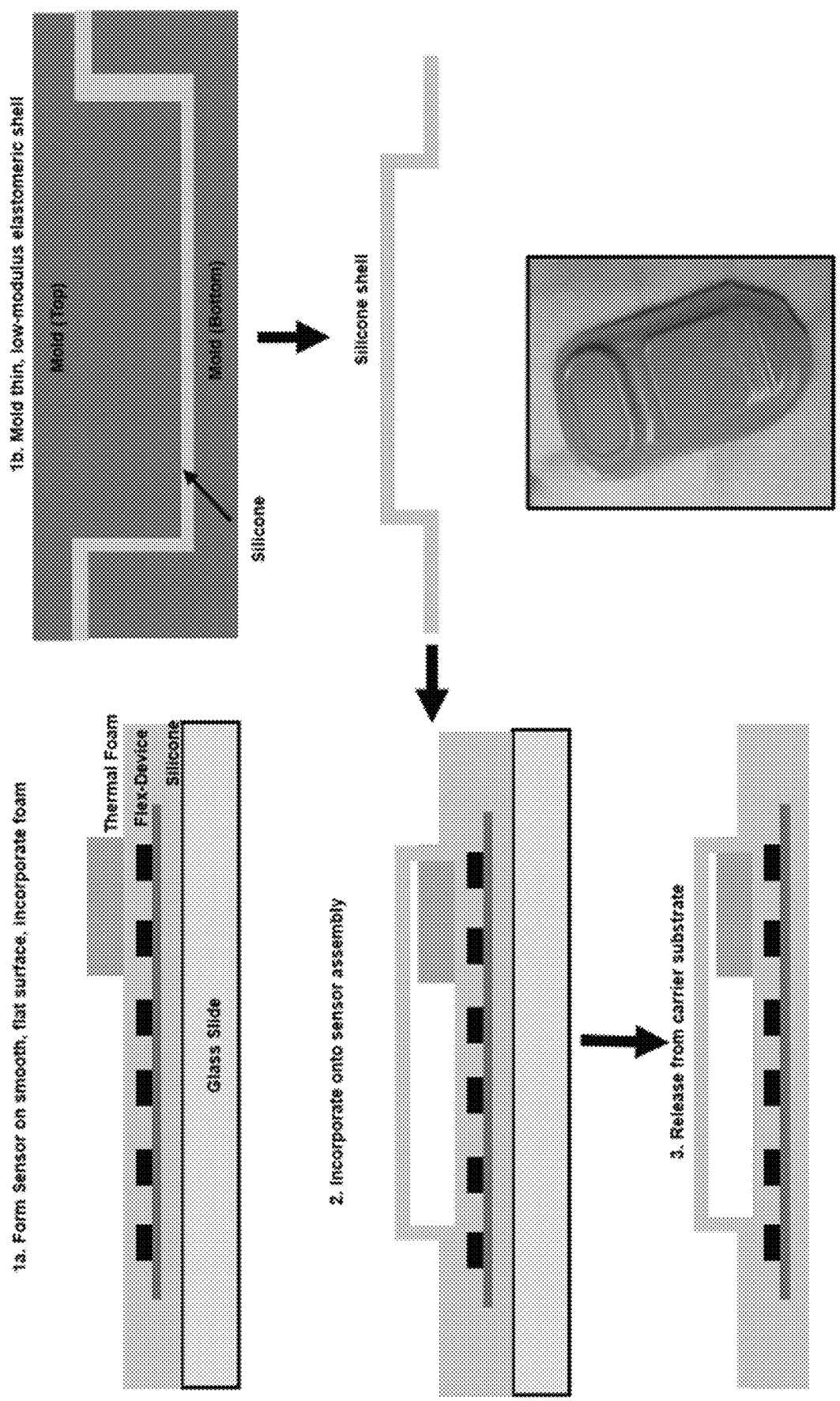
FIG. 61. Molding and packaging process that can be used to make any of the devices of the instant invention.
Figure 62:
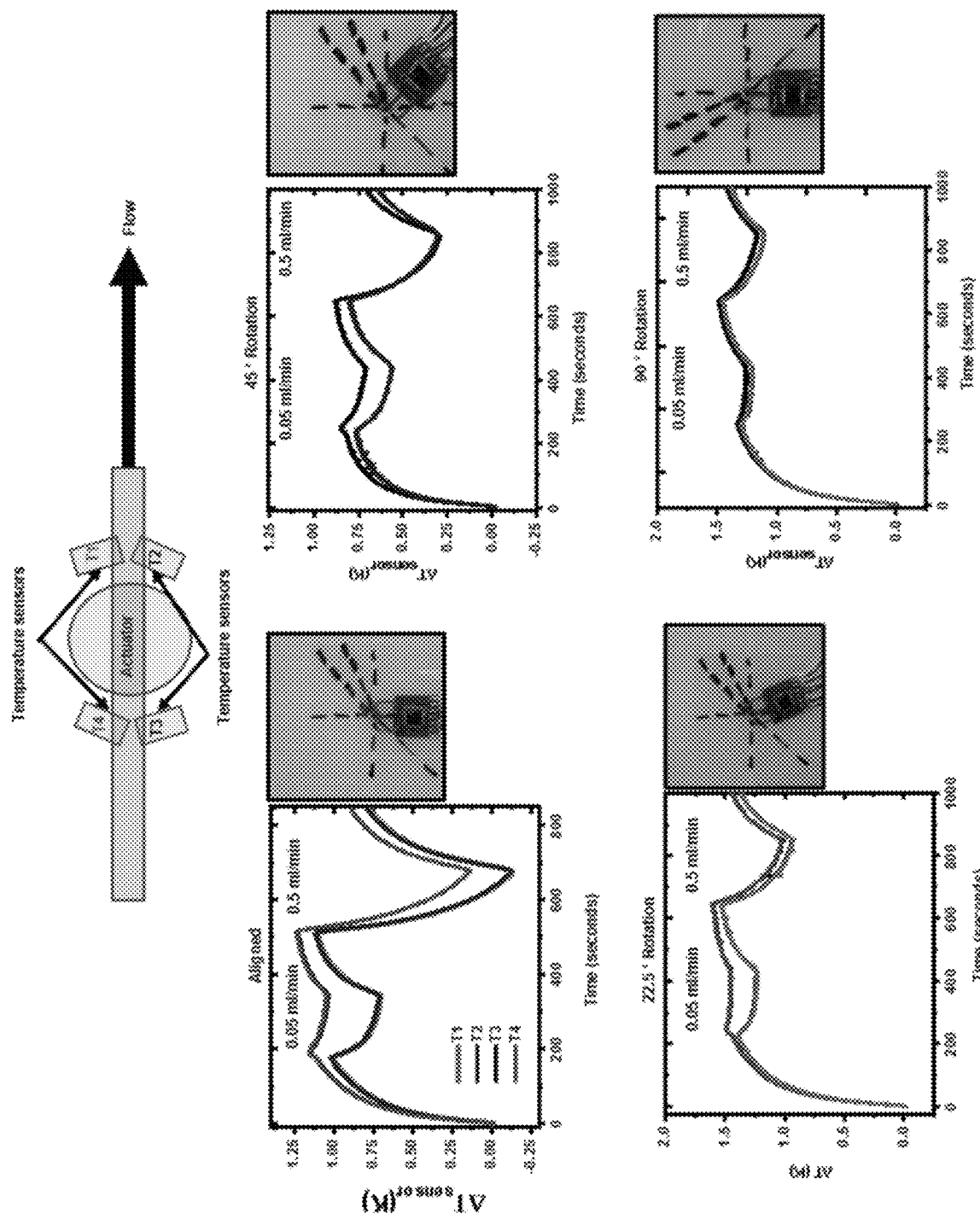
FIG. 62. Device configured to have rotational tolerance by a 4-sensor device. The plots are for a device aligned and for various rotations of 22.5, 45 and 90 degree rotation.
Figure 63:
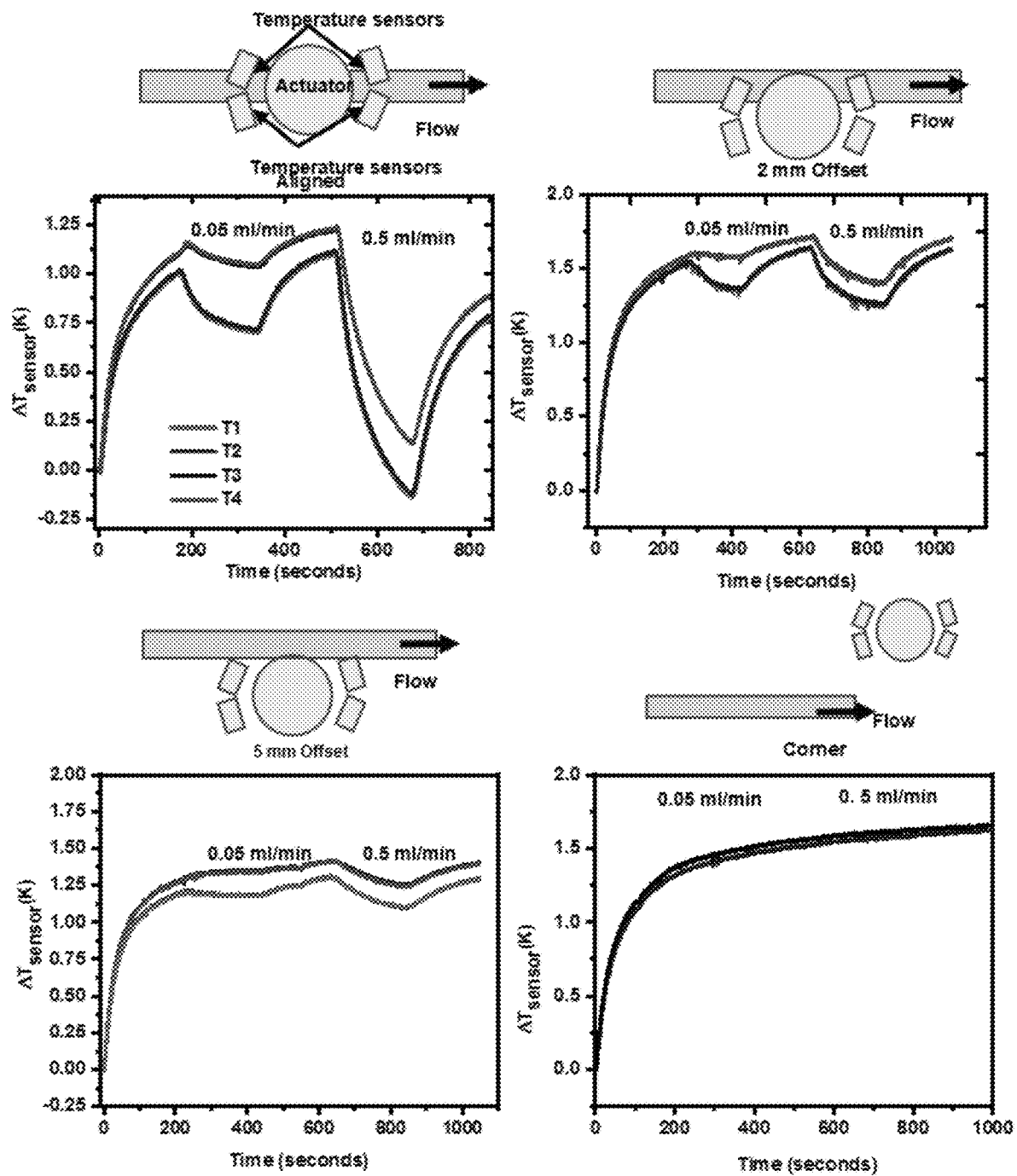
FIG. 63. Device configured to have translational tolerance by a 4-sensor device. The plots are for a device aligned and for various translational offsets of 2 mm, 5 mm and complete misalignment.
Figure 64:
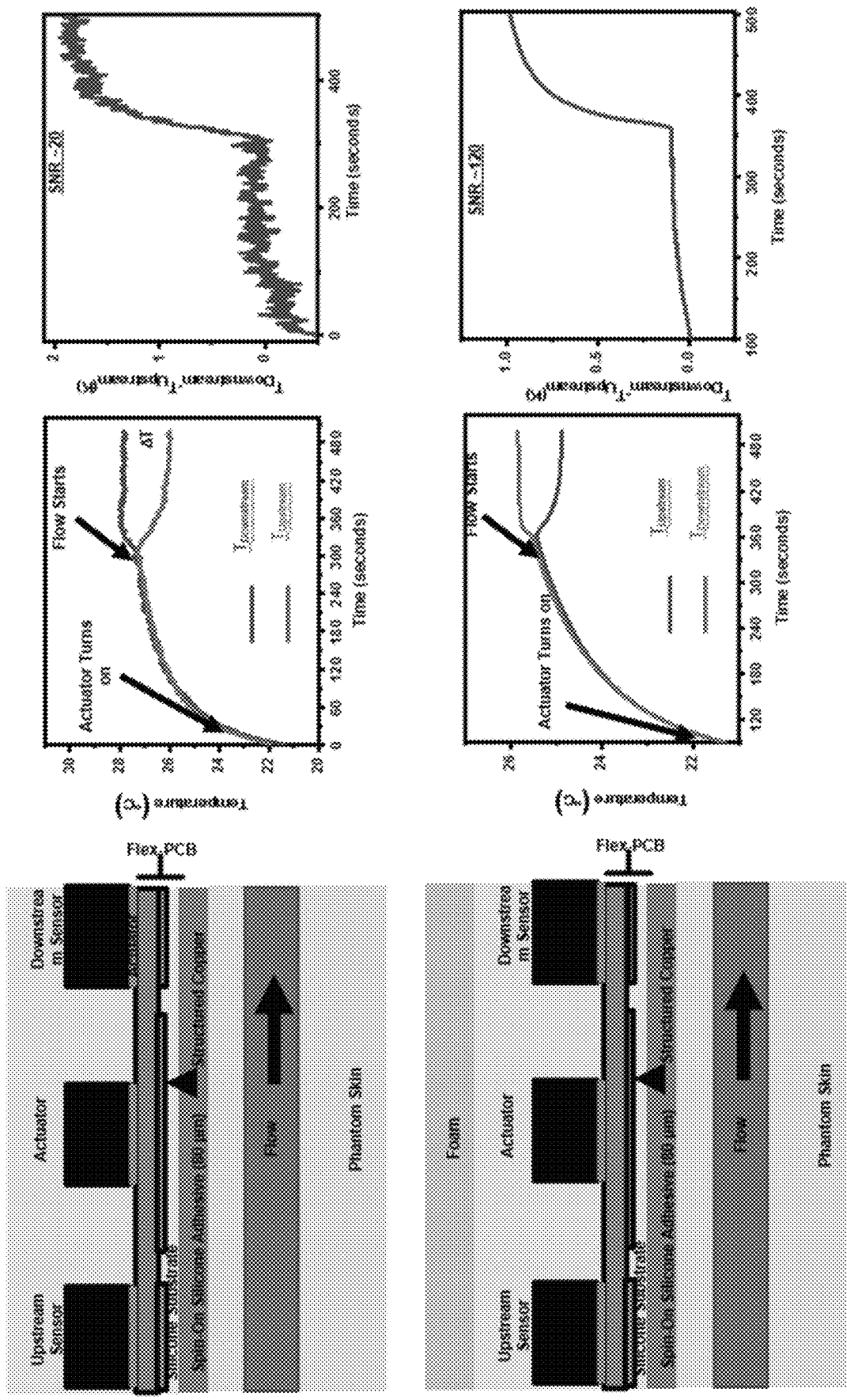
FIG. 64. Effect of foam insulation on temperature sensors.
Figure 65:
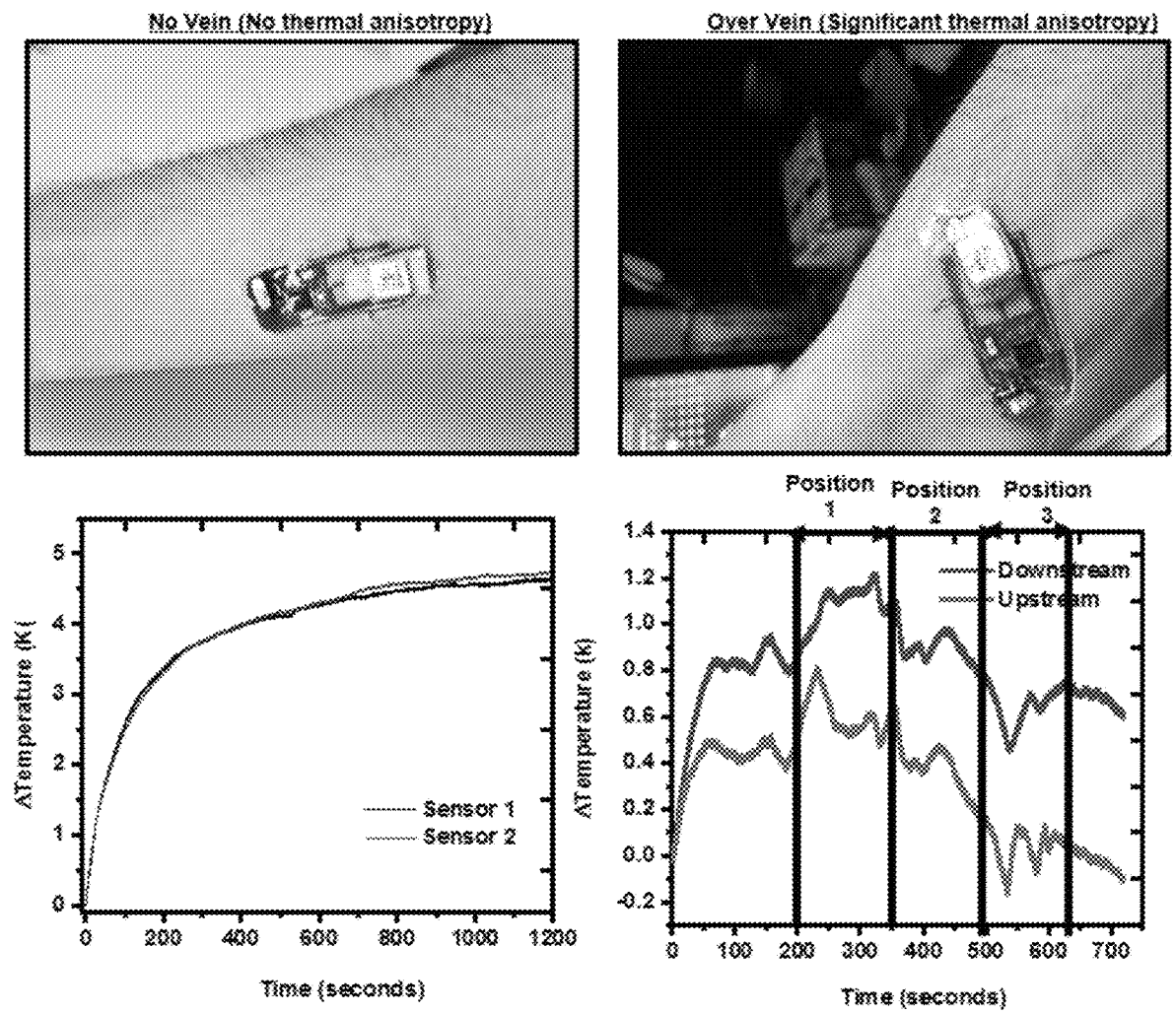
FIG. 65. Applicability to blood vessels, with the left panels for a device that is not over a blood vessel and the right panels for a device over a vein.

Positional uncertainties and ambient thermal noise represent two key potential sources of error. Positional uncertainties are mitigated by the following steps: 1) the addition of two additional temperature sensors, one each upstream and downstream affords an increased positional and rotational tolerance. These effects are shown in FIGS. 61-62, where the sensor can accommodate positional uncertainties of up to 5 mm and rotational uncertainties of ~23°. 2) The addition of alignment markers along the center-line of the sensor/actuator axis (seen in FIG. 53B) allows for physicians/practitioners to align the device immediately after palpating the shunt. 3) The addition of an insulating layer, such as a foam layer, above the sensing/actuating elements significantly alleviates ambient thermal noise, as seen in FIG. 64. The devices and methods provided herein, therefore, may be described as having a rotational and/or translational positional tolerance, including accommodation of a rotational misalignment of up to 23 degrees and/or translational misalignment of up to 5 mm, without significantly impacting performance. This is a significant improvement, as in use a practical challenge is achieving precise alignment with the underlying flow conduit.

Figure 59:
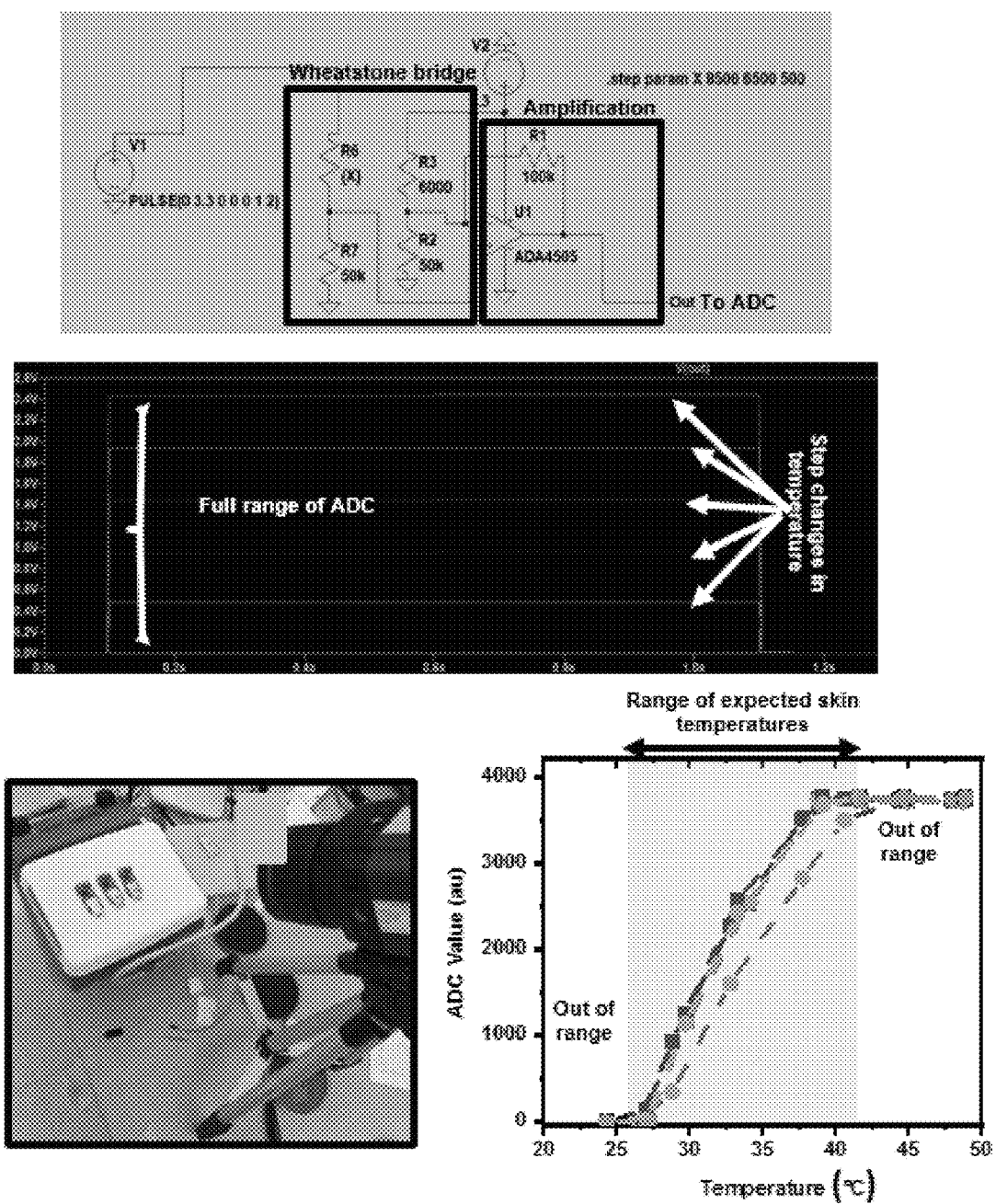
FIG. 59. Analog front end and wireless temperature sensing precision. The temperature sensors show high linearity over a range of biologically-relevant skin temperatures.
Figure 60B:
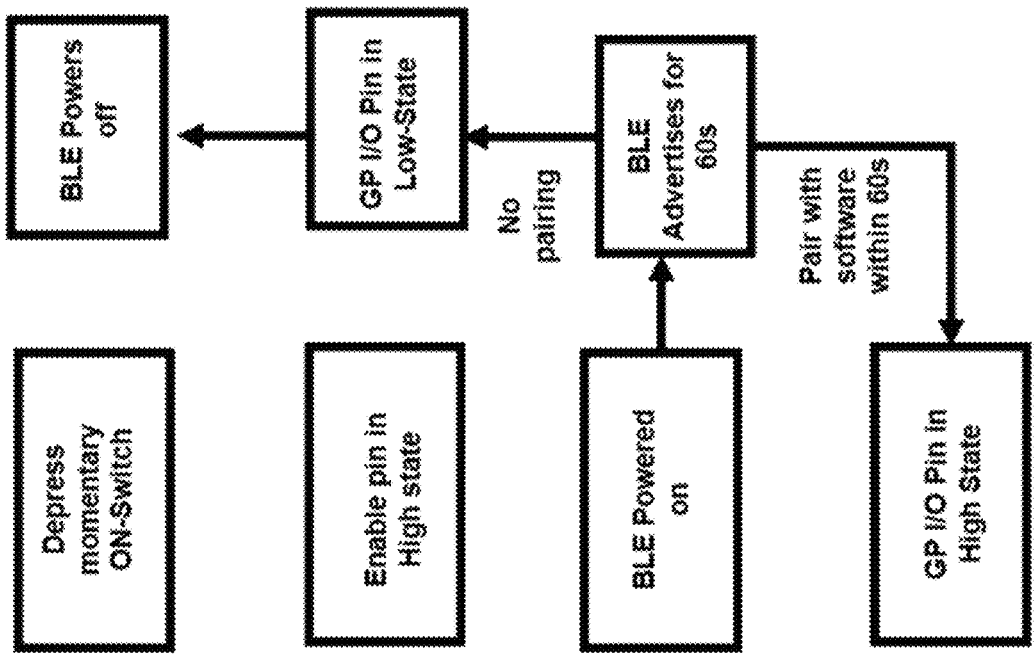
FIGS. 60A-60D. Power-saving switch feature.
Figure 60A:
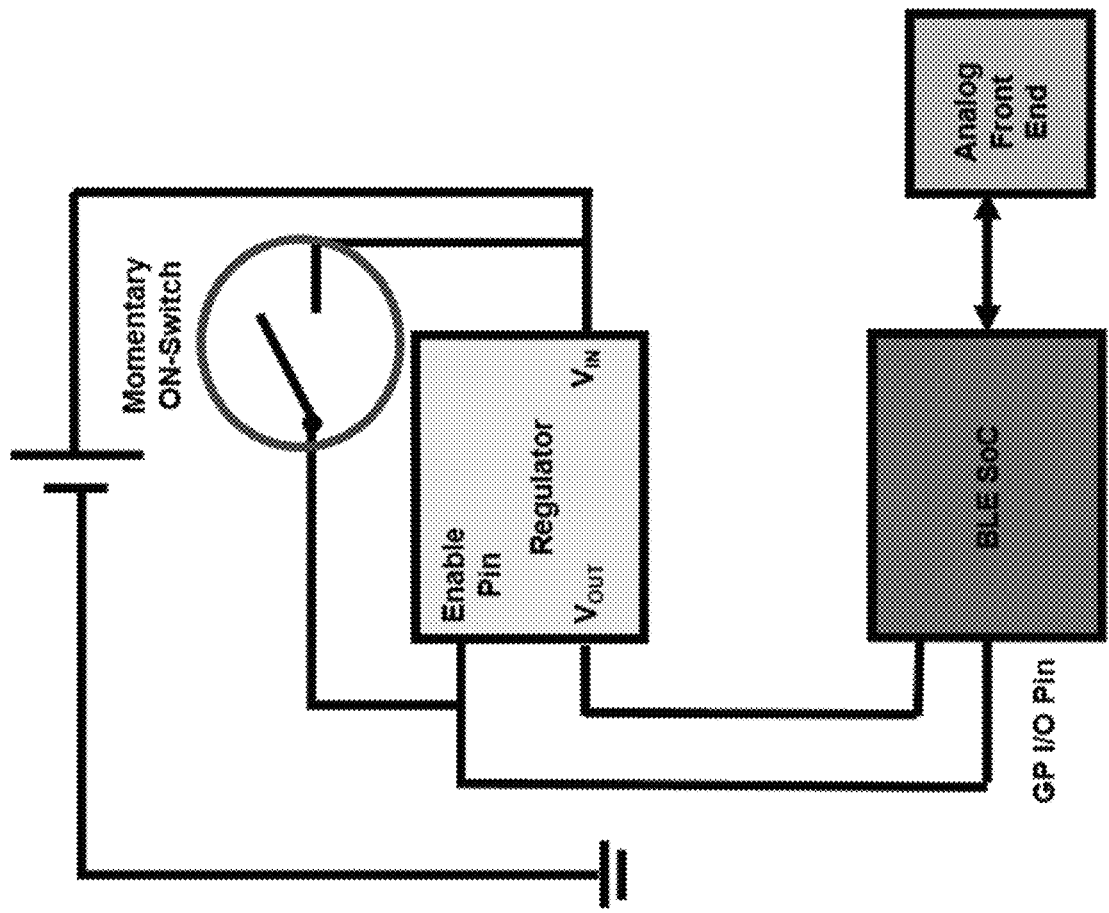
Figure 60C:
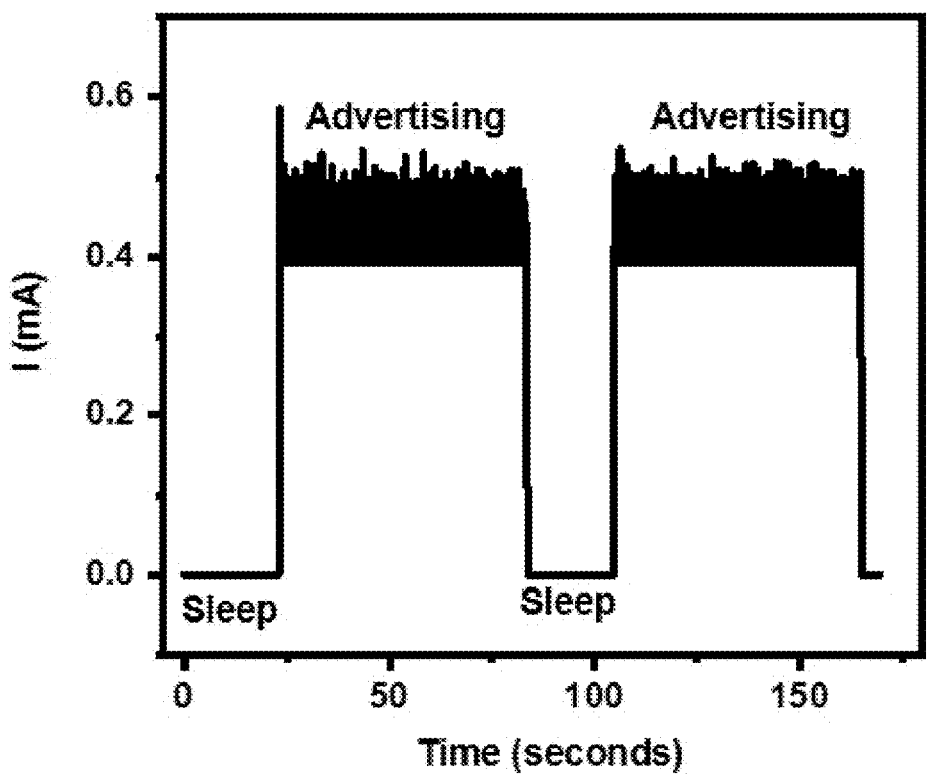
Figure 60D:
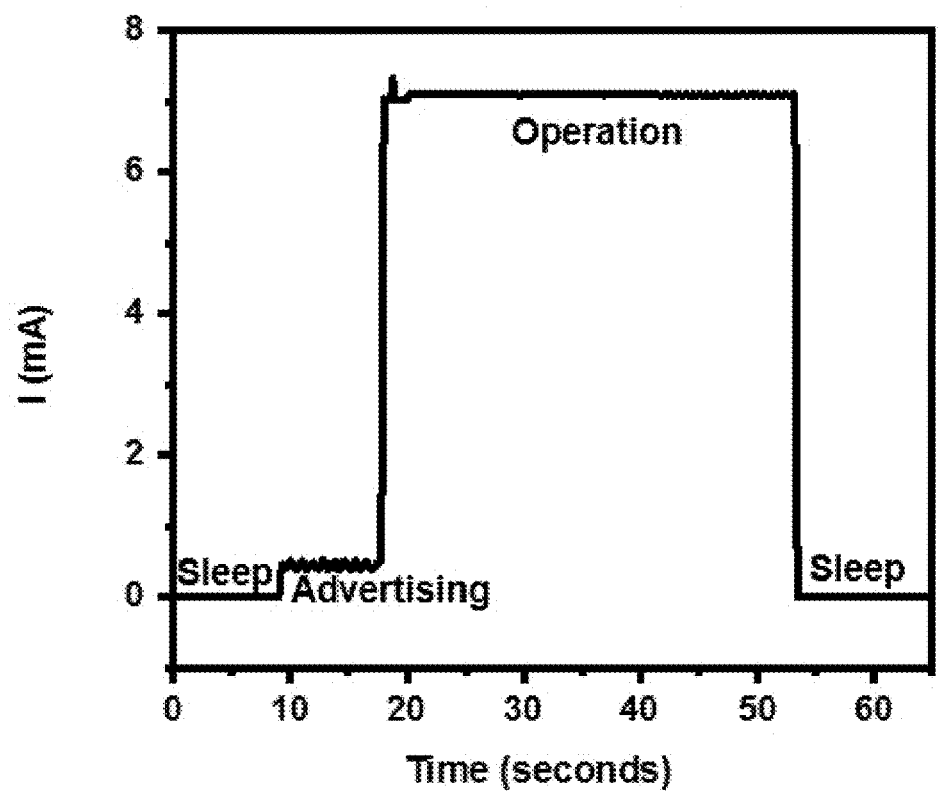

Wireless Electronics and Signal Conditioning:

Converting temperature-induced resistance changes on the NTC to a voltage that can be digitized relies on a Wheatstone bridge (FIG. 59). The voltage differential across the two arms (sensing and non-sensing) of the bridge feed into the inverting and non-inverting inputs of an operational amplifier, whose gain is tuned via a feedback resistor. The amplified signal is digitized via a 12-bit analog-digital converter (ADC) built into a Bluetooth low energy (BLE) System on Chip (SoC), with a full sensing range of 3.3V. The resultant sensor operates linearly in a temperature range between 28° C. and 40° C. with a precision of 3.5 mK. Controlled thermal actuation results from supplying a controlled voltage directly to the resistor array, in a manner that can be controlled via a metal oxide semiconductor field effect transistor (MOSFET) whose gate is switched by a general-purpose input/out (GPIO) pin on the BLE SoC. The actuation power can be tuned by pulsing the MOSFET at a programmable duty cycle.

When not in use, the device platform operates in a low energy, deep "sleep" mode that consumes ~30 nA of current. The operation of a momentary switch turns the device on, followed by a programmable period of advertising. If no pairing occurs, the device reverts to deep sleep mode, while pairing results in regular operation. This scheme is illustrated in FIGS. 60A-60D.

Data acquisition relies on a graphical interface on a tablet PC that can record and display temperature values from 4 ADCs while also providing a means for controlling thermal actuation (FIG. 53D).

Statements Regarding Incorporation by Reference and Variations

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure.

Every formulation or combination of components described or exemplified herein can be used to practice the invention, unless otherwise stated.

Whenever a range is given in the specification, for example, a numerical range, a thickness range, a modulus range, a temperature range, a time range, or a thermal conductivity range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

TABLES

TABLE 3

Thermal and geometrical quantities required for quantitative measurement of flow rate.

| Quantity | Units | Range/Value | Measurement |
|---|---|---|---|
| $k_{skin}$ | W m$^{-1}$ K | 0.30-0.50 | In vivo with epidermal transient plane source |
| $\alpha_{skin}$ | mm$^2$ s$^{-1}$ | 0.07-0.15 | In vivo with epidermal transient plane source |
| $H_{convection}$ | W m$^{-2}$ K | 6-25 | In vitro, fitting to model |
| $k_{CSF}$ | w m$^{-1}$ K | 0.5-0.6 | Known a priori |
| $\alpha_{CSF}$ | mm$^2$ s$^{-1}$ | 0.13-0.16 | Known a priori |
| $k_{Catheter}$ | W m$^{-1}$ K | 0.22 | Known a priori |
| $\alpha_{Catheter}$ | mm$^2$ s$^{-1}$ | 0.12 | Known a priori |
| $h_{skin}$ | mm | 1.5 | Radiological and acoustic imaging, transient thermal measurements |
| $ID_{catheter}$ | mm | 1.0 | Known a priori |
| $OD_{catheter}$ | mm | 1.5 | Known a priori |

TABLE 4

Summary of etiology of and measurements made on each patient.

| | Underlying Condition | Age | Sex | Malfunction Present | Flow Detected (pre-intervention) | Flow Detected (post-intervention) | Imaging Correlate | Skin Irritation |
|---|---|---|---|---|---|---|---|---|
| 1 | Pseudotumor cerebri | 36 | F | Y | N | Y | Y[1] | N |

TABLE 4-continued

Summary of etiology of and measurements made on each patient.

| | Underlying Condition | Age | Sex | Malfunction Present | Flow Detected (pre-intervention) | Flow Detected (post-intervention) | Imaging Correlate | Skin Irritation |
|---|---|---|---|---|---|---|---|---|
| 2 | Chiari I malformation | 53 | F | N | Y | N/A | N/A | N |
| 3 | Glioblastoma multiforme | 32 | M | N | Y | N/A | N/A | N |
| 4 | Glioblastoma multiforme | 58 | F | Y | N | Y | Y[2] | N |
| 5 | Post-hemorrhagic | 30 | F | Y | Y | N/A[3] | Y[4] | N |

1. Patient had visualized kinking in the neck region on X-ray post initial surgery and clinically deteriorated the morning after initial shunt placement. Radionuclide shunt study showed aberrant distal flow.
2. Patient deteriorated post-surgery and was found to have severe stool burden on abdominal CT. After bowel regimen administered, patient clinically improved and sensor readings validated resolution of pseudoobstruction.
3. Device was inadvertently destroyed during final testing and postoperative readings were unable to be obtained. Patient was noted to have changes in flow pattern with inspiration and expiration corresponding to low drainage rate seen in OR due to concomitant distal and partial proximal obstructions.
4. CT scan demonstrated interval ventriculomegaly; radionuclide study demonstrated aberrant flow patterns; X-ray and abdominal CT demonstrated catheter malpositioned extraperitoneally near liver with adjacent fluid collection (likely CSF).

TABLE 5

Raw data measured on each patient

| Patient | $\Delta T_{sensors}/T_{actuator}$ | σ | $\overline{T}_{sensors}/T_{actuator}$ | σ | Trial | Notes |
|---|---|---|---|---|---|---|
| 1 | 0.0158243 | 0.005777 | 0.365 | 0.0106 | On shunt | Pre-op, confirmed failure |
| 1 | 0.028321 | 0.008057 | 0.222 | 0.0098 | Off shunt | Pre-op, confirmed failure |
| 1 | 0.2093394 | 0.021081 | 0.2916 | 0.0052 | On shunt | Post-op, functioning shunt |
| 1 | 0.0020478 | 0.042475 | 0.2612 | 0.0148 | Off shunt | Post-op, functioning shunt |
| 2 | 0.0084 | 0.0057 | 0.2676 | 0.0106 | Off shunt | Functioning shunt |
| 2 | 0.0518 | 0.0072 | 0.2289 | 0.011 | On shunt | Functioning shunt |
| 3 | −0.0059732 | 0.001808 | 0.1601 | 0.003 | Off shunt | Functioning shunt |
| 3 | 0.0950298 | 0.003508 | 0.1815 | 0.0141 | On shunt | Functioning shunt |
| 4 | −0.0061537 | 0.010499 | 0.2104 | 0.0079 | Off shunt | Functioning shunt |
| 4 | 0.0603105 | 0.00492 | 0.3 | 0.0058 | On shunt | Functioning shunt |
| 4 | 0.1009913 | 0.009832 | 0.2247 | 0.0086 | On shunt | Functioning shunt, pumped |
| 5 | 0.000963 | 0.033035 | NA | NA | Off shunt | Malfunction with flow |
| 5 | 0.1392 | 0.0146 | 0.3297 | 0.023 | On shunt | Malfunction with flow |

TABLE 6

Summary of technical challenges and solutions during patient experiments.

| Problem | Discovery | Solutions |
| --- | --- | --- |
| Skin adhesion | During initial patient trials, factors including cleanliness of skin, multiple device uses and patient movement resulted in the delamination of initial device iterations. | A device enclosure was constructed to work in tandem with a clinical grade, skin safe adhesive. The use of such adhesive prevented minor delamination and was viable for 10 attempted uses in a subsequent trial. The enclosure gave weight to the device and prevented errant movement with patient volatility, and delamination was minimized by sizing the enclosure to be larger than the area covered by the adhesive treated sensor. |
| Motion artifact | Normal and abnormal patient movement in an initial study resulted in aberrations in captured heat data. | AFC cables present a likely source of motion related noise. The wireless iteration of the device combined with subtraction algorithms and a narrowed accepted data range (given the obtained sample and future data) have and will continue to refine and eliminate this artifact. |
| Ease of handling | The initial trial saw a great deal of difficulty in device handling for the surgeon. Due to the adhesive involved, manipulation with gloved fingers was difficult. Excess traction put on the device and its elements led to poor performance both in terms of lamination and noise artifact engendered. | The device enclosure ideated resulted in a PDMS device frame designed to aid handling by the diagnostician. This not only reduced glove related device manipulation but facilitated swift application minimizing patient discomfort. Devices were more robust and performed admirably through periods of over 10 trials. |
| Alignment | Precise alignment of the sensor to the skin overlying tunneled distal shunt catheter was occasionally difficult when attempting to approximate its center. | Winged attachments and central lines on the enclosure were designed on subsequent device iterations. These improved most applications from multiple attempts at placement to initial success in all subsequent trials. The winged attachments also had an unintended benefit to device handling. |
| Vasculature | Patients with prominent clavicular veins and superficial arterial branches adjacent to underlying shunt tubing were suspected of possible contamination. | Benchtop experiments simulated flow rates in shunts, venous and arterial systems with varying flow experiments were conducted with a fluid injector into multiple caliber tubes. |
| Skin thickness | The depth of tunneled distal shunt catheters was suspected to differ among patients with varying habituses. | Benchtop experiments, radiographic data and the academic literature were consulted in the resolution of this important question. Anecdotally, over 10 surgeons stated that based on feel and experience alone, shunt catheters were likely 1-8 mm under the skin. Further experiments demonstrated sensor performance to a depth of 6 mm. Measurements shunt catheter to surface distance of available computerized tomography scans of patients was also performed, with an average total thickness of subcutaneous tissue overlying the distal catheter of 1.52 mm. Finally, a comprehensive literature search was performed. Established factors including total soft tissue to bony protuberance distance to skin (under 2 mm), |

We claim:

1. A device to measure a subdermal fluid flow parameter comprising:
   a substrate;
   at least one upstream temperature sensor supported by the substrate;
   at least one downstream temperature sensor supported by the substrate; and
   a thermal actuator supported by the substrate and positioned between said upstream temperature sensor and said downstream temperature sensor;
   wherein the thermal actuator comprises an array of resistors having a cumulative resistivity sufficient to provide for thermal actuation such that the upstream temperature sensor measures an upstream temperature and said downstream temperature sensor measures a downstream temperature to allow determination of said subdermal fluid flow parameter; and wherein the array of resistors of the thermal actuator provides a fill factor selected from the range of 10% to 60% of an area between said upstream temperature sensor and said downstream temperature sensor.

2. The device of claim 1, further comprising a microprocessor in electronic communication with the downstream temperature sensor and the upstream temperature sensor to calculate subdermal fluid flow parameter from the measured upstream and downstream temperatures.

3. The device of claim 1, wherein said area between said upstream temperature sensor and said downstream temperature sensor is 5%-60% of total printed circuit board footprint area of the device.

* * * * *